(12) United States Patent
Yoshida et al.

(10) Patent No.: US 9,842,996 B2
(45) Date of Patent: Dec. 12, 2017

(54) AMINE COMPOUND HAVING HETERO-FUSED RING AND ORGANIC ELECTROLUMINESCENT ELEMENT USING AMINE COMPOUND

(71) Applicant: Idemitsu Kosan Co., Ltd., Chiyoda-ku, Tokyo (JP)

(72) Inventors: Kei Yoshida, Sodegaura (JP); Toshihiro Iwakuma, Sodegaura (JP); Ryohei Hashimoto, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 155 days.

(21) Appl. No.: 14/771,170

(22) PCT Filed: Mar. 18, 2014

(86) PCT No.: PCT/JP2014/001545
§ 371 (c)(1),
(2) Date: Aug. 27, 2015

(87) PCT Pub. No.: WO2014/148047
PCT Pub. Date: Sep. 25, 2014

(65) Prior Publication Data
US 2016/0013419 A1      Jan. 14, 2016

(30) Foreign Application Priority Data

Mar. 22, 2013 (JP) ................................. 2013-059300

(51) Int. Cl.
*H01L 51/00*      (2006.01)
*C07D 491/147*   (2006.01)
(Continued)

(52) U.S. Cl.
CPC ...... *H01L 51/0061* (2013.01); *C07D 491/147* (2013.01); *C09K 11/06* (2013.01);
(Continued)

(58) Field of Classification Search
None
See application file for complete search history.

(56) References Cited

U.S. PATENT DOCUMENTS

2012/0168734 A1   7/2012   Park et al.
2015/0270496 A1   9/2015   Nakano et al.

FOREIGN PATENT DOCUMENTS

WO   WO-2011/019173 A2   2/2011
WO   WO-2014/057684 A1   4/2014
WO   WO-2014/057685 A1   4/2014

OTHER PUBLICATIONS

International Search Report issued in PCT/JP2014/001545 dated Jun. 17, 2014.
(Continued)

*Primary Examiner* — J. L. Yang
(74) *Attorney, Agent, or Firm* — Foley & Lardner LLP

(57) ABSTRACT

A compound represented by the following formula (1).

(1)

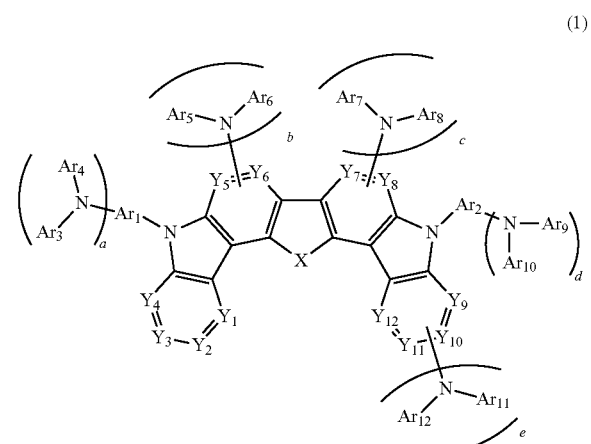

23 Claims, 1 Drawing Sheet

(51) Int. Cl.
 C09K 11/06 (2006.01)
 H05B 33/14 (2006.01)
 H01L 51/50 (2006.01)
(52) U.S. Cl.
 CPC ........ *H01L 51/006* (2013.01); *H01L 51/0059* (2013.01); *H01L 51/0071* (2013.01); *H01L 51/0072* (2013.01); *H01L 51/0073* (2013.01); *H05B 33/14* (2013.01); *C09K 2211/1007* (2013.01); *C09K 2211/1011* (2013.01); *C09K 2211/1014* (2013.01); *C09K 2211/1029* (2013.01); *C09K 2211/1044* (2013.01); *C09K 2211/1088* (2013.01); *H01L 51/0052* (2013.01); *H01L 51/0085* (2013.01); *H01L 51/5016* (2013.01); *H01L 51/5056* (2013.01); *H01L 51/5072* (2013.01); *H01L 51/5088* (2013.01); *H01L 51/5096* (2013.01)

(56) References Cited

OTHER PUBLICATIONS

International Preliminary Report on Patentability issued in PCT/JP2014/001545 dated Sep. 22, 2015.

AMINE COMPOUND HAVING HETERO-FUSED RING AND ORGANIC ELECTROLUMINESCENT ELEMENT USING AMINE COMPOUND

TECHNICAL FIELD

The invention relates to a novel amine compound having a hetero-fused ring, a material for an organic electroluminescence device using the same and an organic electroluminescence device.

BACKGROUND ART

An organic electroluminescence (EL) device is classified into a fluorescent organic EL device and a phosphorescent organic EL device, and a device design optimum for the emission mechanism of each type of organic EL devices has been studied. It is known that a highly efficient phosphorescent organic EL device cannot be obtained by merely applying a fluorescent device technology due to the emission characteristics thereof.

Specifically, since phosphorescence emission utilizes triplet excitons, a compound used for forming an emitting layer must have a large energy gap. This is because the energy gap (hereinafter often referred to as "singlet energy") of a compound is normally larger than the triplet energy (in the invention, the triplet energy means the difference in energy between the lowest excited triplet state and the ground state) of the compound.

As the material for a phosphorescent organic EL device, Patent Document 1 discloses a phosphorescent host material having a line-symmetrical structure, for example.

RELATED ART DOCUMENT

Patent Document

Patent Document 1: WO2011/019173

SUMMARY OF THE INVENTION

An object of the invention is to provide a novel compound capable of realizing a highly efficient organic EL device.

According to one aspect of the invention, a compound represented by the following formula (1) is provided.

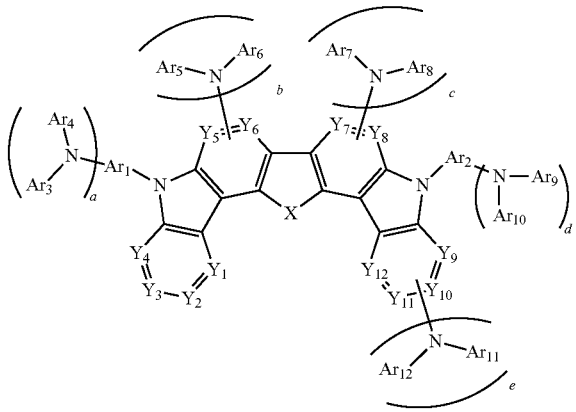

wherein in the formula (1),
X is O, S or a group represented by N-Ra;
$Y_1$ to $Y_4$ are independently N or a group represented by C-Ra;
$Y_5$ and $Y_6$ are independently N, a group represented by C-Ra or a carbon atom that is bonded to $-N(Ar_5)(Ar_6)$;
$Y_7$ and $Y_8$ are independently N, a group represented by C-Ra or a carbon atom that is bonded to $-N(Ar_7)(Ar_8)$;
$Y_9$ to $Y_{12}$ are independently N, a group represented by C-Ra or a carbon atom that is bonded to $-N(Ar_{11})(Ar_{12})$;
$Ar_1$ to $Ar_{12}$ are independently a substituted or unsubstituted aromatic hydrocarbon group including 6 to 30 carbon atoms that form a ring (hereinafter referred to as "ring carbon atoms") or a substituted or unsubstituted aromatic heterocyclic group including 3 to 30 atoms that form a ring (hereinafter referred to as "ring atoms");
Ra is a hydrogen atom, a substituted or unsubstituted aromatic hydrocarbon group including 6 to 30 ring carbon atoms, a substituted or unsubstituted aromatic heterocyclic group including 3 to 30 ring atoms, a substituted or unsubstituted alkyl group including 1 to 30 carbon atoms, a substituted or unsubstituted fluoroalkyl group including 1 to 30 carbon atoms, a substituted or unsubstituted cycloalkyl group including 3 to 30 ring carbon atoms, a substituted or unsubstituted aralkyl group including 7 to 30 carbon atoms, a substituted phosphoryl group, a substituted silyl group, a cyano group, a nitro group or a carboxy group,
when plural Ras are present in the formula (1), the plural Ras may be the same or different from each other, and the plural Ras may form a ring;
when $Ar_1$ is a p-phenylene group, $Ar_3$ and $Ar_4$ are not both an unsubstituted phenyl group;
when $Ar_2$ is a p-phenylene group, $Ar_9$ and $Ar_{10}$ are not both an unsubstituted phenyl group;
a is an integer of 0, 1 or 2;
b is an integer of 0, 1 or 2;
c is an integer of 0, 1 or 2;
d is an integer of 0, 1 or 2;
e is an integer of 0, 1, 2, 3 or 4; and
a+b+c+d+e is 1 to 6.

According to the invention, a compound that enables an organic EL device to emit light at a high efficiency can be provided.

MODE FOR CARRYING OUT THE INVENTION

Figure 1:
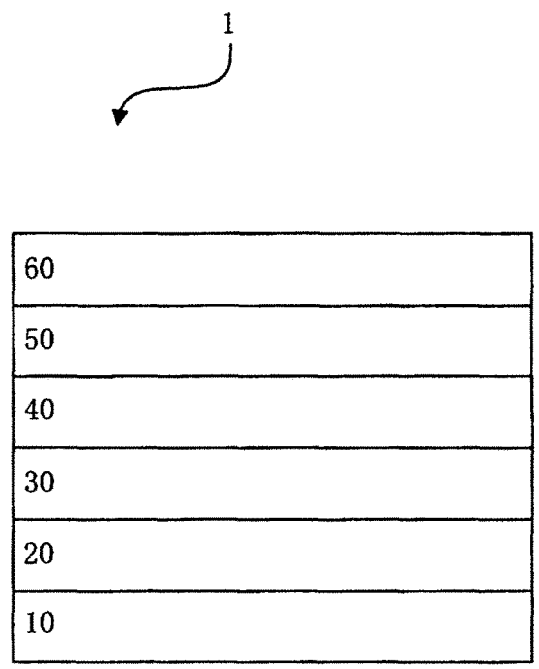
FIG. 1 is a view showing one embodiment of the organic EL device of the invention.

The compound according to one aspect of the invention is represented by the following formula (1):

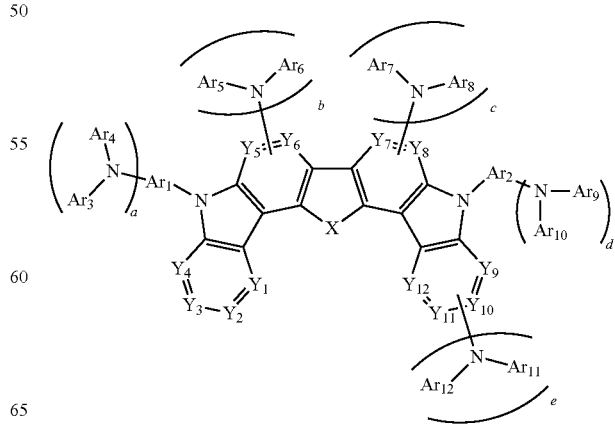

wherein in the formula (1),

X is O, S or a group represented by N-Ra;

$Y_1$ to $Y_4$ are independently N or a group represented by C-Ra;

$Y_5$ and $Y_6$ are independently N, a group represented by C-Ra or a carbon atom that is bonded to —N($Ar_5$)($Ar_6$);

$Y_7$ and $Y_8$ are independently N, a group represented by C-Ra or a carbon atom that is bonded to —N($Ar_7$)($Ar_8$);

$Y_9$ to $Y_{12}$ are independently N, a group represented by C-Ra or a carbon atom that is bonded to —N($Ar_{11}$)($Ar_{12}$);

$Ar_1$ to $Ar_{12}$ are independently a substituted or unsubstituted aromatic hydrocarbon group including 6 to 30 ring carbon atoms or a substituted or unsubstituted aromatic heterocyclic group including 3 to 30 ring atoms;

Ra is a hydrogen atom, a substituted or unsubstituted aromatic hydrocarbon group including 6 to 30 ring carbon atoms, a substituted or unsubstituted aromatic heterocyclic group including 3 to 30 ring atoms, a substituted or unsubstituted alkyl group including 1 to 30 carbon atoms, a substituted or unsubstituted fluoroalkyl group including 1 to 30 carbon atoms, a substituted or unsubstituted cycloalkyl group including 3 to 30 ring carbon atoms, a substituted or unsubstituted aralkyl group including 7 to 30 carbon atoms, a substituted phosphoryl group, a substituted silyl group, a cyano group, a nitro group or a carboxy group;

when plural Ras are present in the formula (1), the plural Ras may be the same or different from each other, and the plural Ras may form a ring;

when $Ar_1$ is a p-phenylene group, $Ar_3$ and $Ar_4$ are not both an unsubstituted phenyl group;

when $Ar_2$ is a p-phenylene group, $Ar_9$ and $Ar_{10}$ are not both an unsubstituted phenyl group;

a is an integer of 0, 1 or 2;

b is an integer of 0, 1 or 2;

c is an integer of 0, 1 or 2;

d is an integer of 0, 1 or 2;

e is an integer of 0, 1, 2, 3 or 4; and a+b+c+d+e is 1 to 6.

The compound according to one aspect of the invention has, as a central skeleton, a bisindolodibenzofuran skeleton, a bisindolodibenzothiophene skeleton, or a bisindolocarbazole skeleton, which is a skeleton with an extended π-conjugated plane, and constitutes a ladder structure. Since this ladder structure has a small ionization potential and has excellent hole-injecting properties, by using this compound as a material for an organic EL device, the organic EL device can be driven at a lower voltage and, due to an increase in amount of carriers injected to the emitting layer, the organic EL device can be driven more efficiently.

Further, the compound according to one aspect of the invention is a wide band-gap material, and blocks leakage of electrons from the emitting layer to the hole-transporting layer, and hence contributes to prolongation of life and increase in efficiency of the device.

Hereinbelow, an explanation will be made on examples of each group of the compound represented by the formula (1).

As the alkyl group including 1 to 30 carbon atoms, a straight-chain or branched alkyl group can be given. Specifically, a methyl group, an ethyl group, a propyl group, an isopropyl group, a n-butyl group, an isobutyl group, a sec-butyl group, a tert-butyl group, a n-pentyl group, a n-hexyl group, a n-heptyl group, a n-octyl group or the like can be given. A methyl group, an ethyl group, a propyl group, an isopropyl group, a n-butyl group, an isobutyl group, a sec-butyl group and a tert-butyl group can be preferably given, with a methyl group, an ethyl group, a propyl group, an isopropyl group, a n-butyl group, a sec-butyl group and a tert-butyl group being more preferable.

As the fluoroalkyl group including 1 to 30 carbon atoms, a group in which the alkyl group mentioned above is substituted by one or more fluorine atoms can be given. As specific examples thereof, a fluoromethyl group, a difluoromethyl group, a trifluoromethyl group, a fluoroethyl group, a trifluoromethylmethyl group, a pentafluoroethyl group or the like can be given. A trifluoromethyl group and a pentafluoroethyl group are preferable.

As the cycloalkyl group including 3 to 30 ring carbon atoms, a cyclopropyl group, a cyclobutyl group, a cyclopentyl group, a cyclohexyl group, a 1-adamantyl group, a 2-adamantyl group, a 1-norbornyl group, a 2-norbornyl group or the like can be given. A cyclopentyl group and a cyclohexyl group are preferable.

The "ring carbon atoms" mean carbon atoms that constitute a saturated ring, an unsaturated ring or an aromatic ring.

The aromatic hydrocarbon group including 6 to 30 ring carbon atoms is preferably an aromatic hydrocarbon group including 6 to 20 ring carbon atoms.

Specific examples of the aromatic hydrocarbon group include a phenyl group, a naphthyl group, an anthryl group, a phenanthryl group, a naphthacenyl group, a pyrenyl group, a chrysenyl group, a benzo[c]phenanthryl group, a benzo[g]chrysenyl group, a triphenylenyl group, a fluorenyl group, a benzofluorenyl group, a dibenzofluorenyl group, a biphenyl group, a terphenyl group, a quarterphenyl group, a fluoranthenyl group or the like can be given.

A phenyl group, a naphthyl group, an anthryl group, a triphenyl group, a fluorenyl group, a benzofluorenyl group, a biphenyl group, a terphenyl group, a phenanthryl group and a fluoranthenyl group are preferable.

The aromatic heterocyclic group including 3 to 30 ring atoms is preferably an aromatic heterocyclic group including 5 to 30 ring atoms.

Specific examples of the aromatic heterocyclic group include a pyrrolyl group, a pyrazinyl group, a pyridinyl group, a pyrimidinyl group, a triazinyl group, an indolyl group, an isoindolyl group, an imidazolyl group, a furyl group, a benzofuranyl group, an isobenzofuranyl group, a dibenzofuranyl group, a dibenzothiophenyl group, an azadibenzofuranyl groups, an azadibenzothiophenyl group, a diazadibenzofuranyl group, a diazadibenzothiophenyl group, a quinolyl group, an isoquinolyl group, a quinoxalinyl group, a carbazolyl group, a phenanthridinyl group, an acridinyl group, a phenanthrolinyl group, a phenazinyl group, a phenothiazinyl group, a phenoxazinyl group, an oxazolyl group, an oxadiazolyl group, a furazanyl group, a thienyl group, benzothiophenyl group, a dihydroacridinyl group, an azacarbazolyl group, a diazacarbazolyl group and a quinazolinyl group. A pyridinyl group, a pyrimidinyl group, a triazinyl group, a dibenzofuranyl group, a dibenzothiophenyl group, a dibenzothiophenyl group, an azadibenzofuranyl group, an azadibenzothiophenyl group, a diazadibenzofuranyl group, a diazadibenzothiophenyl group, a carbazolyl group, an azacarbazolyl group, and a diazacarbazolyl group are preferable.

The aralkyl group including 7 to 30 carbon atoms is represented by —Y—Z. As examples of Y, the examples of an alkylene group corresponding to the examples of the above-mentioned examples of the alkyl group can be given. As examples of Z, the examples of the above-mentioned aryl group can be given.

It is preferred that the aryl part of the aralkyl group have 6 to 20 ring carbon atoms. The alkyl part preferably has 1 to 8 carbon atoms. As the aralkyl group, a benzyl group, a phenylethyl group and a 2-phenylpropane-2-yl group are given, for example.

A substituted phosphoryl group is a group represented by —P(=O)RbRc, for example. A substituted silyl group is a group represented by —SiRbRcRd, for example.

Rb, Rc and Rd are independently a substituted or unsubstituted aromatic hydrocarbon group including 6 to 30 ring carbon atoms, a substituted or unsubstituted aromatic heterocyclic group including 3 to 30 ring atoms, a substituted or unsubstituted alkyl group including 1 to 30 carbon atoms, a substituted or unsubstituted fluoroalkyl group including 1 to 30 carbon atoms or a substituted or unsubstituted cycloalkyl group including 3 to 30 ring carbon atoms.

Each group of these Rb, Rc and Rd is the same as those mentioned above.

As the substituent of the "substituted or unsubstituted . . . " of each of the above-mentioned groups, the alkyl group, the cycloalkyl group, the fluoroalkyl group, the aromatic hydrocarbon group and the aromatic heterocyclic group can be given. In addition, a halogen atom (fluorine, chlorine, bromine, iodine or the like can be given, and a fluorine atom is preferably given), a hydroxyl group, a nitro group, a cyano group, a carboxy group, an aryloxy group, a diarylamine group or the like can be given.

These substituents may be further substituted by the above-mentioned substituents. Further, a plurality of these substituents may be bonded to each other to form a ring.

The "unsubstituted" in the "substituted or unsubstituted" means that the group is not substituted by the above-mentioned substituent, and a hydrogen atom is bonded.

In the present specification, the number of the ring carbon atoms mean, in a compound having a structure in which atoms are bonded in a ring-like form (for example, a monocyclic compound, a fused ring compound, a cross-linking compound, a carbocyclic compound or a heterocyclic compound), the number of carbon atoms among the atoms that constitute the ring itself. When the ring is substituted by a substituent, the carbon contained in the substituent is not included in the ring carbon atoms. The same is applied to the number of "ring carbon atoms" mentioned below, unless otherwise indicated. For example, the benzene ring includes 6 ring carbon atoms, the naphthalene ring includes 10 ring carbon atoms, the pyridinyl group includes 5 ring carbon atoms and the furanyl group includes 4 ring carbon atoms. If the benzene ring or the naphthalene ring is substituted by an alkyl group as a substituent, for example, the number of carbon atoms of the alkyl group is not included in the number of the ring carbon atoms. Further, if a fluorene ring is bonded to a fluorene ring as a substituent, for example (including a spirofluorene ring), the number of carbon atoms of the fluorene ring as a substituent is not included in the number of the ring carbon atoms.

In the present specification, the number of the ring atoms mean, in a compound (for example, a monocyclic compound, a fused ring compound, a cross-linking compound, a carbocyclic compound or a heterocyclic compound) having a structure in which atoms are bonded in a ring-like form (for example, a monocyclic ring, a fused ring or a ring assembly), the number of atoms that constitute the ring itself. Atoms that do not constitute a ring (for example, hydrogen atoms bonding atoms that constitute the ring) or atoms contained in a substituent when the ring is substituted by the substituent are not included in the ring atoms. The same is applied to the number of the "ring atoms" mentioned below, unless otherwise indicated. For example, a pyridine ring has 6 ring atoms, a quinazoline ring has 10 ring atoms and a furan ring has 5 ring atoms. Hydrogen atoms that are respectively bonded to the carbon atoms of the pyridine ring or the quinazoline ring or atoms that constitute the substituent are not included in ring atoms. Further, if a fluorene ring is bonded to a fluorene ring as a substituent (including a spirofluorene ring), the number of atoms of the fluorene ring as a substituent is not included in the number of the ring atoms.

In the specification, the "XX to YY carbon atoms" in the "substituted or unsubstituted ZZ group including XX to YY carbon atoms" indicates the number of carbon atoms when the ZZ group is unsubstituted, and does not include the number of carbon atoms of a substituent when the ZZ group is substituted. Here, the "YY" is larger than the "XX", and the "XX" and the "YY" independently mean an integer of 1 or more.

In the present specification, the "XX to YY atoms" in the "substituted or unsubstituted ZZ group including XX to YY atoms" indicates the number of atoms when the ZZ group is unsubstituted, and does not include the number of atoms of a substituent when the ZZ group is substituted. Here, the "YY" is larger than "XX", and the "XX" and the "YY" independently mean an integer of 1 or more.

In the invention, the hydrogen atom includes isomers differing in number of neutrons, i.e. protium, deuterium and tritium.

If plural Ras are present in the formula (1), the plural Ras may be the same or different, and the plural Ras may form a ring. As the ring, a saturated ring, an unsaturated ring or an aromatic ring can be given.

When plural Ras are present and they form a ring, compounds having a partial structure shown below can be given as examples, although the case is not restricted to them.

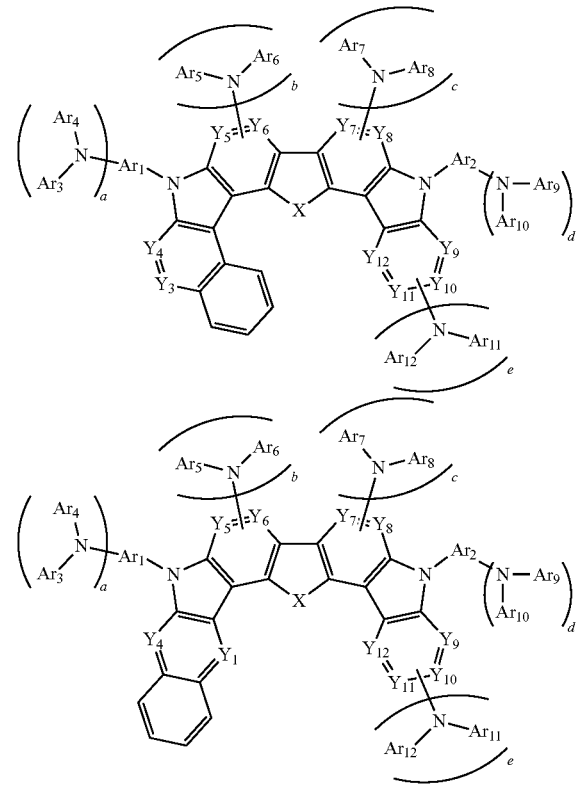

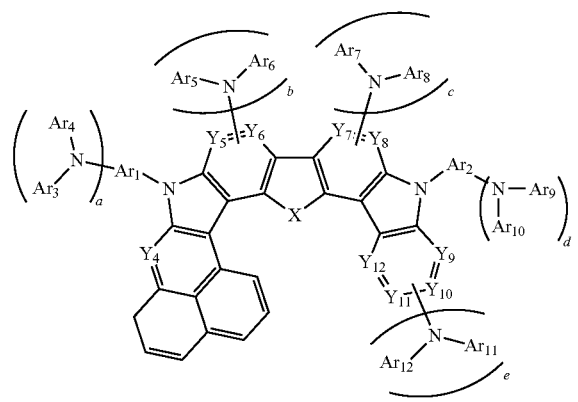
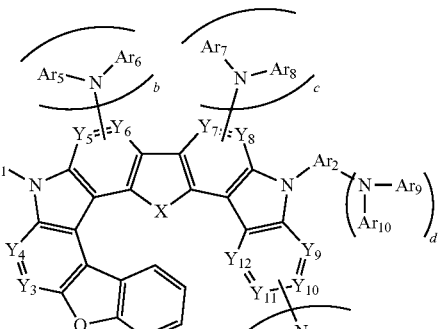
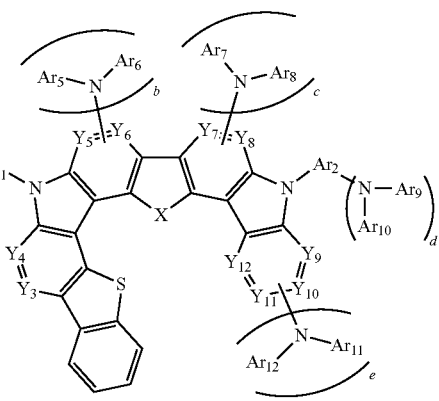
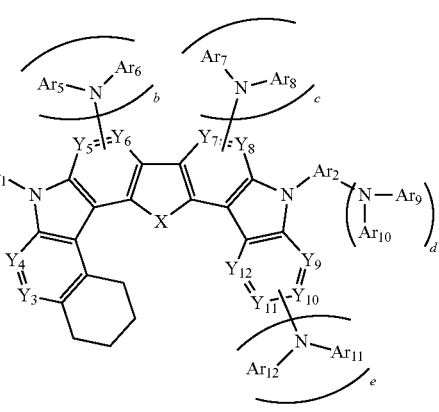
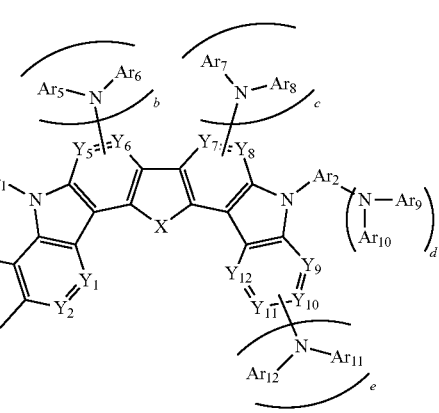

-continued

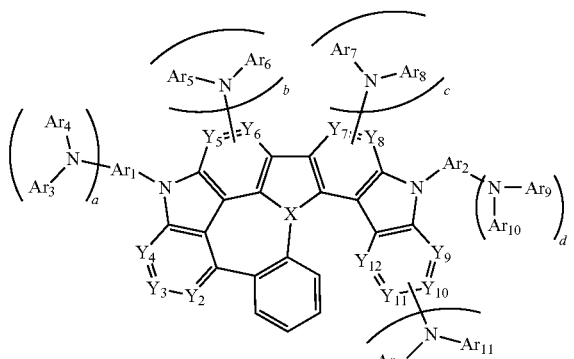

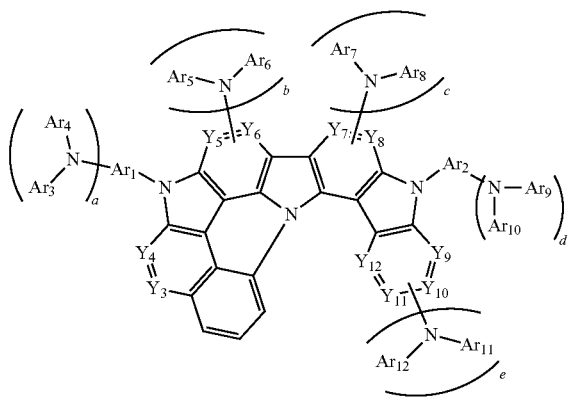

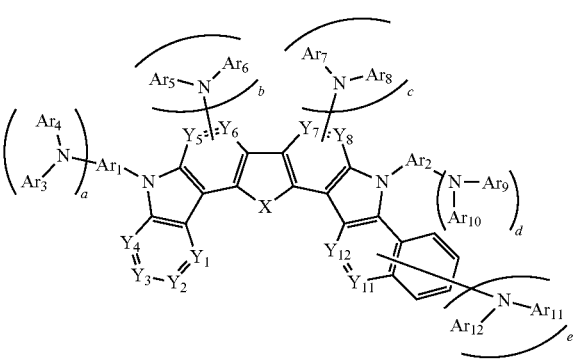

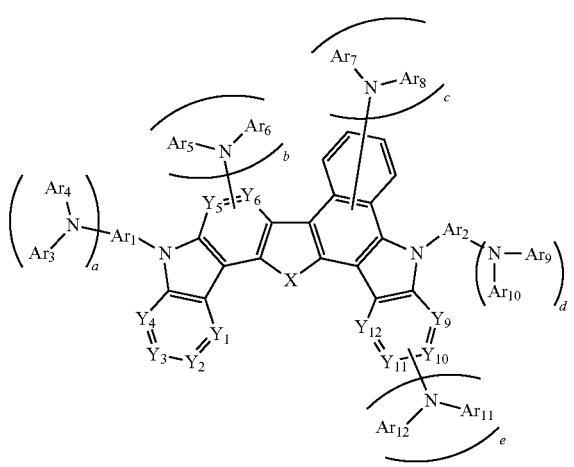

-continued

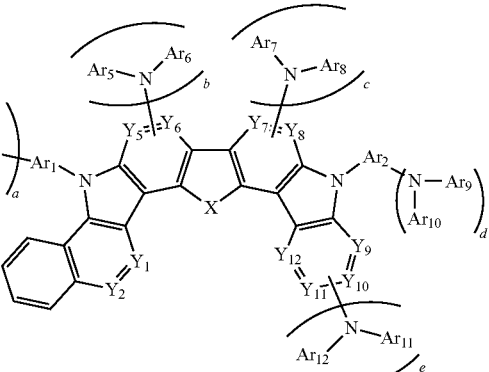

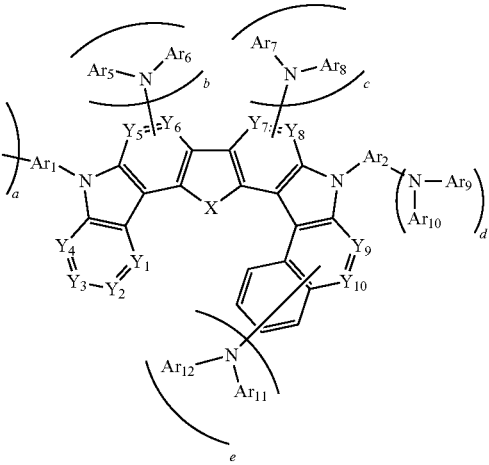

According to one aspect of the invention, it is preferred that at least one of a and d in the formula (1) be 1.

Further, according to one aspect of the invention, in the formula (1), it is preferred that a be 0 and b+c+d+e be 1 to 4.

According to one aspect of the invention, in the formula (1), it is preferred that e be 0 and a+b+c+d be 1 to 4.

According to one aspect of the invention, in the formula (1), it is preferred that a and d be 0 and b+c+e be 1 to 4.

According to one aspect of the invention, it is preferred that, in the formula (1), a and e be 0 and b+c+d be 1 to 4.

According to one aspect of the invention, it is preferred that, in the formula (1), a, d and e be 0 and b+c be 1 or 2.

According to one aspect of the invention, it is preferred that, in the formula (1), a, b and c be 0 and d be 1.

According to one aspect of the invention, it is preferred that, in the formula (1), a, b, c and e be 0 and d be 1.

Further, according to one aspect of the invention, it is preferred that $Ar_1$ and $Ar_2$ in the formula (1) be independently a substituted or unsubstituted phenylene group, a substituted or unsubstituted naphthalenediyl group, a substituted or unsubstituted anthracenediyl group, a substituted or unsubstituted triphenylenediyl group, a substituted or unsubstituted fluorenediyl group, a substituted or unsubstituted benzofluorenediyl group, a substituted or unsubstituted biphenyldiyl group, a substituted or unsubstituted terphenyldilyl group, a substituted or unsubstituted phenanthrenediyl group, a substituted or unsubstituted fluoranthenediyl group, a substituted or unsubstituted pyridinediyl group, a substituted or unsubstituted pyrimidinediyl group, a substituted or unsubstituted triazinediyl group, a substituted or unsubstituted dibenzofuranediyl group, a substituted or unsubstituted dibenzothiophenediyl group, a substituted or unsubstituted azadibenzofuranediyl group, a substituted or unsubstituted azadibenzothiophenediyl group, a substituted or unsubstituted diazadibenzofuranediyl group, a substituted or unsubstituted diazadibenzothiophenediyl group, a substituted or unsubstituted carbazolediyl group, a substituted or unsubstituted azacarbazolediyl group or a substituted or unsubstituted diazacarbazolediyl group.

According to one aspect of the invention, it is preferred that $Ar_1$ and $Ar_2$ in the formula (1) be independently a substituted or unsubstituted m-phenylene group, a substituted or unsubstituted o-phenylene group, a substituted or unsubstituted naphthalenediyl group, a substituted or unsubstituted triphenylenediyl group, a substituted or unsubstituted fluorenediyl group, a substituted or unsubstituted biphenyldiyl group, a substituted or unsubstituted terphenyldiyl group, a substituted or unsubstituted phenanthrenediyl group, a substituted or unsubstituted dibenzofurandiyl group or a substituted or unsubstituted dibenzothiophenediyl group.

According one aspect of the invention, it is preferred that $Ar_1$ and $Ar_2$ in the formula (1) be independently a substituted or unsubstituted fluorenediyl group or a substituted or unsubstituted biphenyldiyl group.

Further, according to one aspect of the invention, it is preferred that $Ar_3$ to $Ar_{12}$ in the formula (1) be independently a substituted or unsubstituted phenyl group, a substituted or unsubstituted naphthyl group, a substituted or unsubstituted anthryl group, a substituted or unsubstituted triphenylenyl group, a substituted or unsubstituted fluorenyl group, a substituted or unsubstituted benzofluorenyl group, a substituted or unsubstituted biphenyl group, a substituted or unsubstituted terphenyl group, a substituted or unsubstituted phenanthryl group, a substituted or unsubstituted fluoranthenyl group, a substituted or unsubstituted pyridinyl group, a substituted or unsubstituted pyrimidinyl group, a substituted or unsubstituted triazinyl group, a substituted or unsubstituted dibenzofuranyl group, a substituted or unsubstituted dibenzothiophenyl group, a substituted or unsubstituted azadibenzofuranyl group, a substituted or unsubstituted azadibenzothiophenyl group, a substituted or unsubstituted diazadibenzofuranyl group, a substituted or unsubstituted diazadibenzothiophenyl group, a substituted or unsubstituted carbazolyl group, azacarbazolyl group or a substituted or unsubstituted diazacarbazolyl group.

According to one aspect of the invention, it is preferred that $Y_1$ to $Y_4$ in the formula (1) be independently a group represented by C-Ra, $Y_5$ and $Y_6$ be independently a group represented by C-Ra or a carbon atom that is bonded to $N(Ar_5)(Ar_6)$, $Y_7$ and $Y_8$ be independently a group represented by C-Ra or a carbon atom that is bonded to $N(Ar_7)(Ar_8)$, and $Y_9$ to $Y_{12}$ be independently a group represented by C-Ra or a carbon atom that is bonded to $N(Ar_{11})(Ar_{12})$.

As long as they are no inconsistencies, the aspects of the above-mentioned embodiments can be appropriately combined.

No specific restrictions are imposed on the method for producing the compound represented by the formula (1), and it can be produced by a known method.

Hereinbelow, specific examples of the compound represented by the formula (1) are given below.

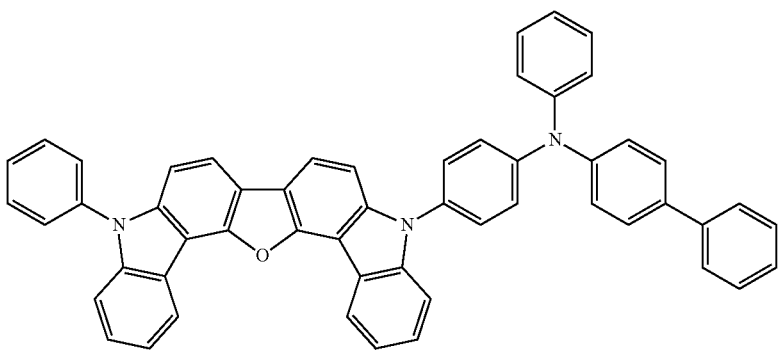

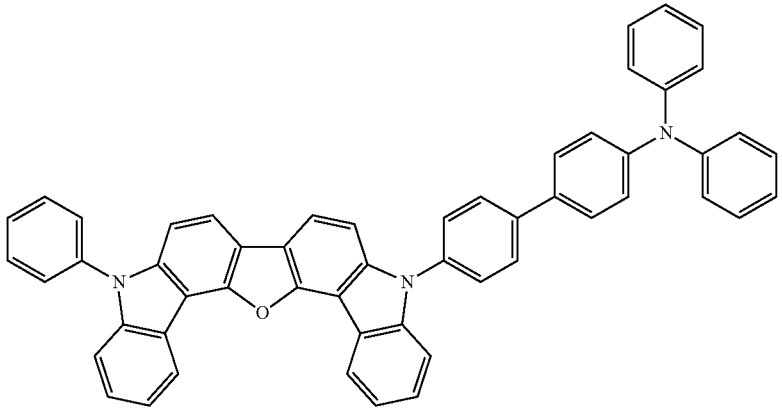

-continued
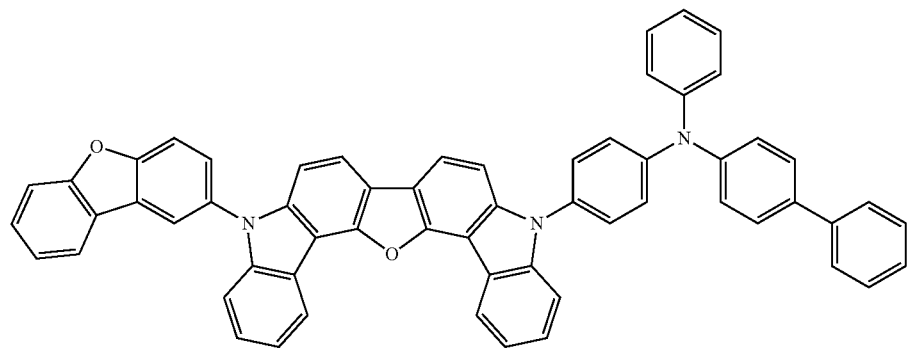
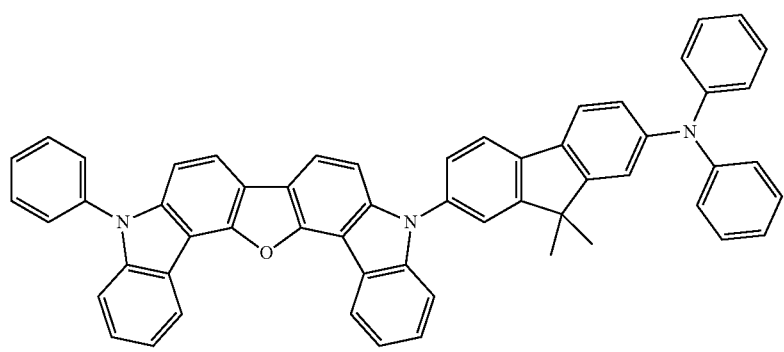
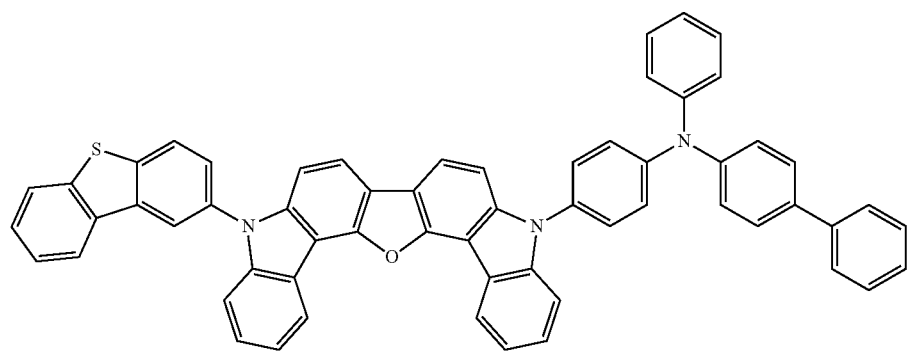
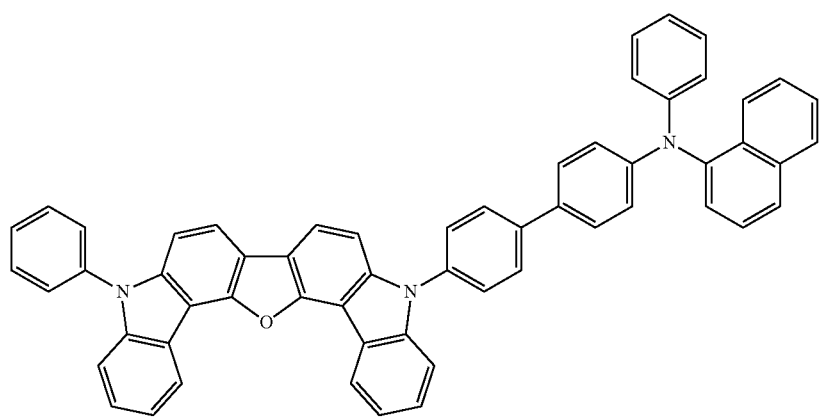

-continued
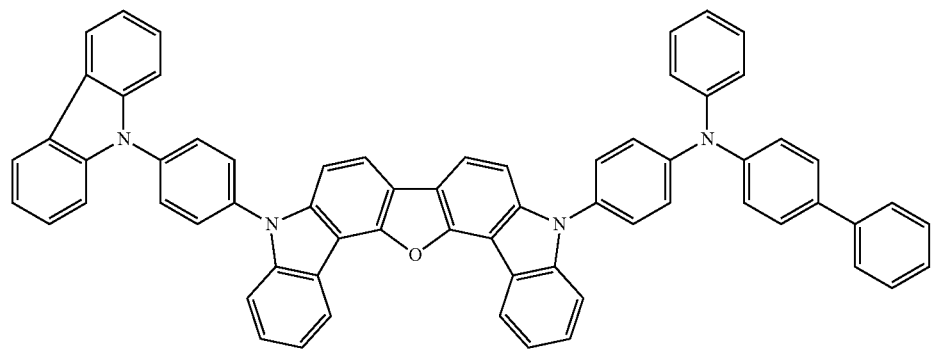
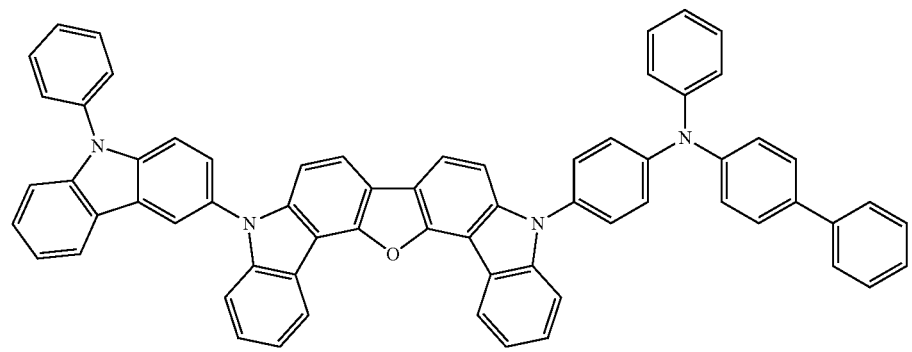
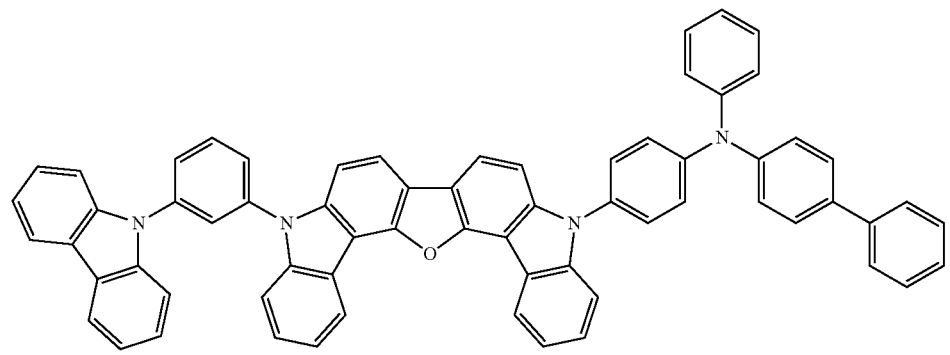
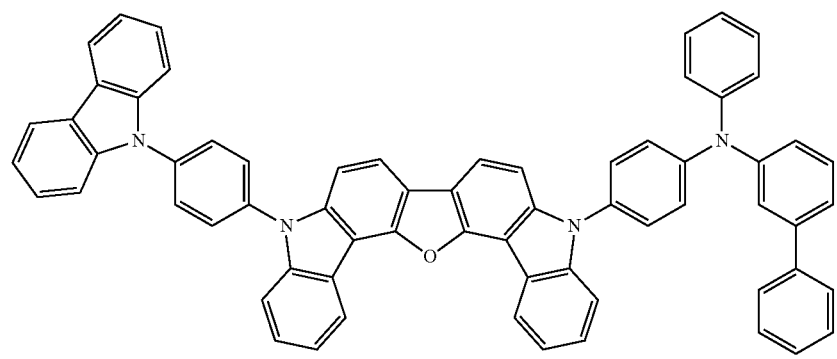
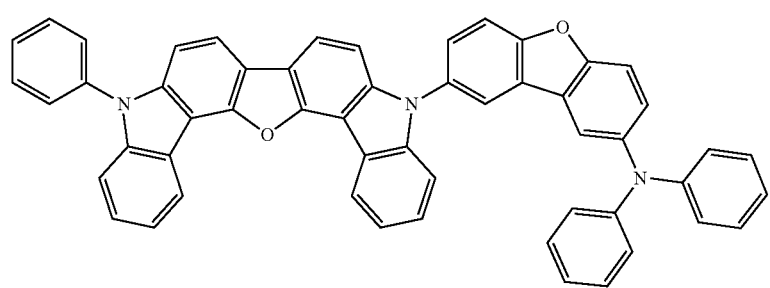

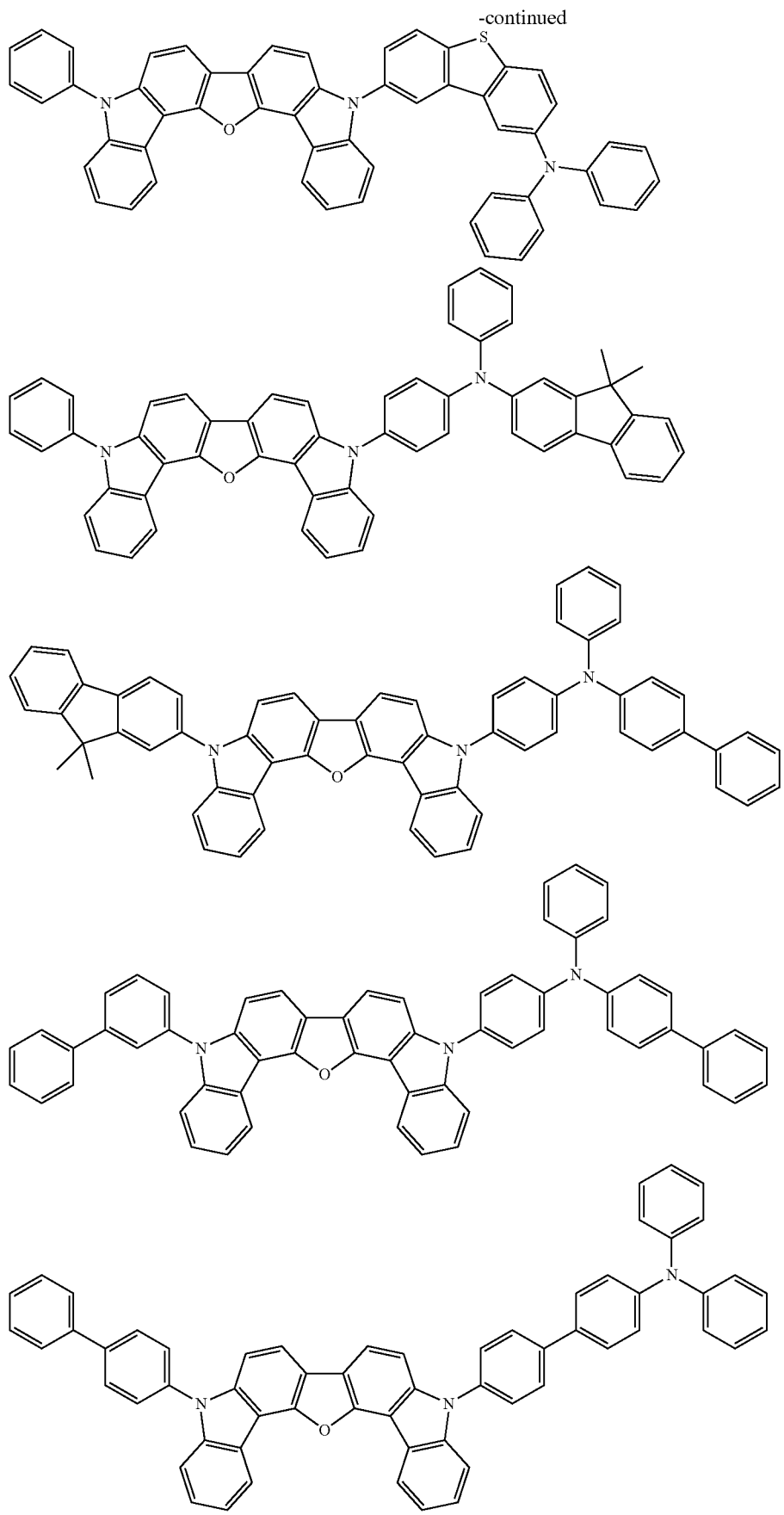

-continued
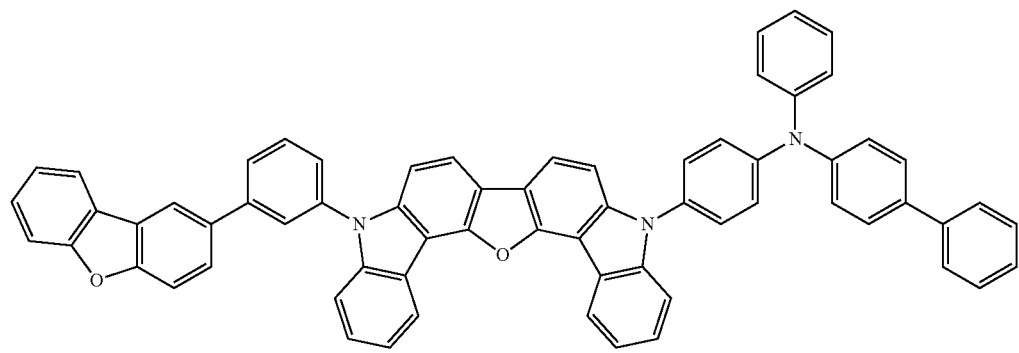
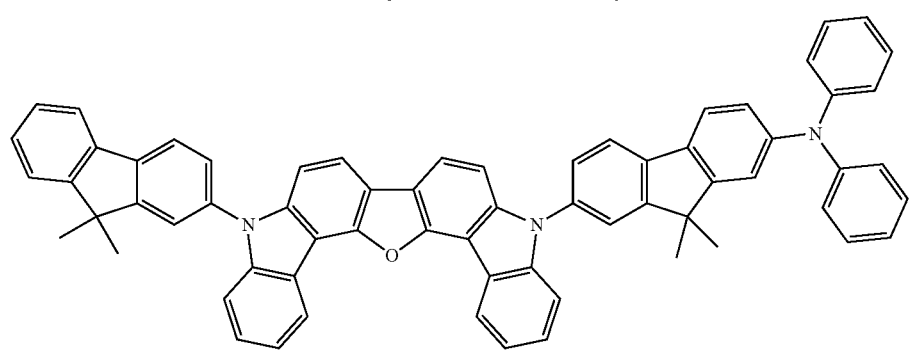
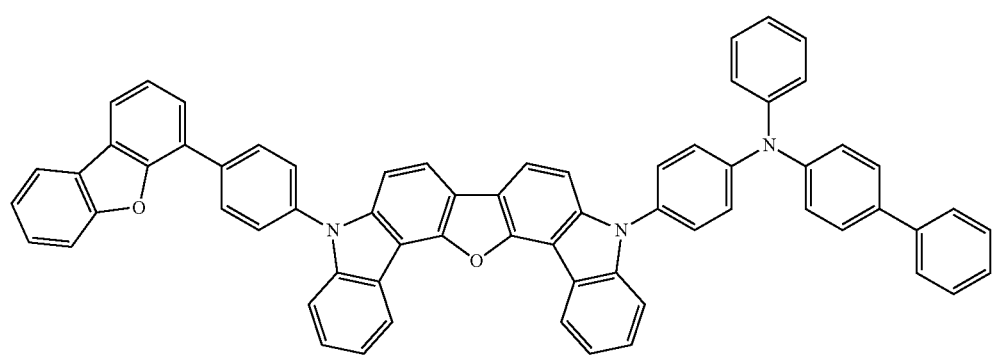
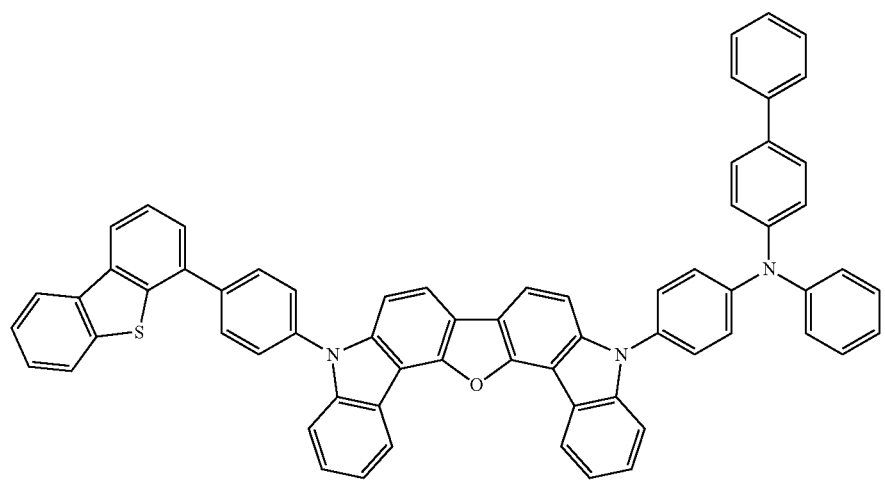

-continued
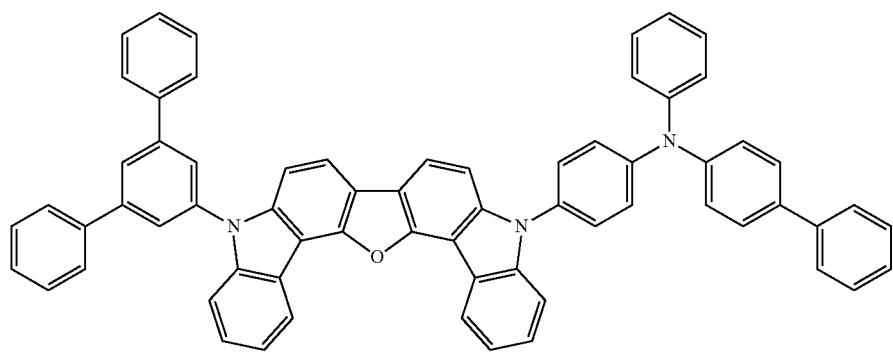
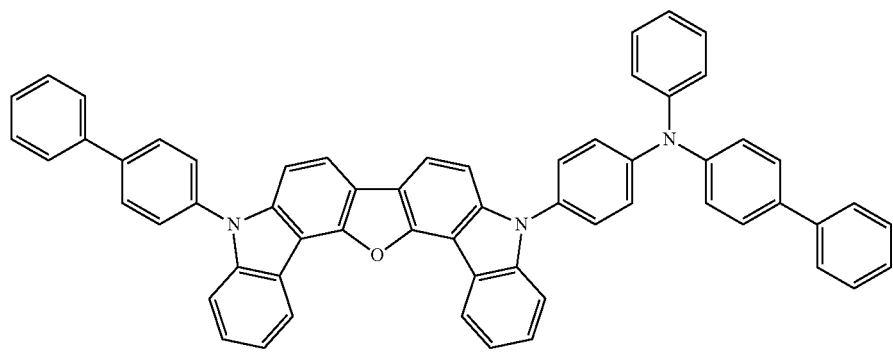
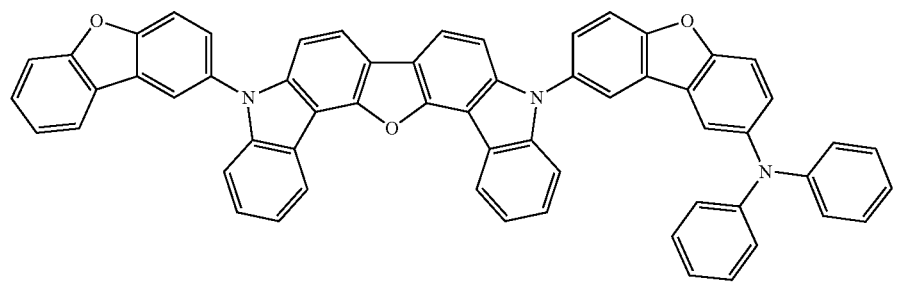
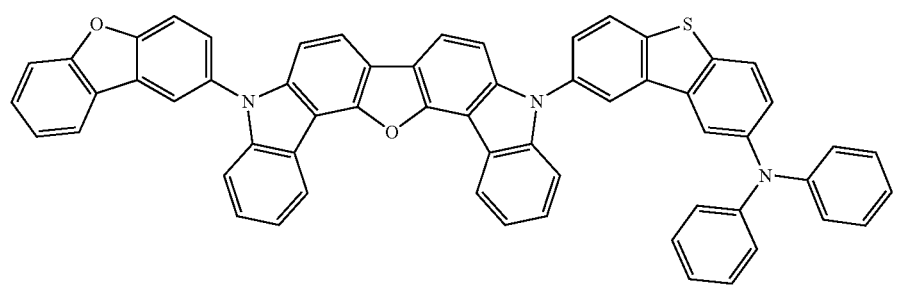
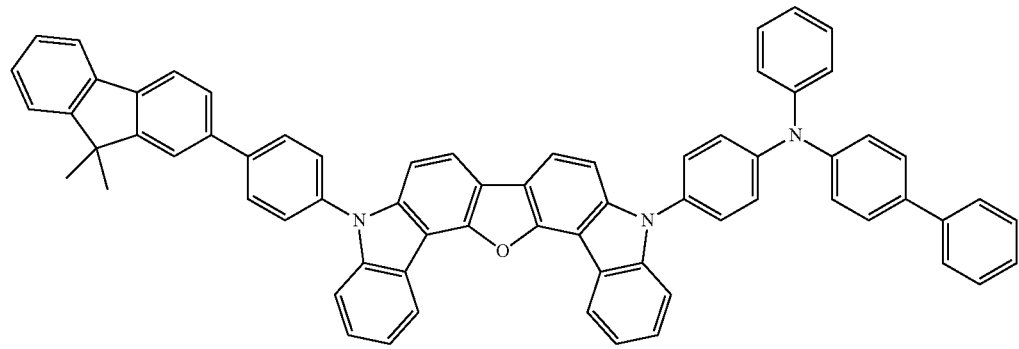

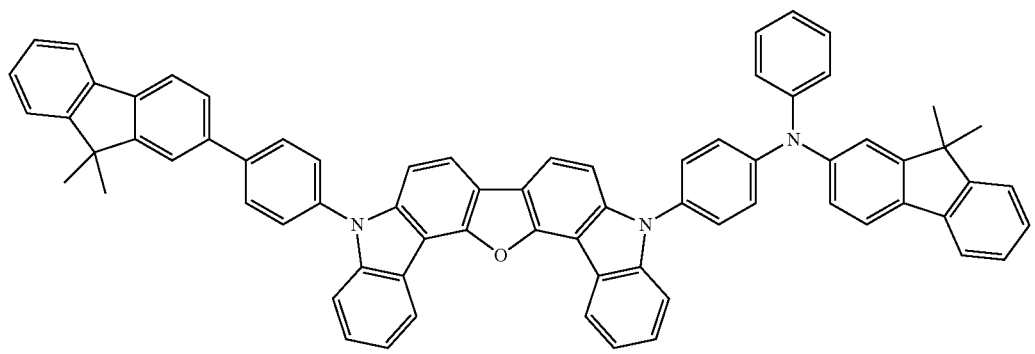
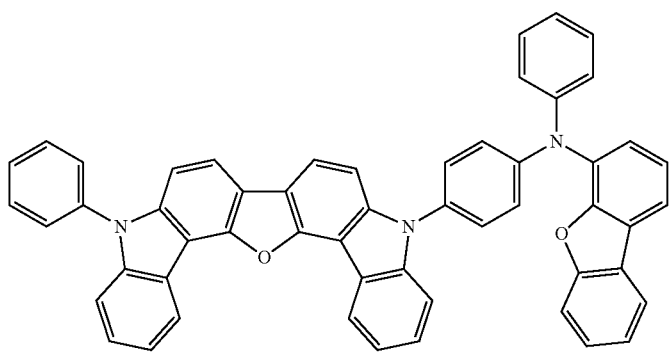
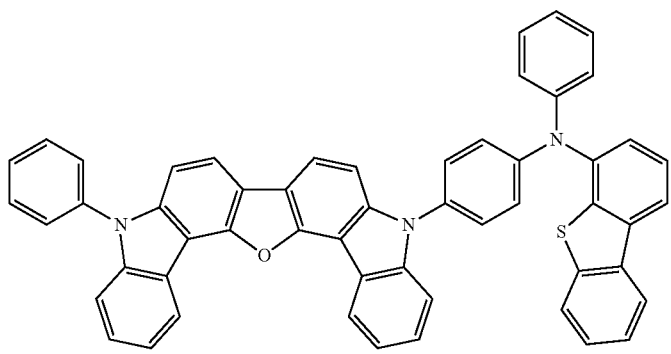
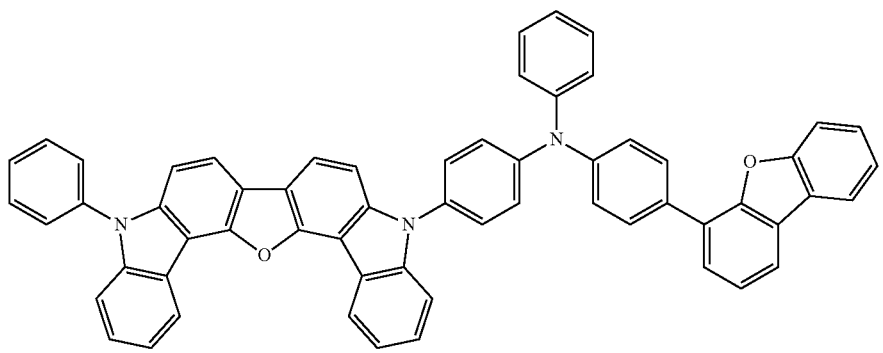

-continued
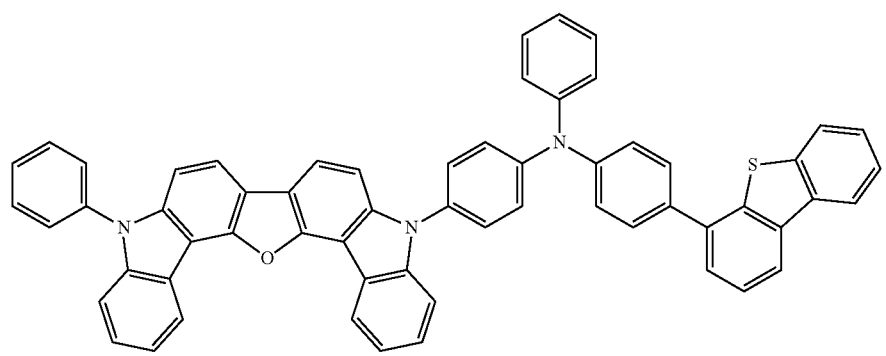
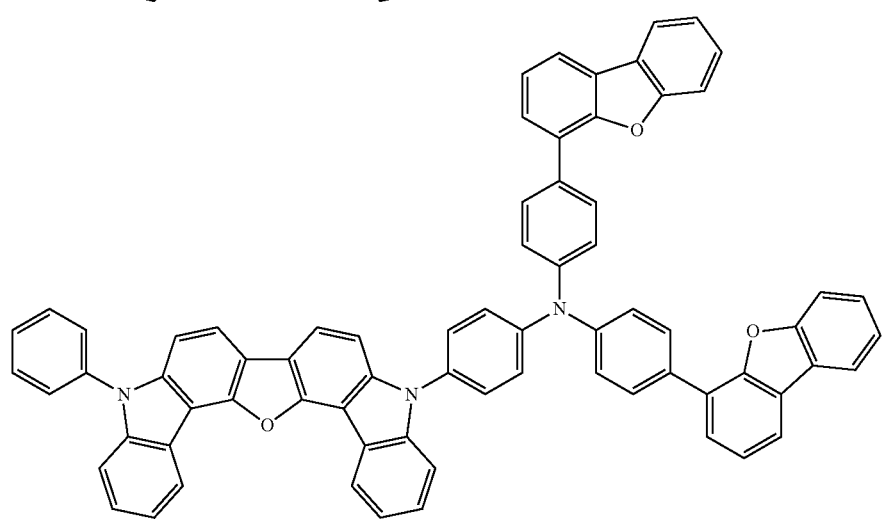
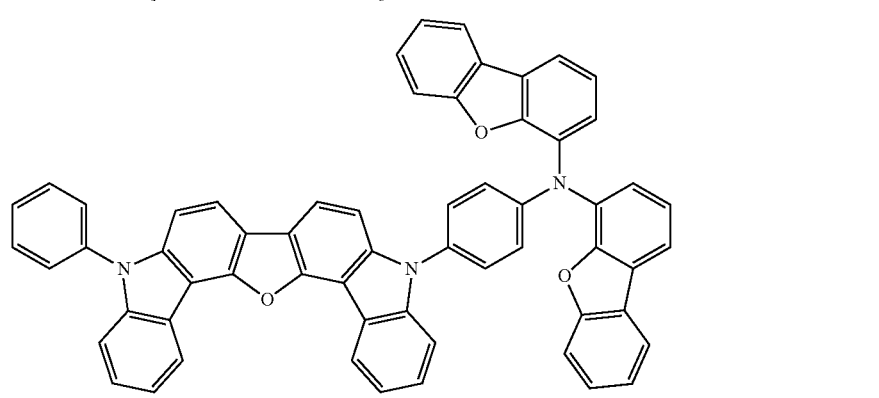
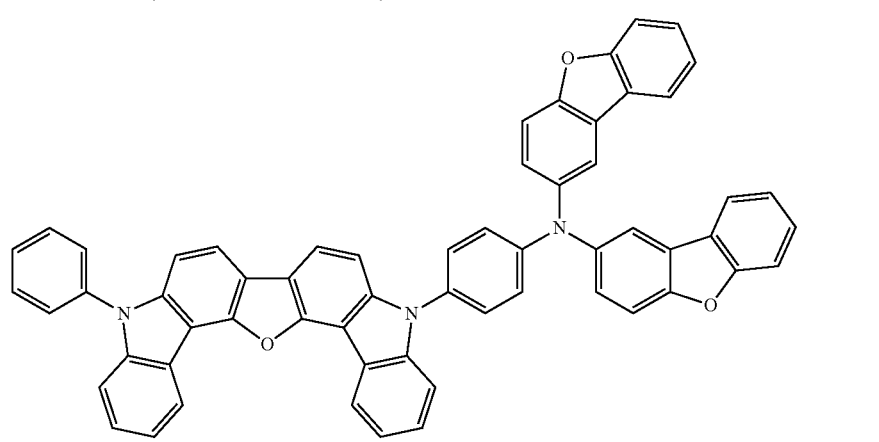

-continued
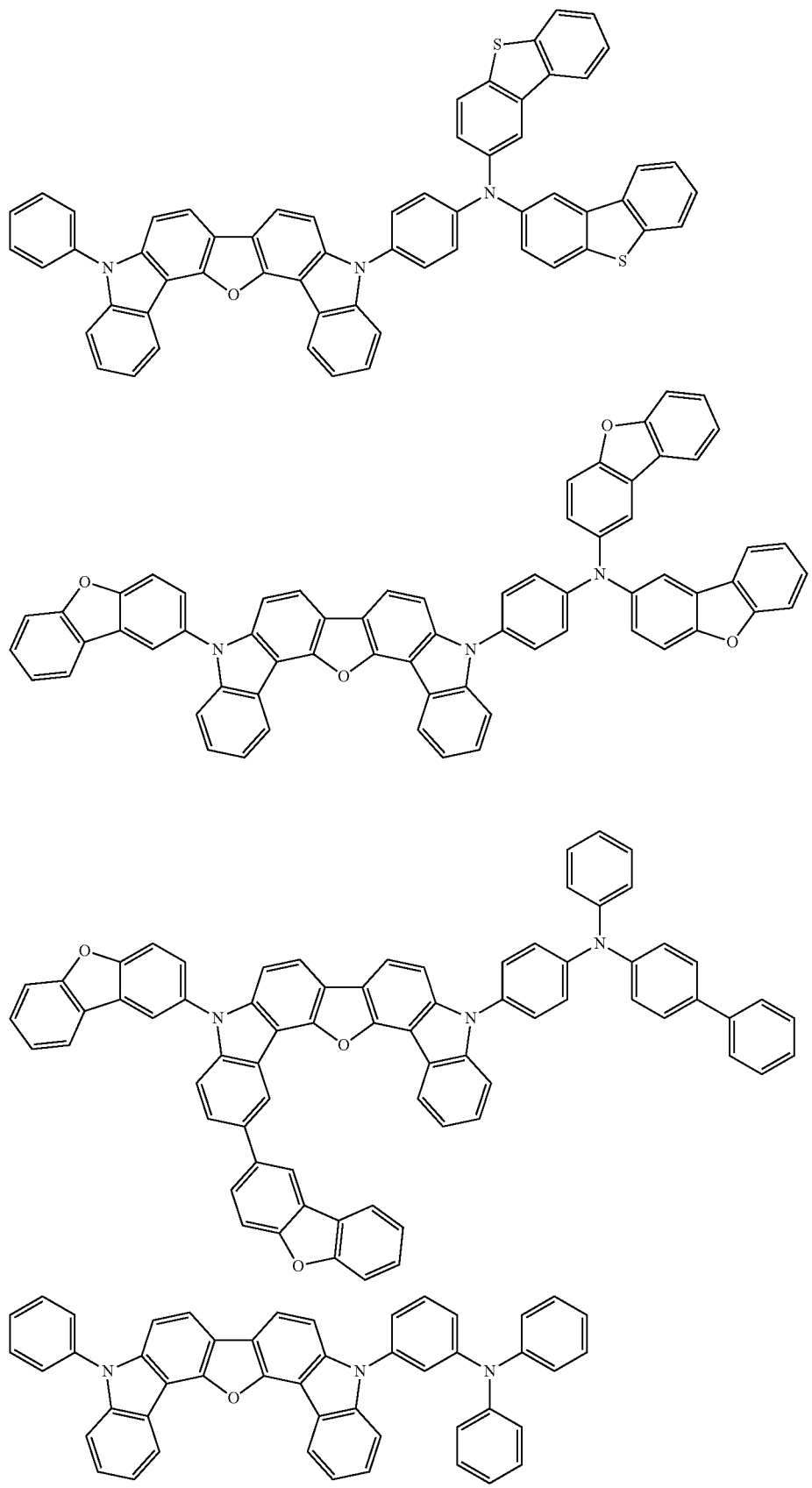

-continued
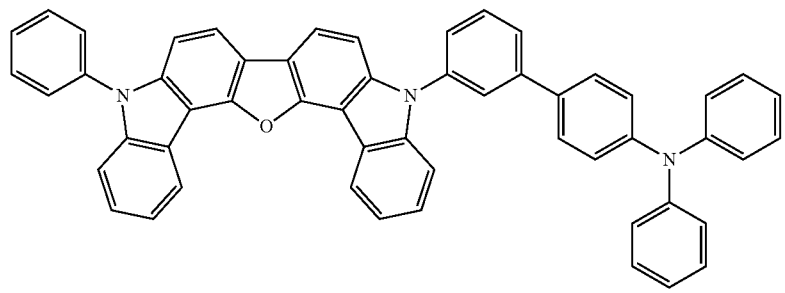
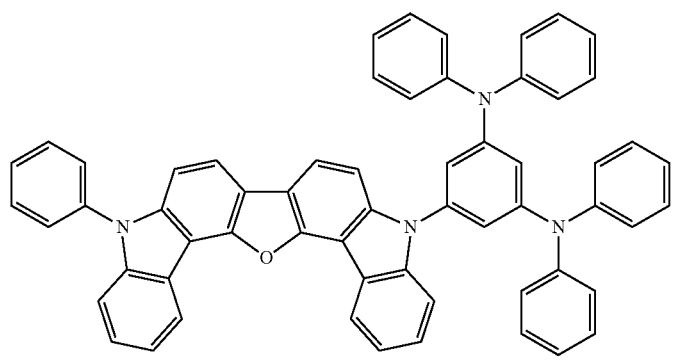
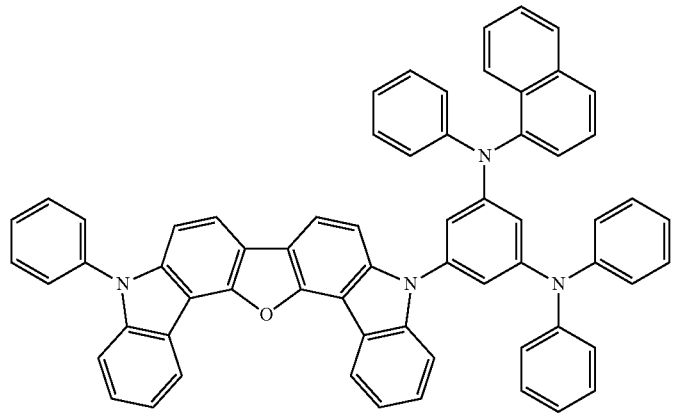
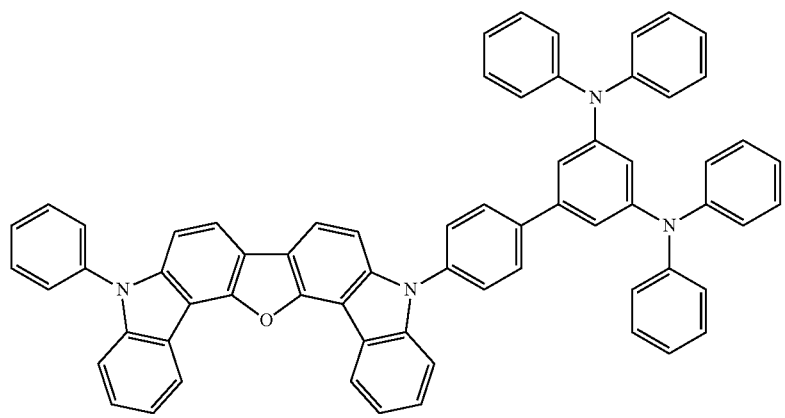

-continued
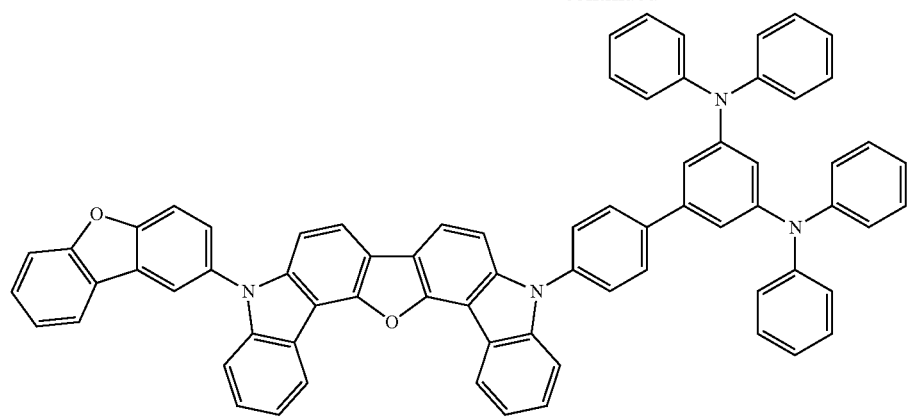
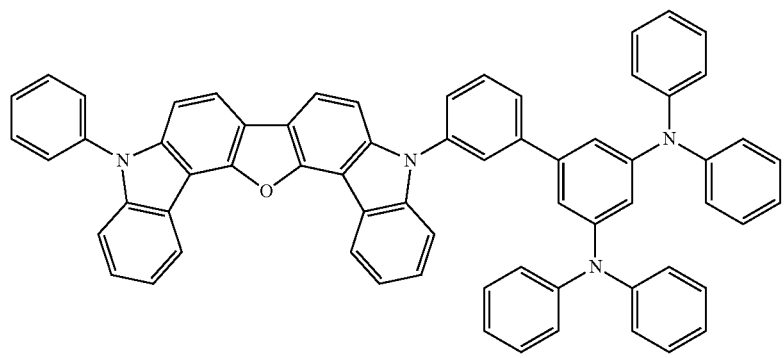
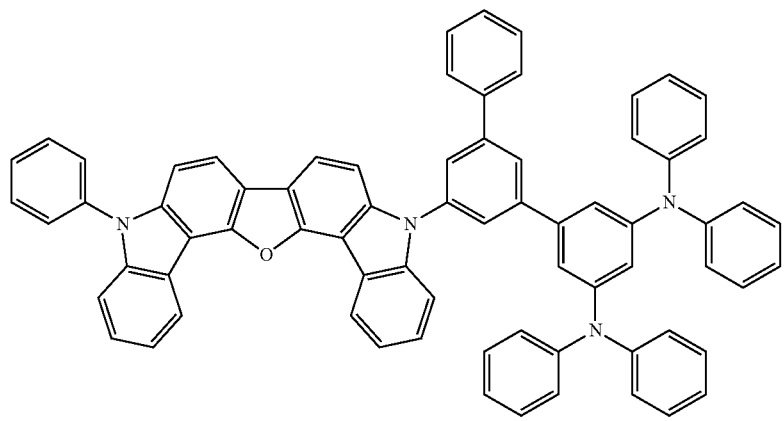
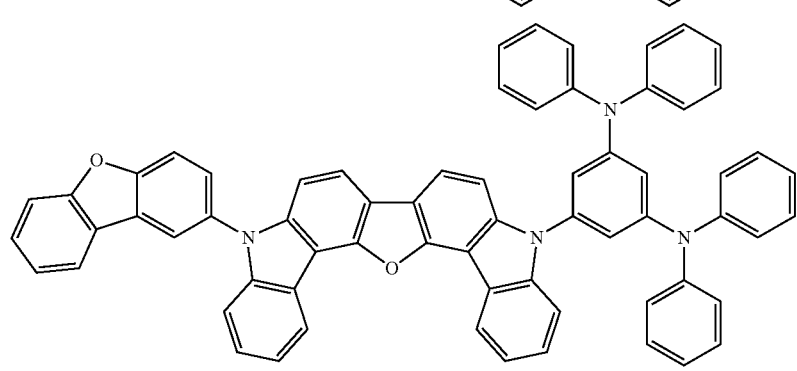

-continued
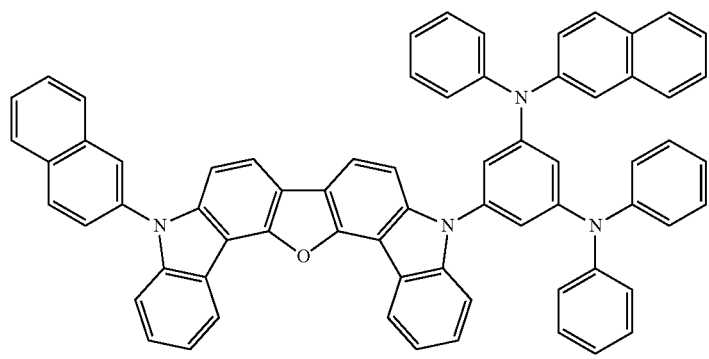
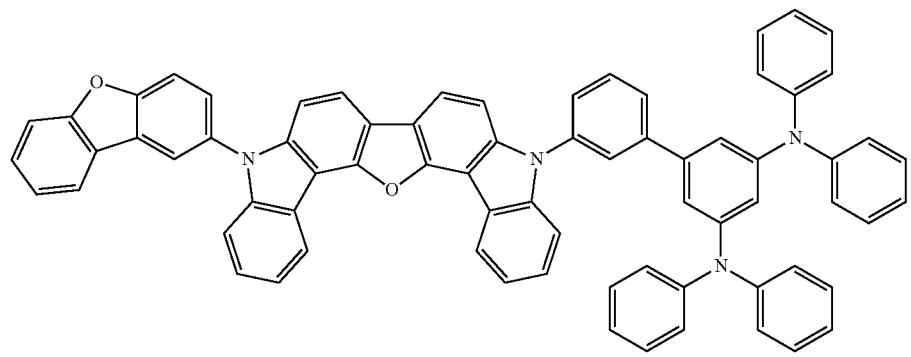
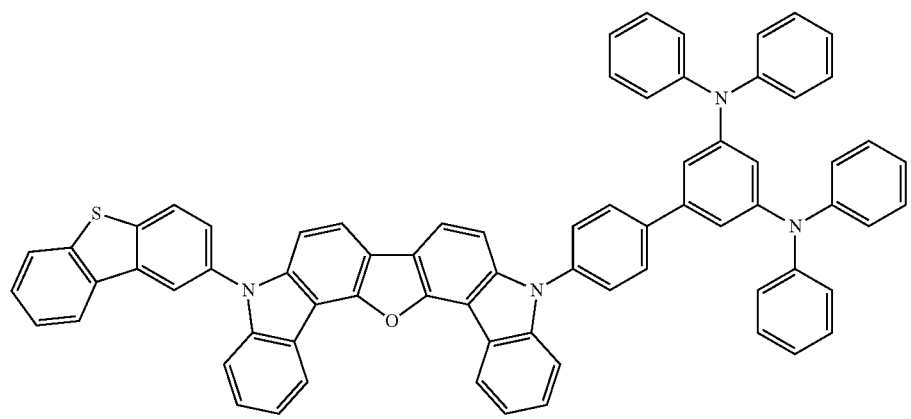
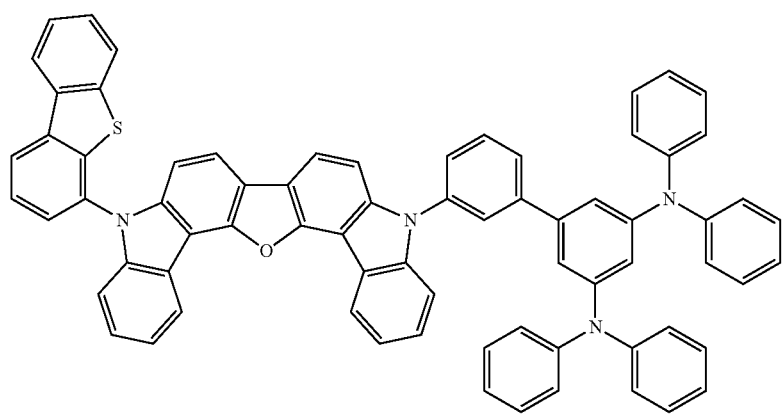

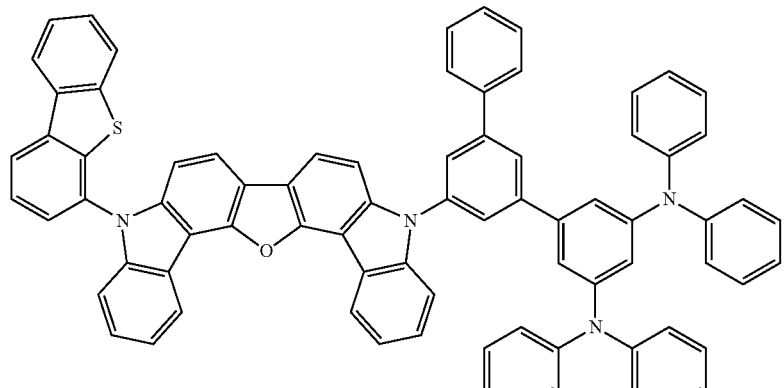
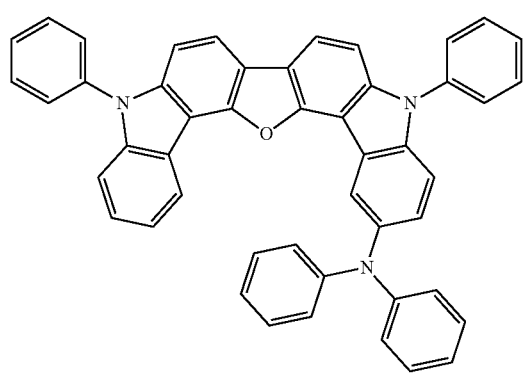
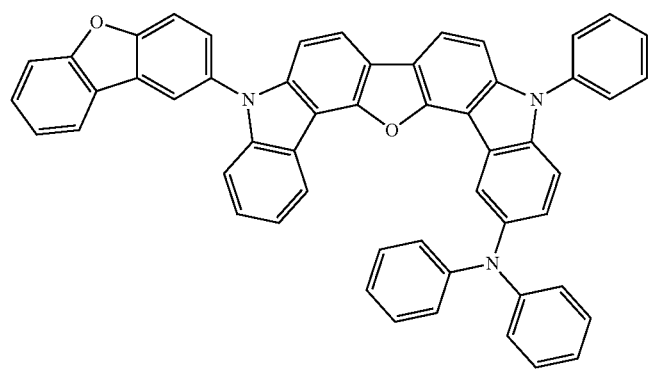
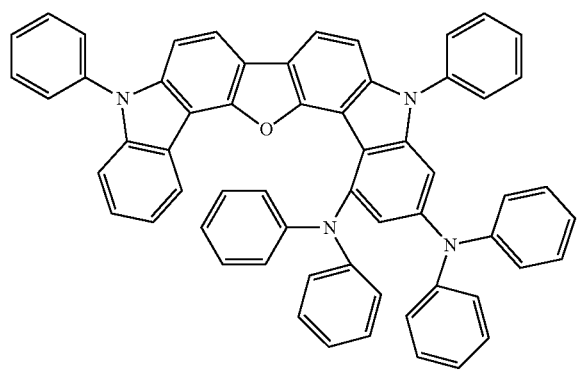

-continued
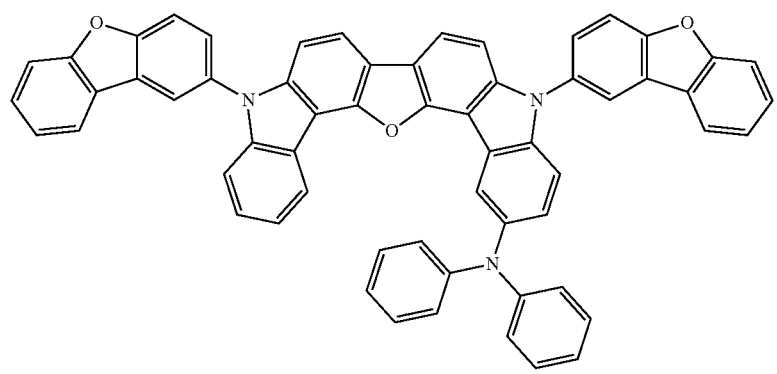
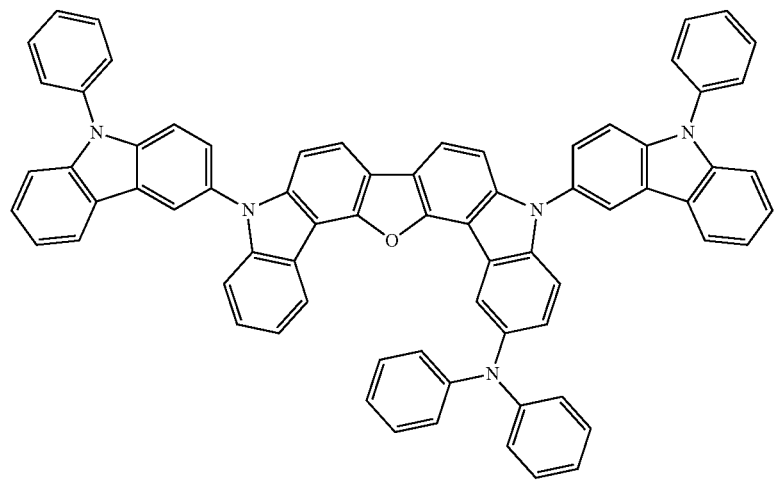
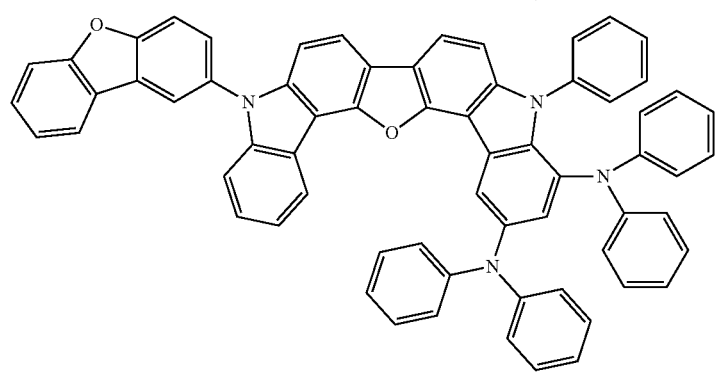
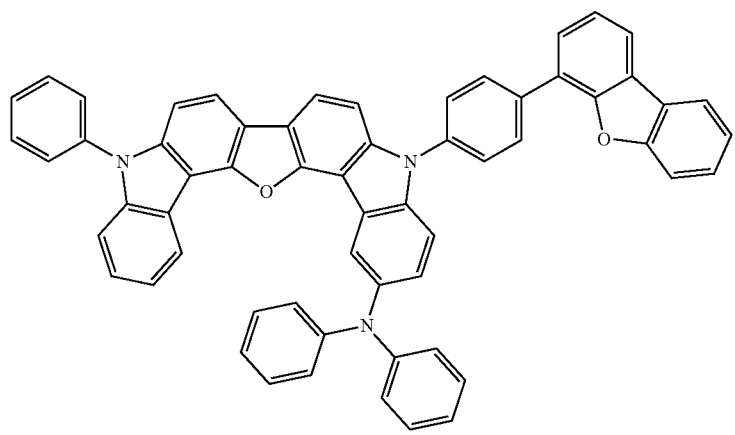

-continued
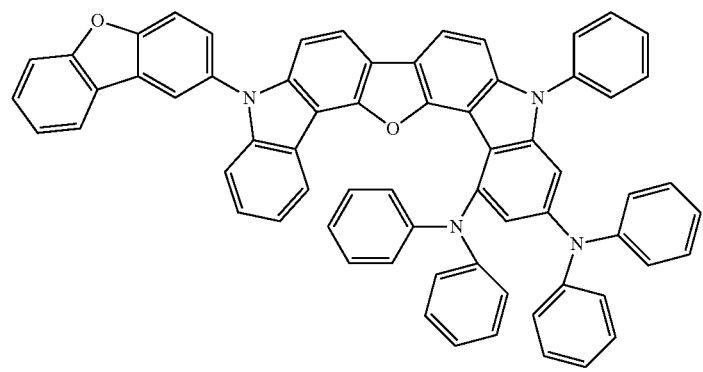
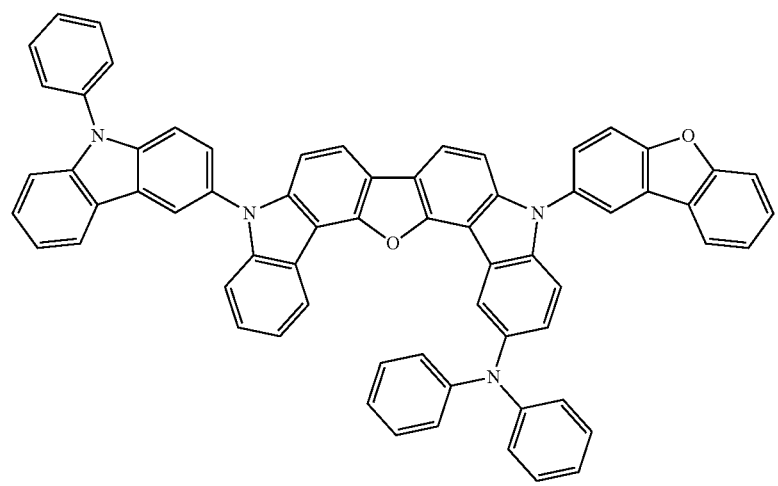
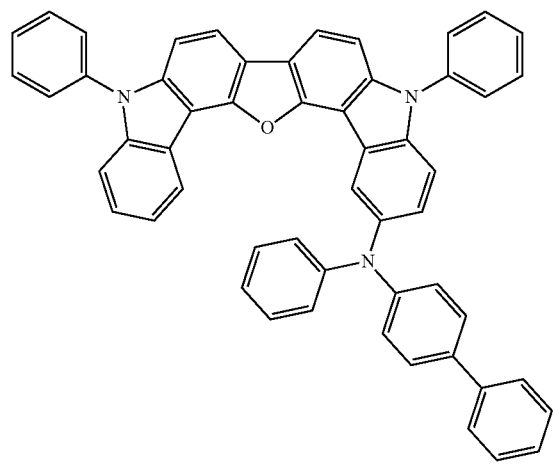

-continued
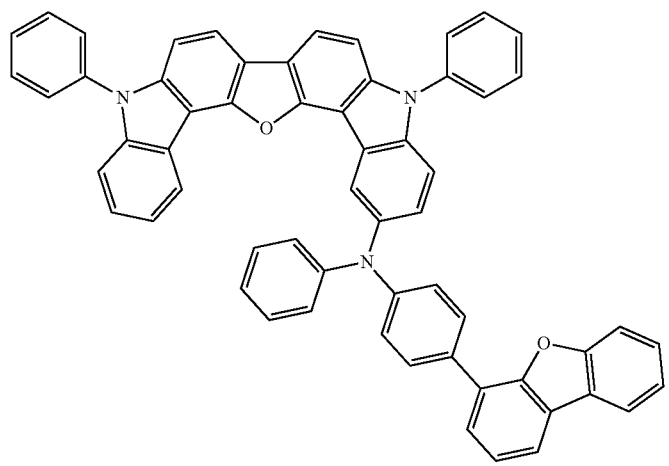
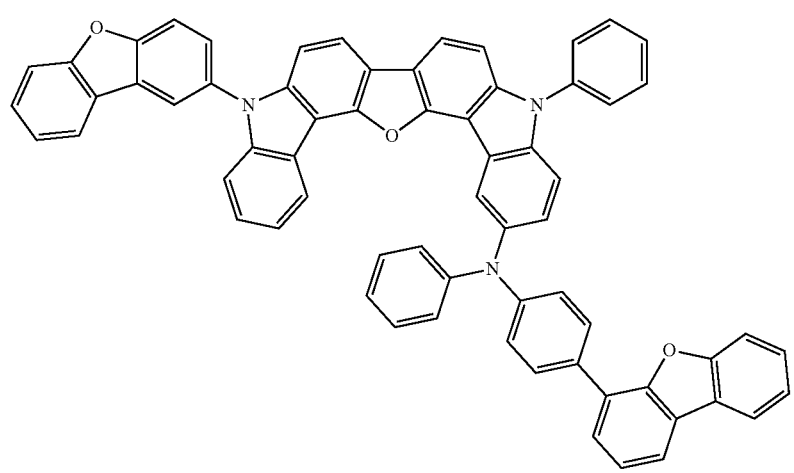
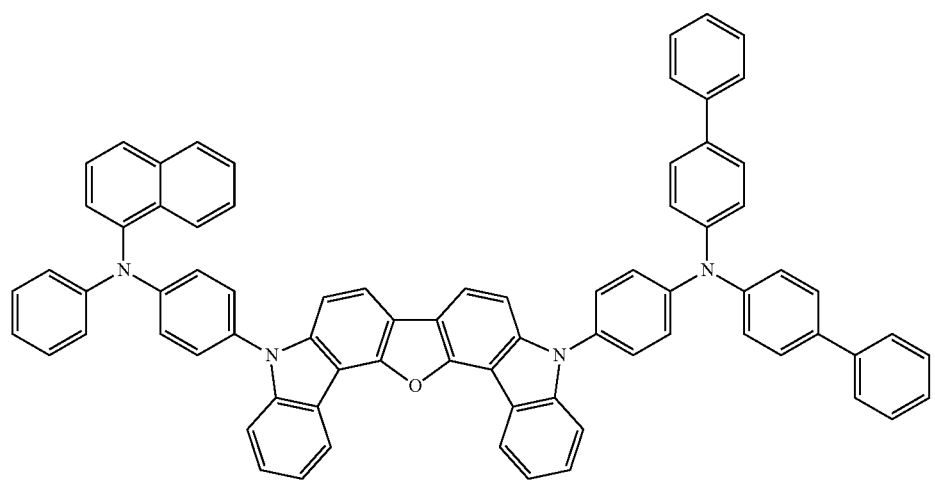

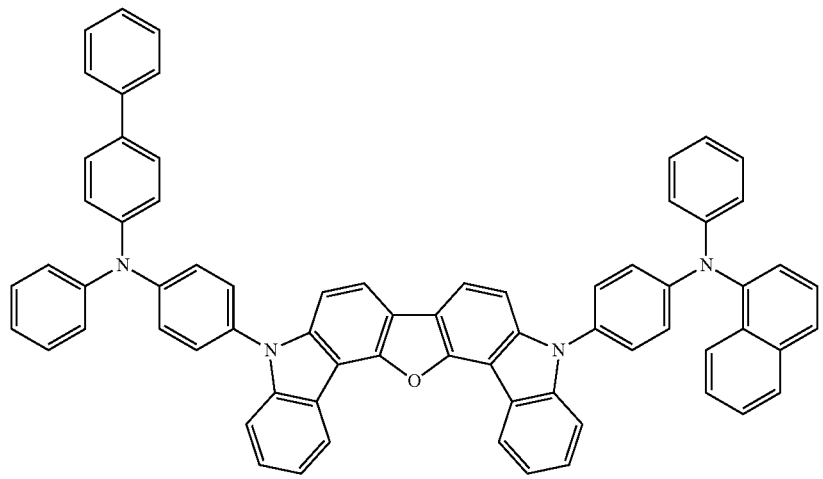
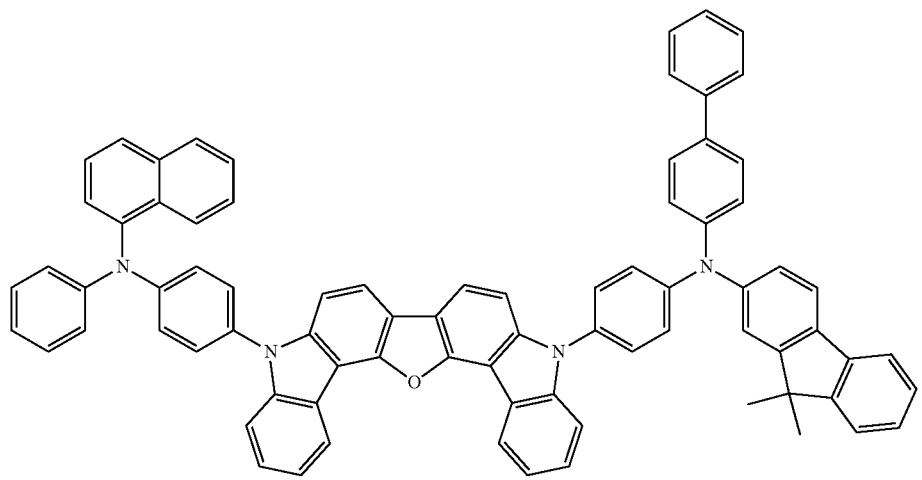
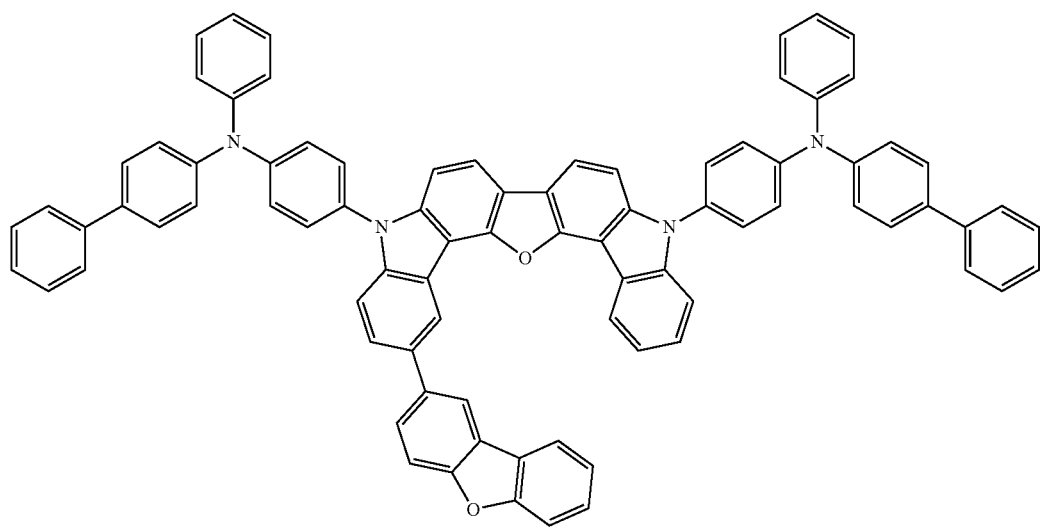

-continued
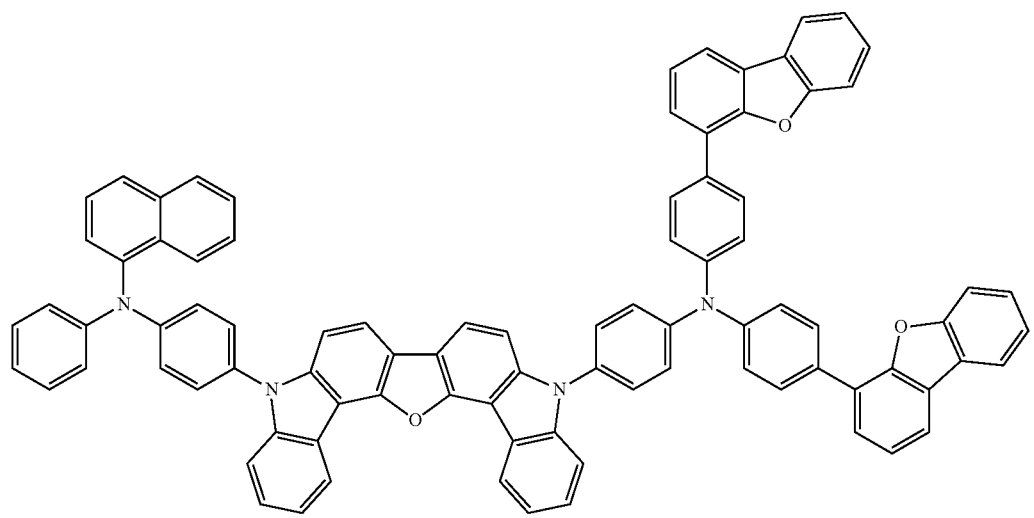
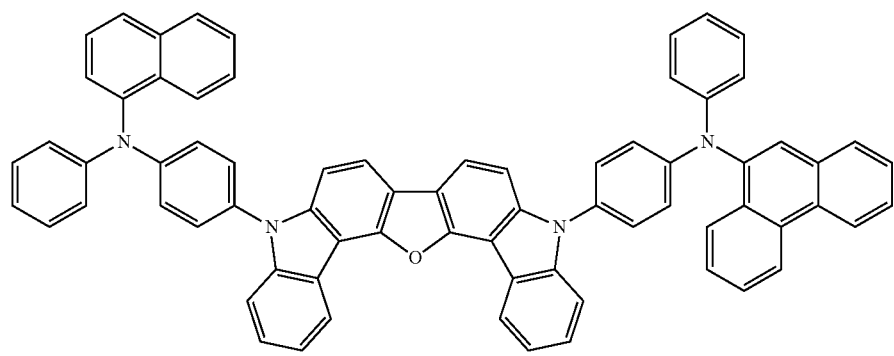
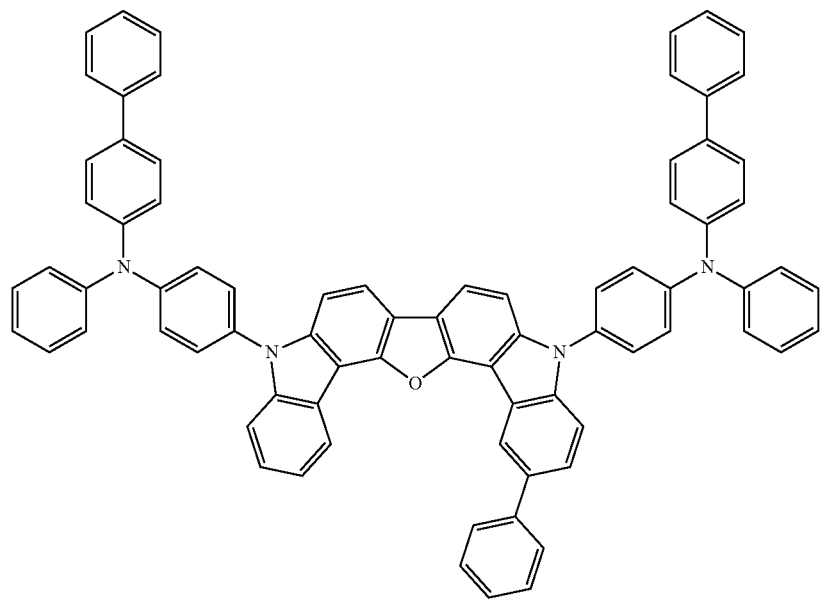

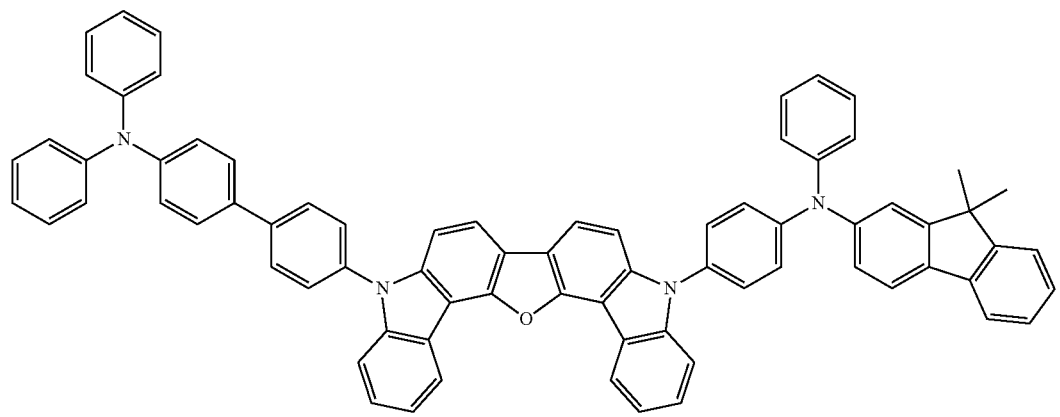
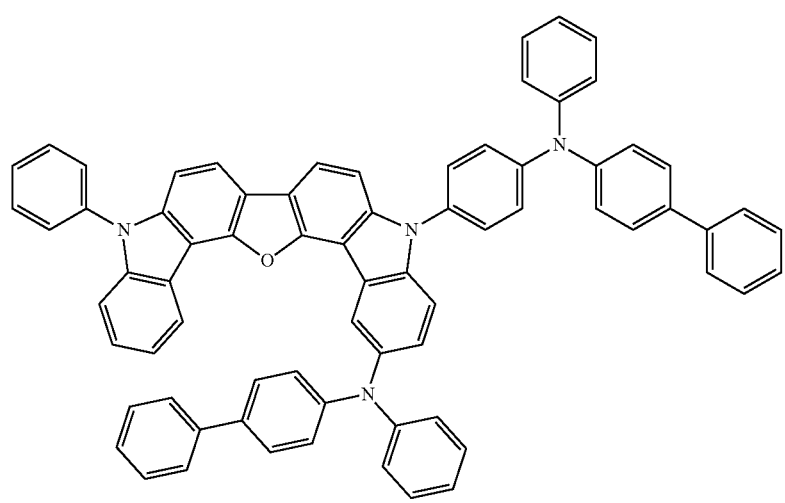
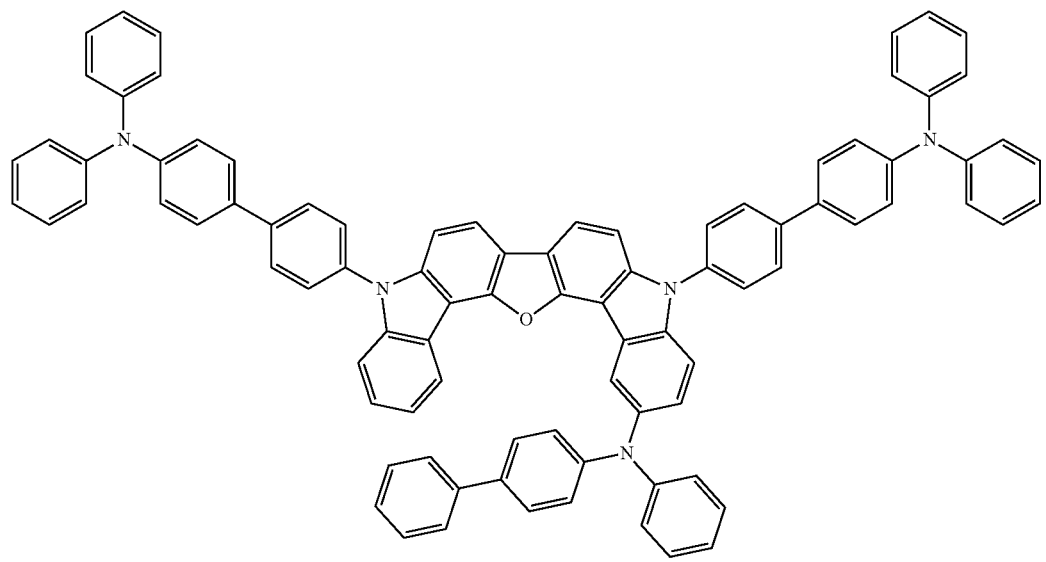

-continued
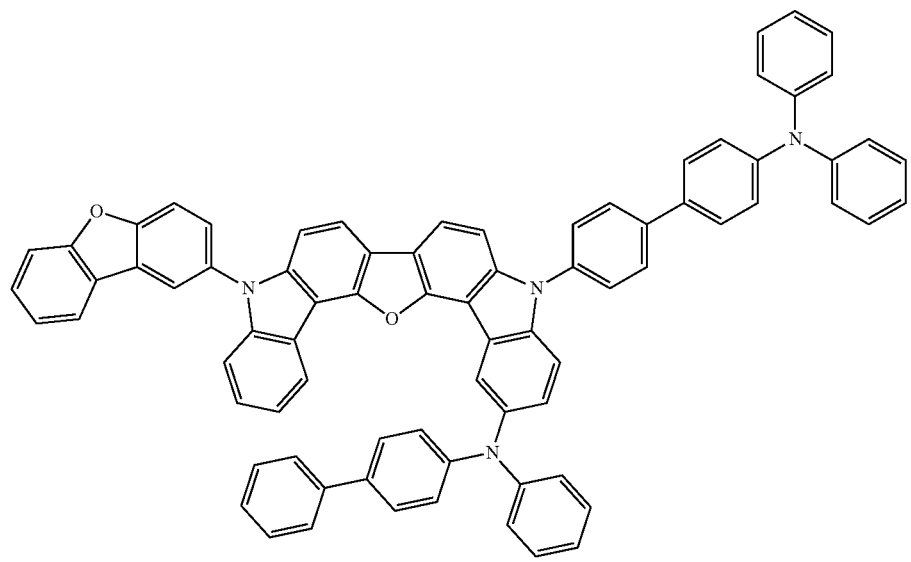
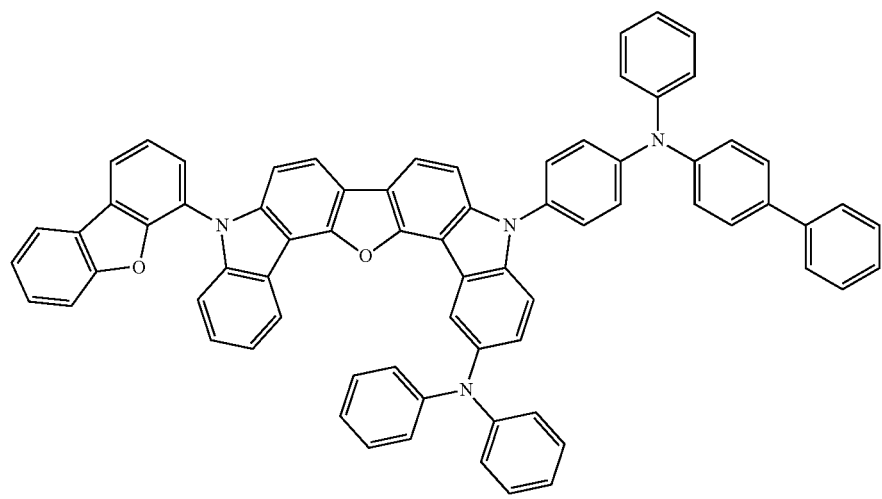
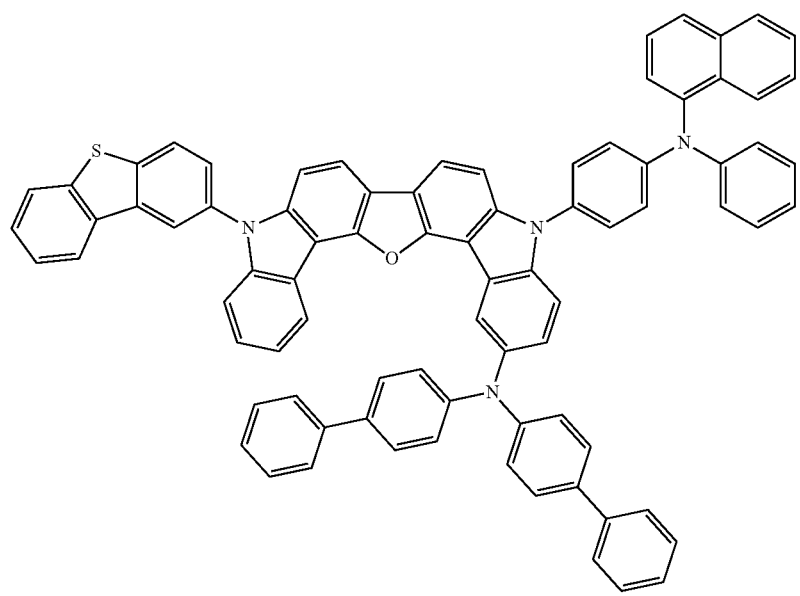

-continued
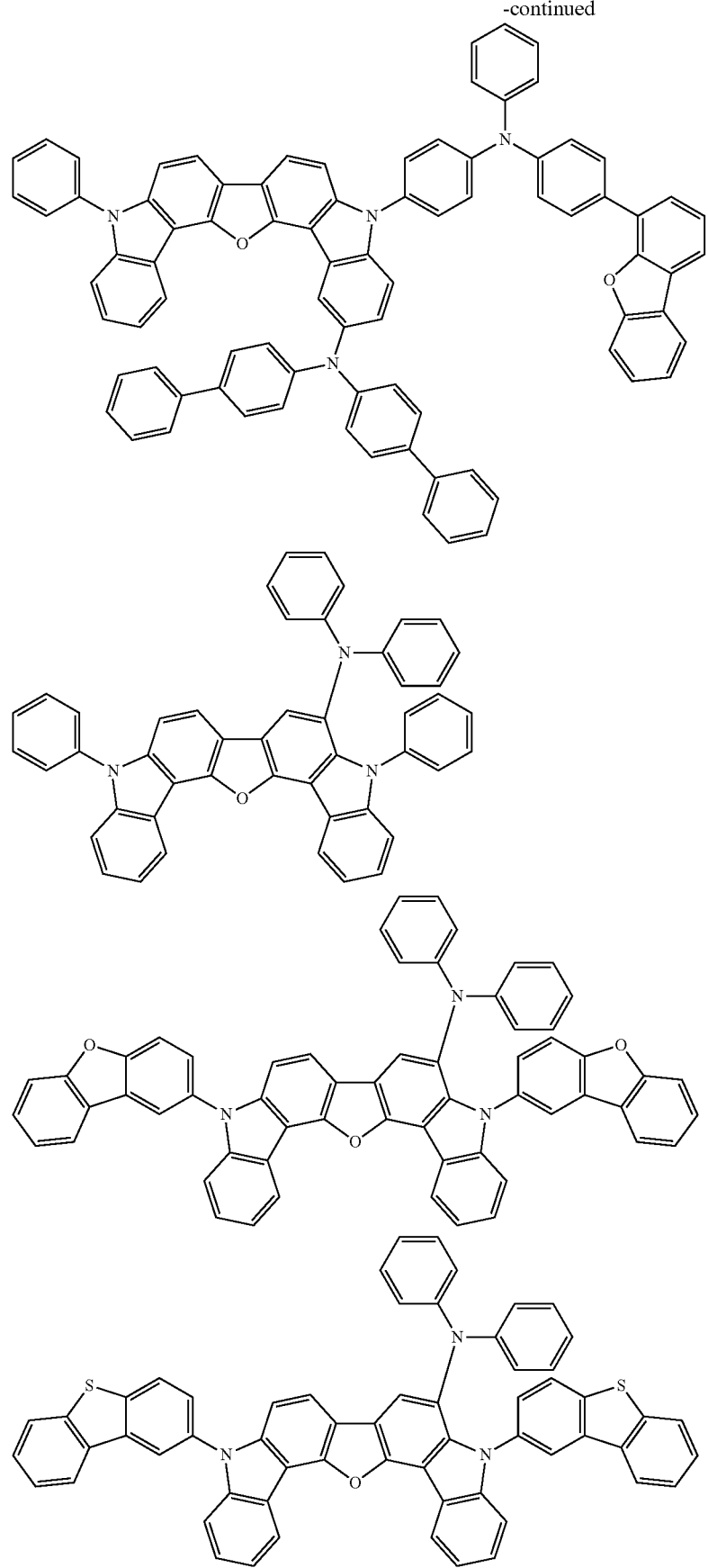

-continued
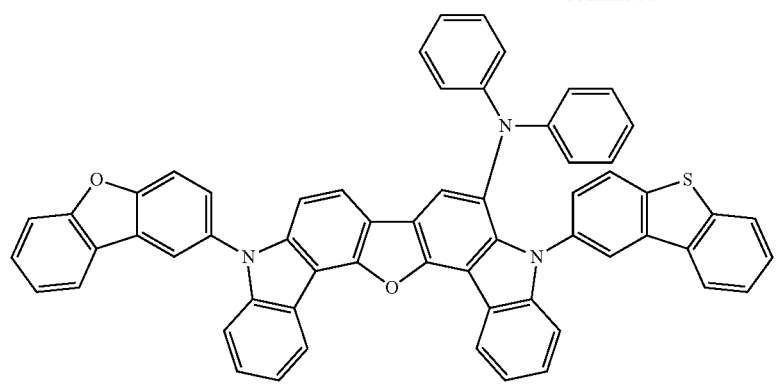
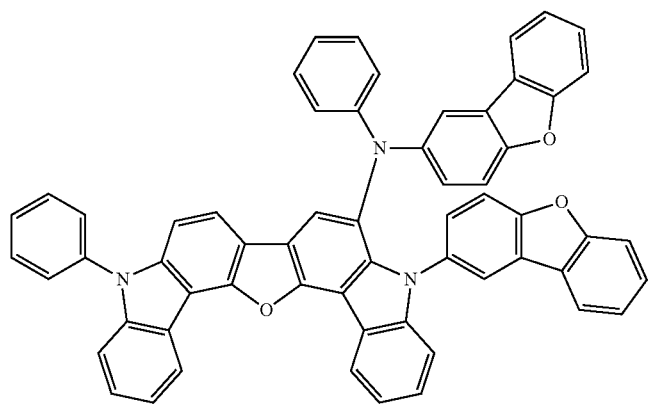
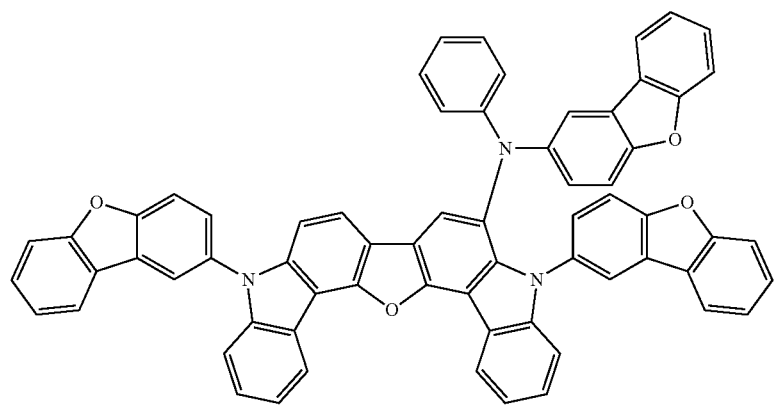
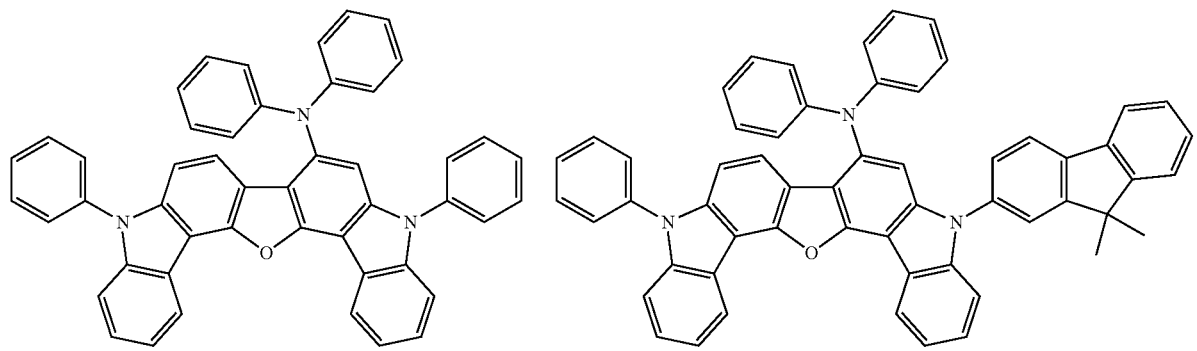

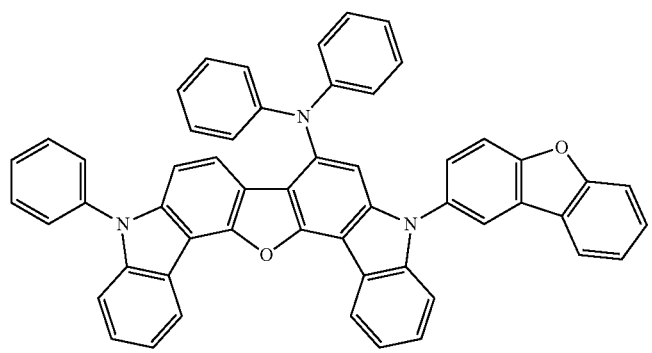
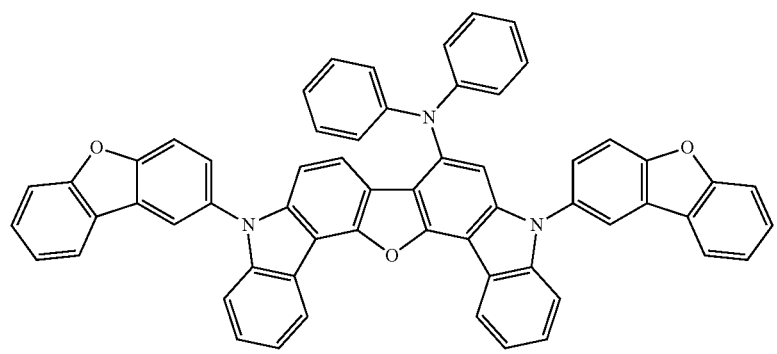
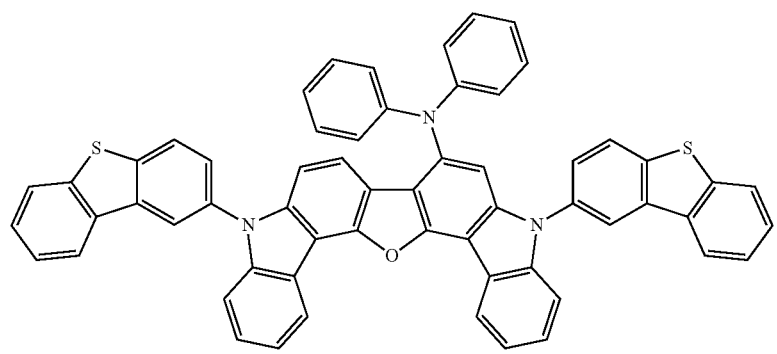
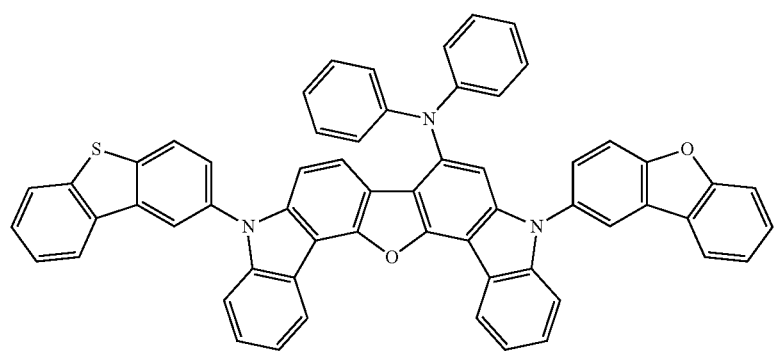

-continued
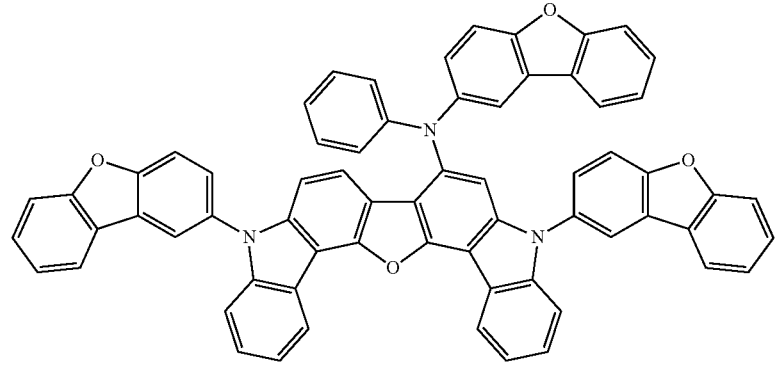
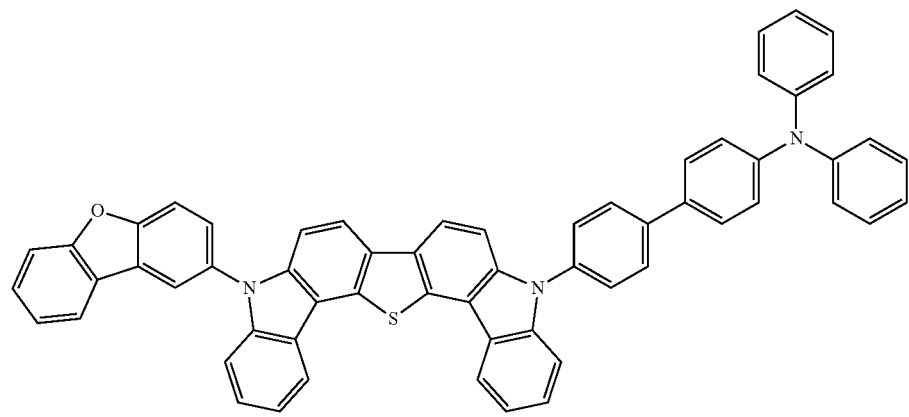
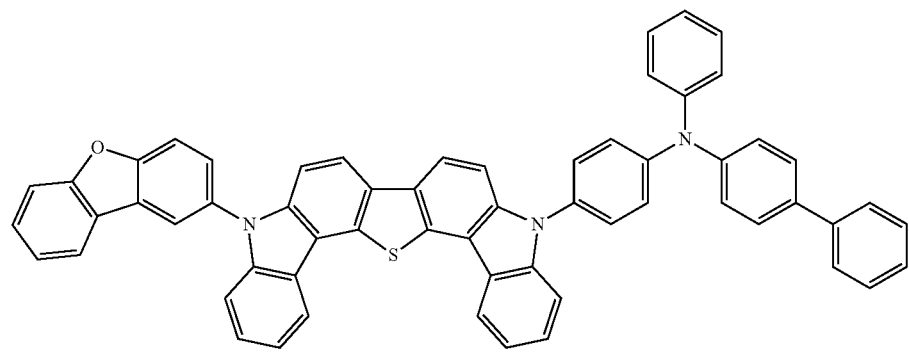
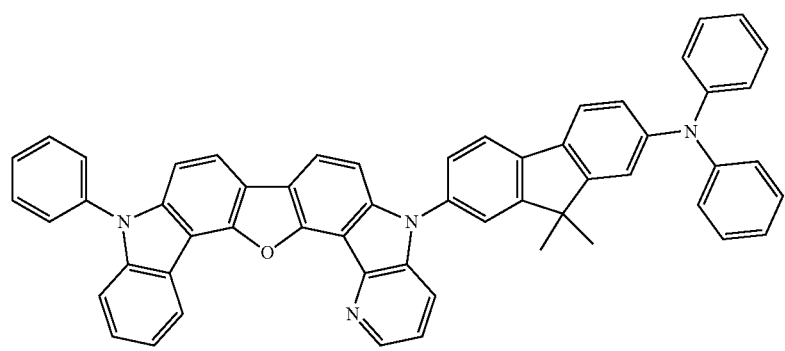

-continued
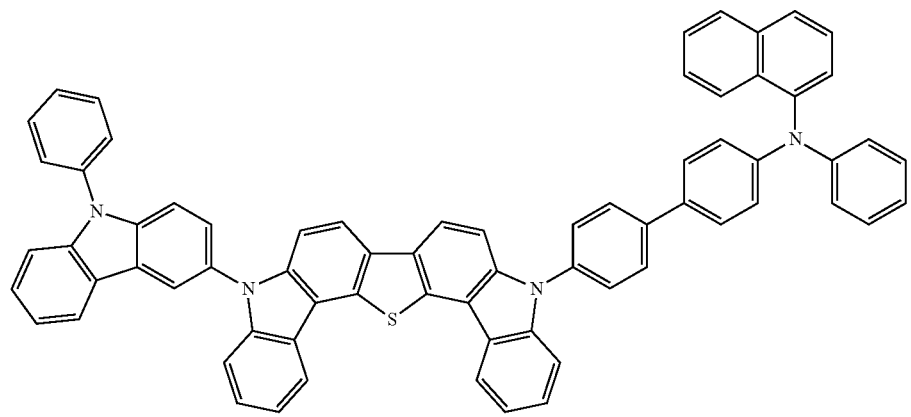
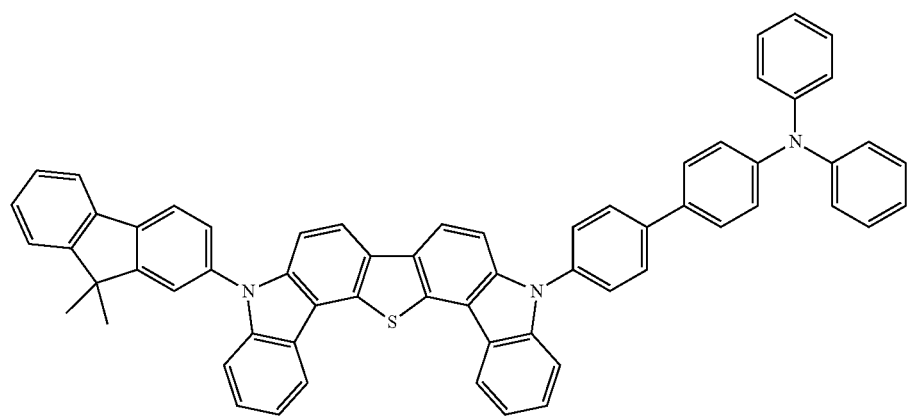
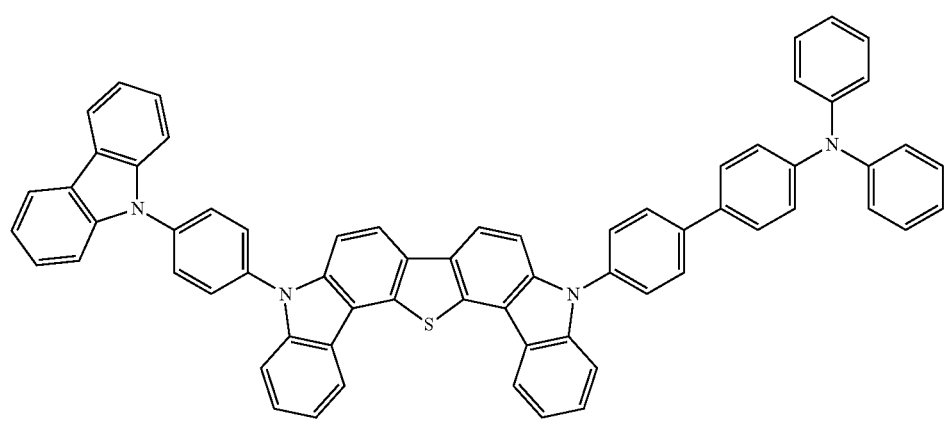
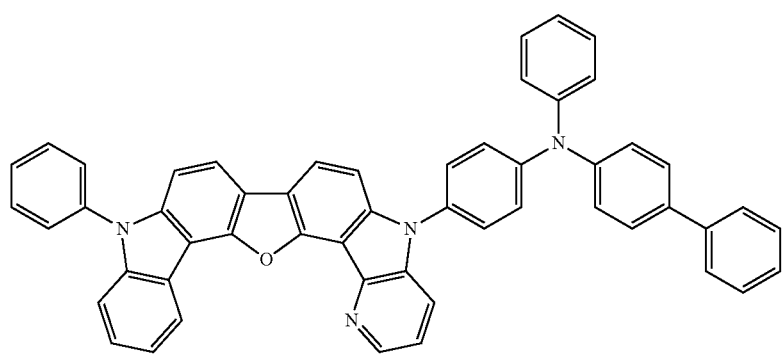

-continued
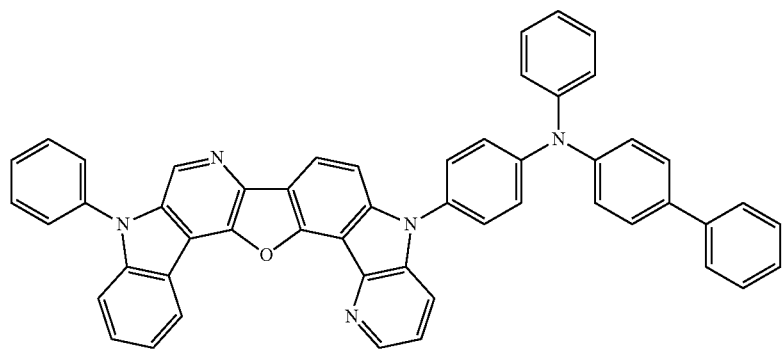
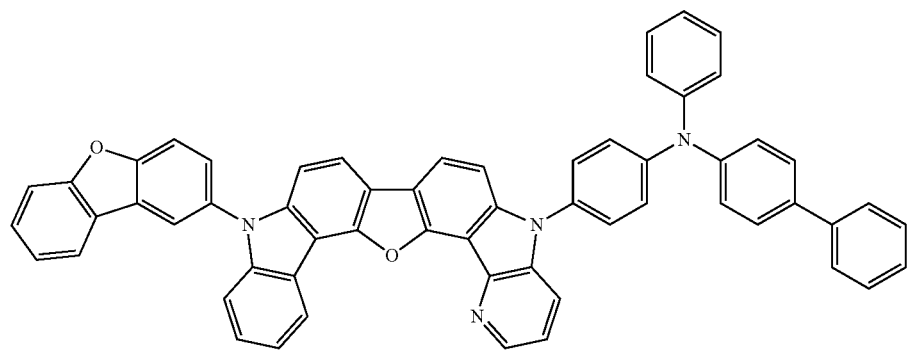
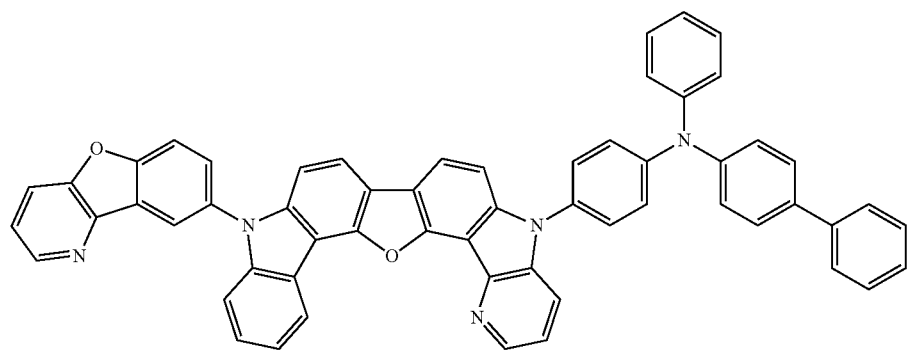
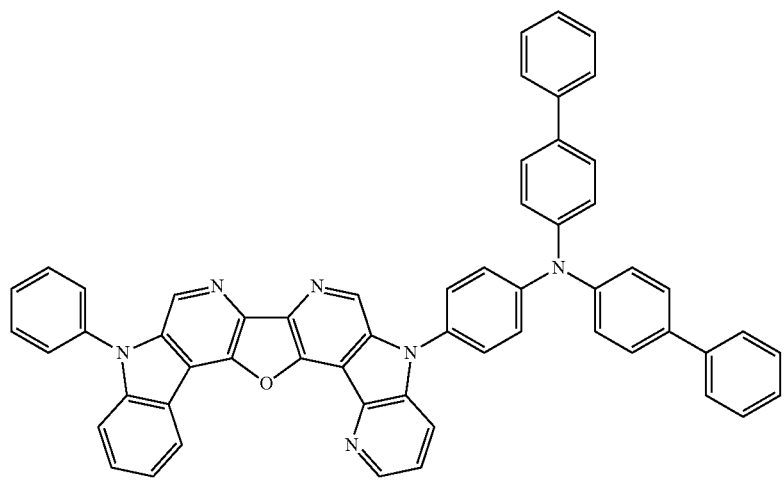

-continued
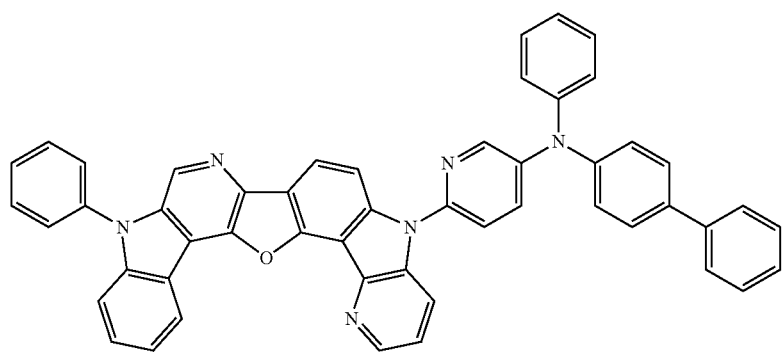
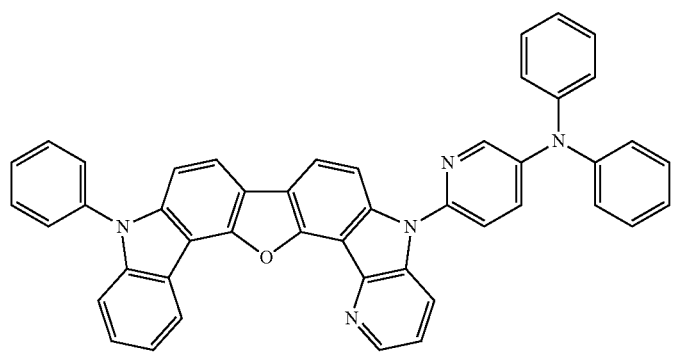
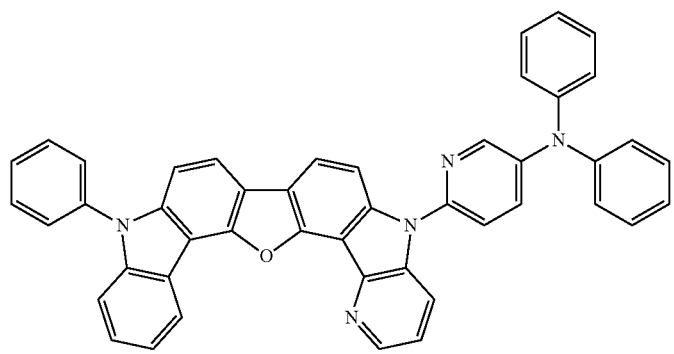
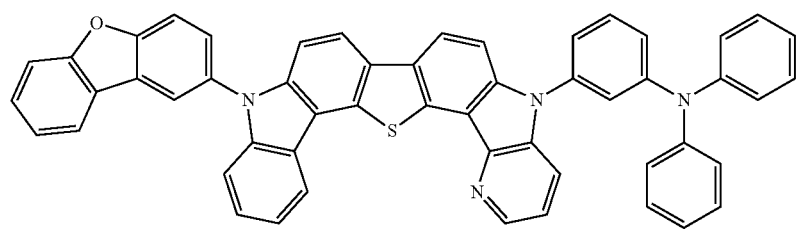

-continued
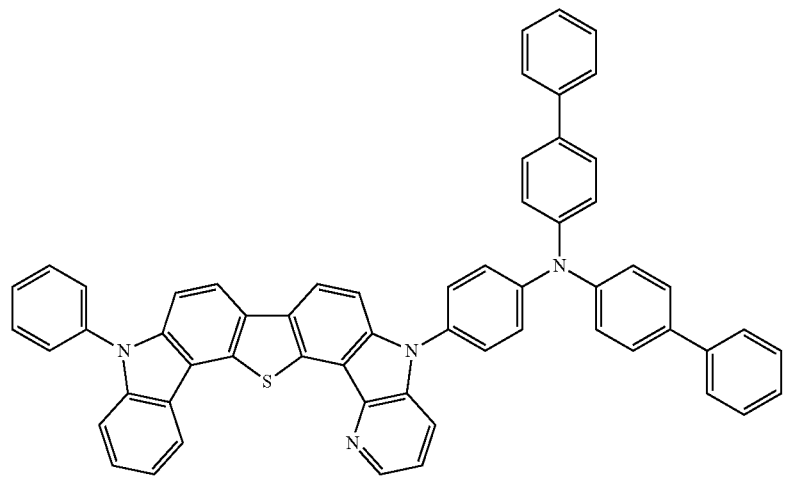
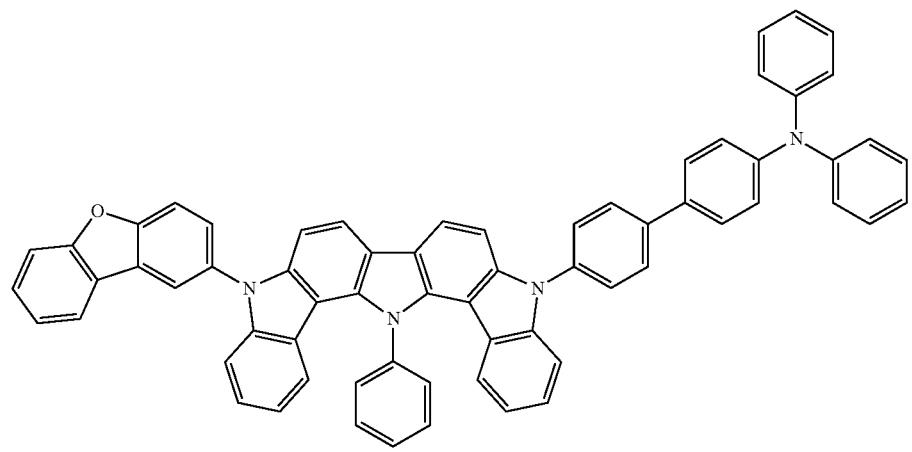
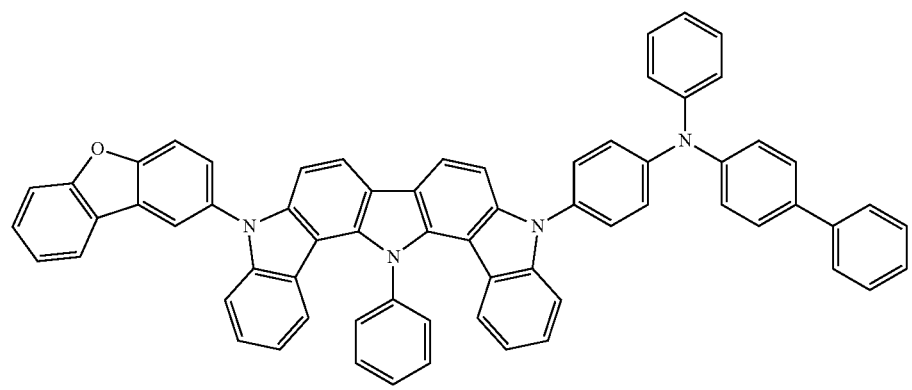
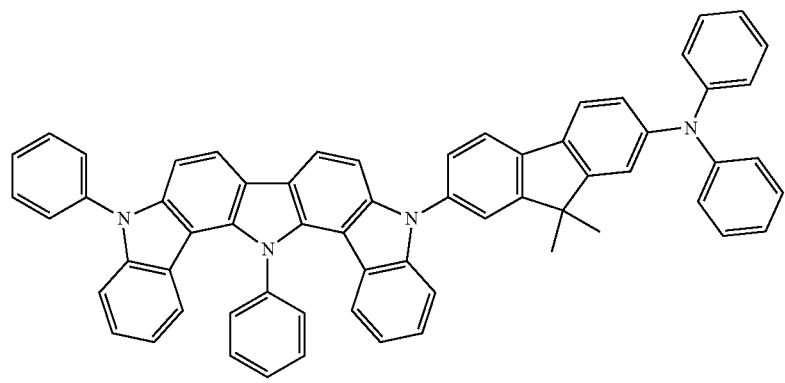

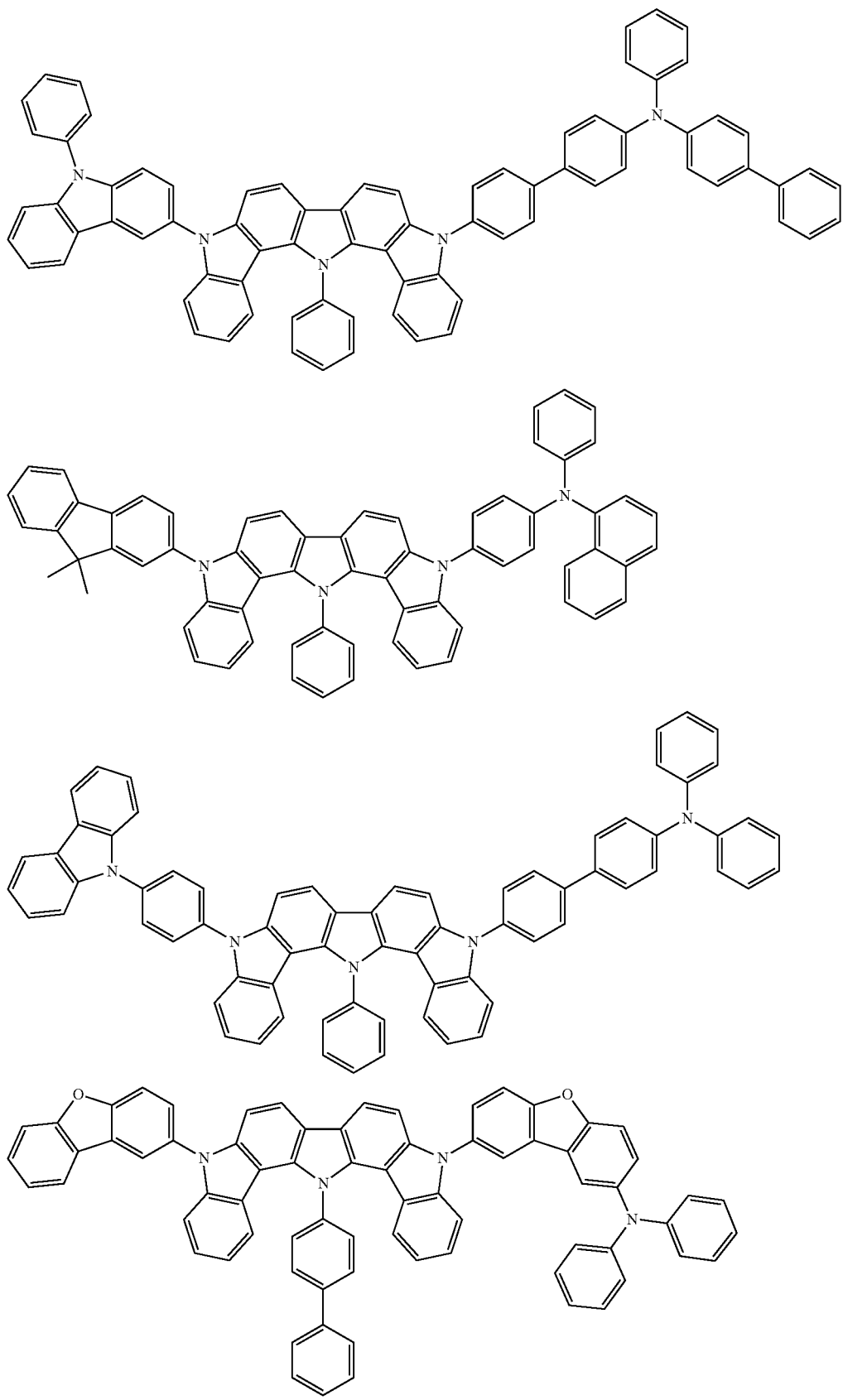

-continued
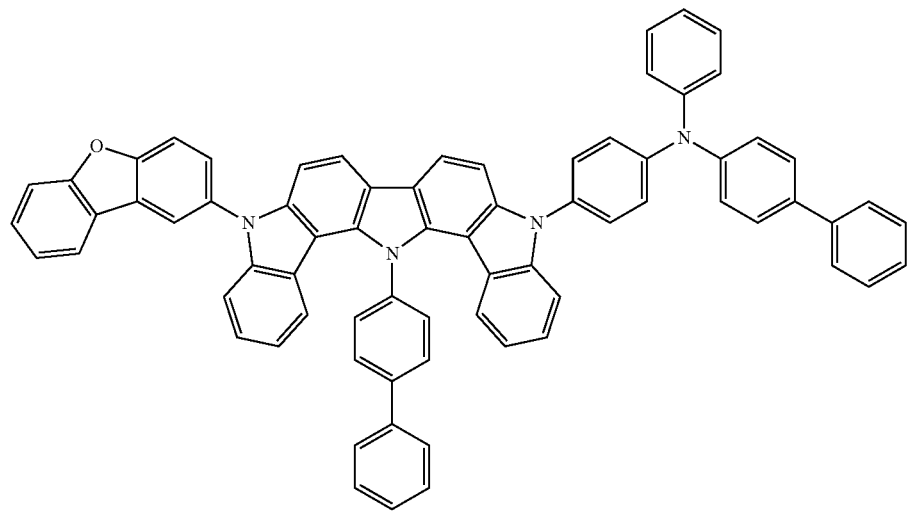
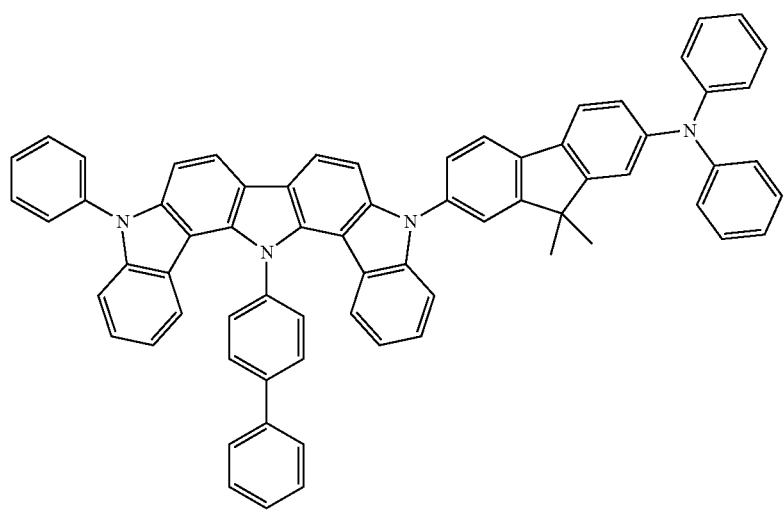
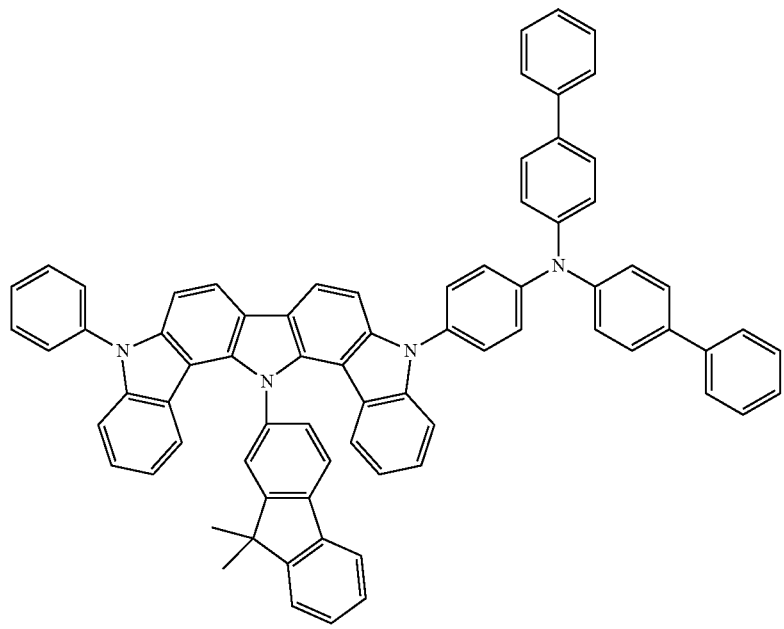

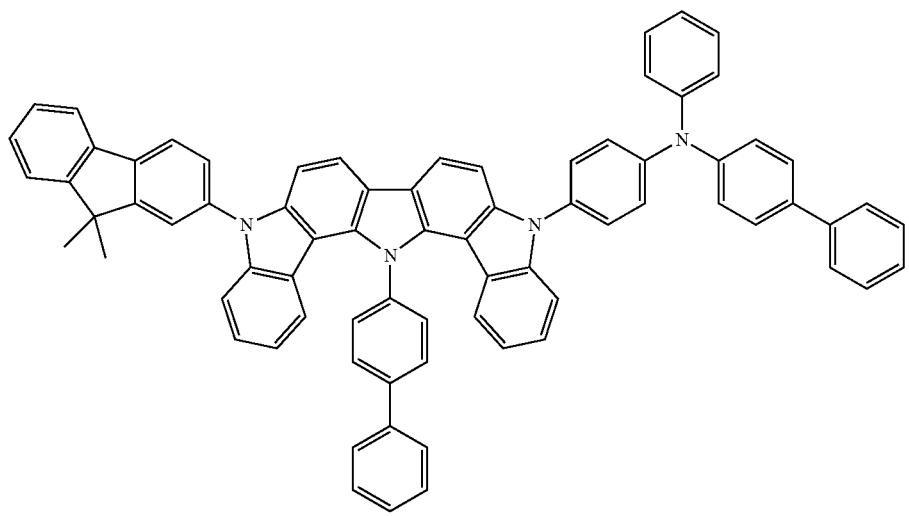
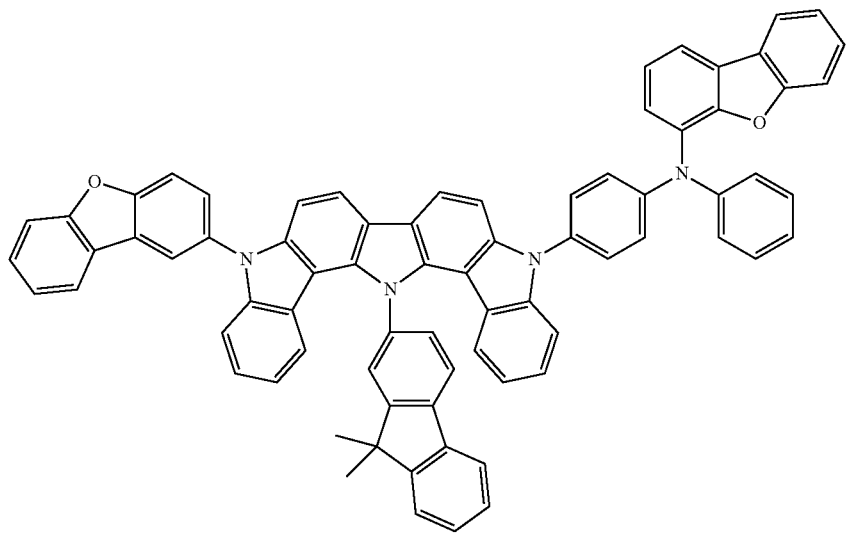
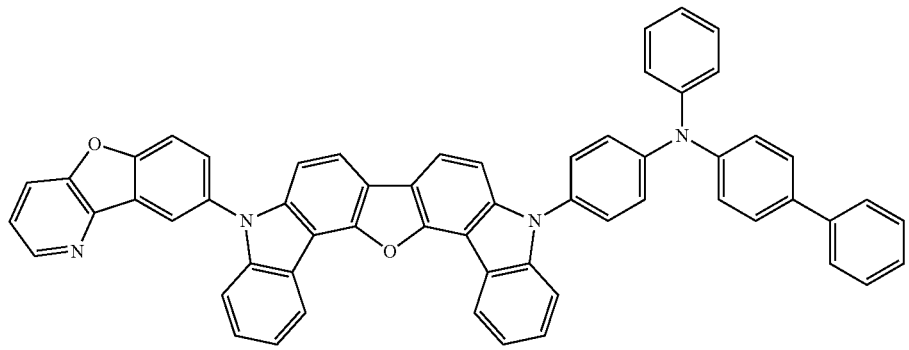

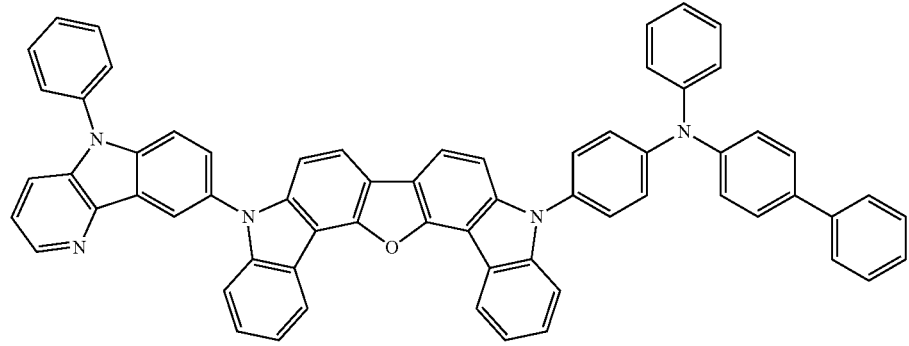
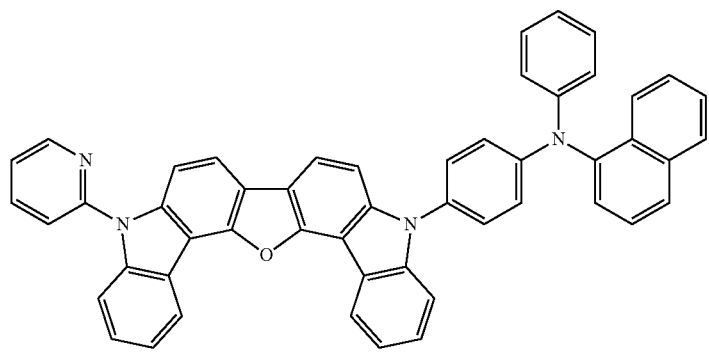
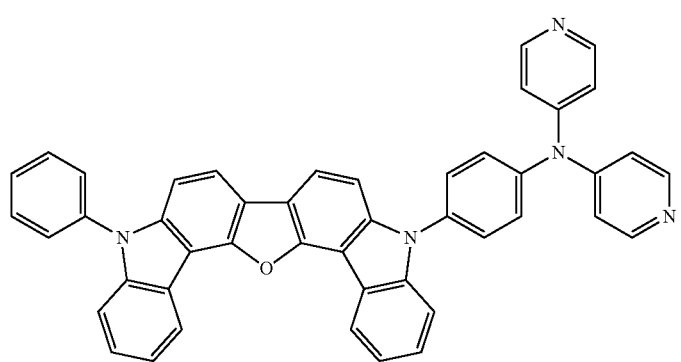
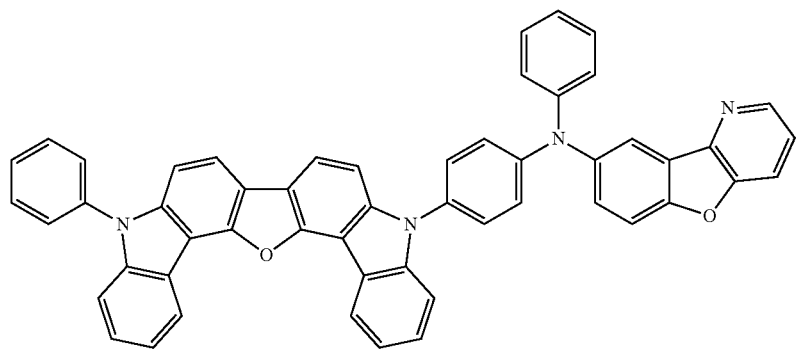

-continued
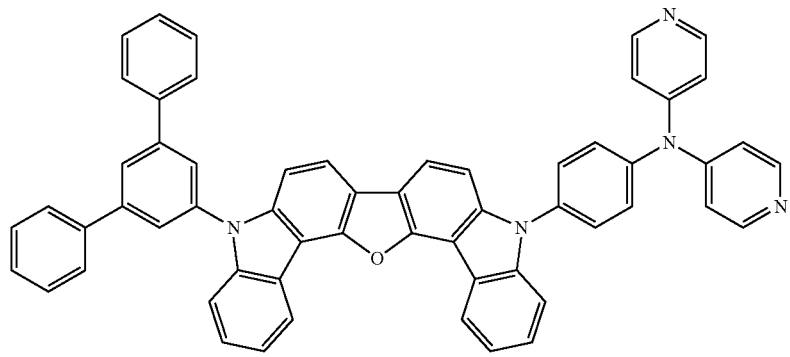
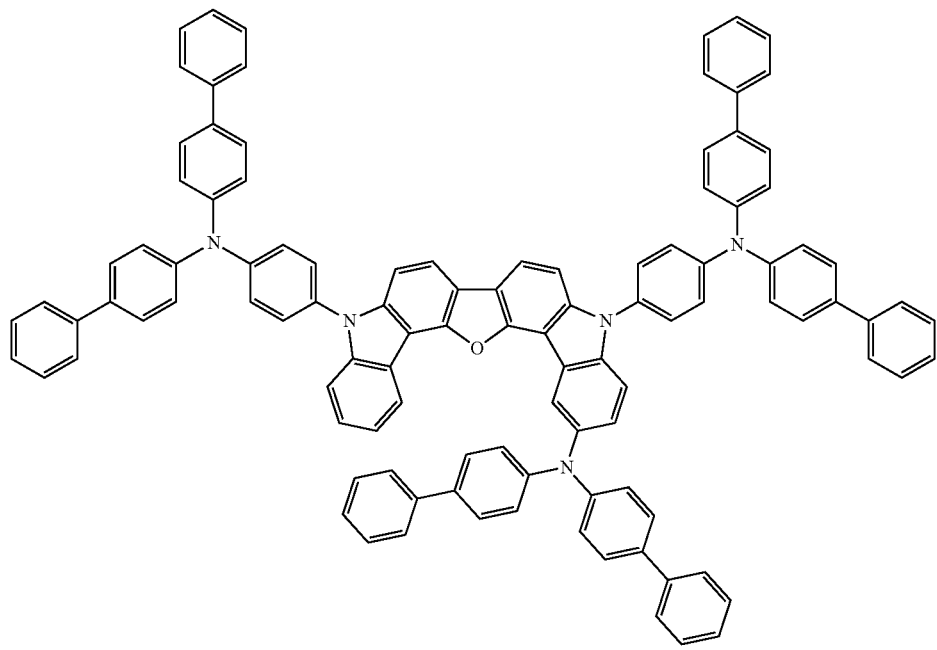
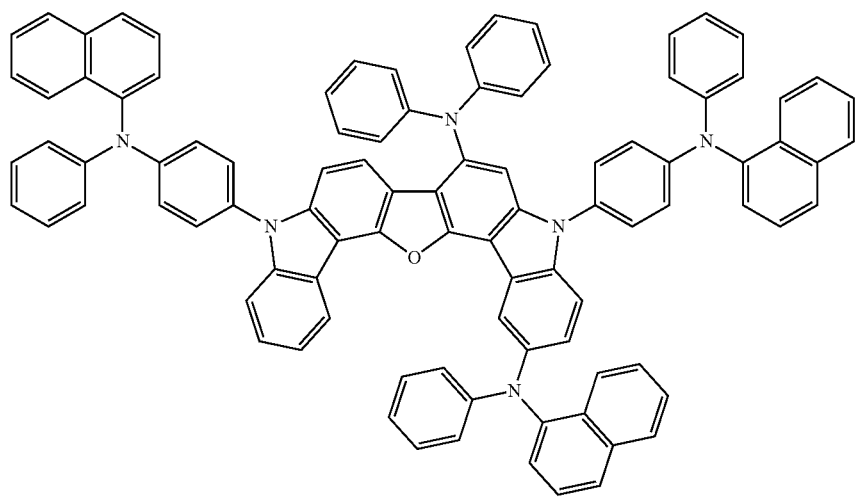

-continued
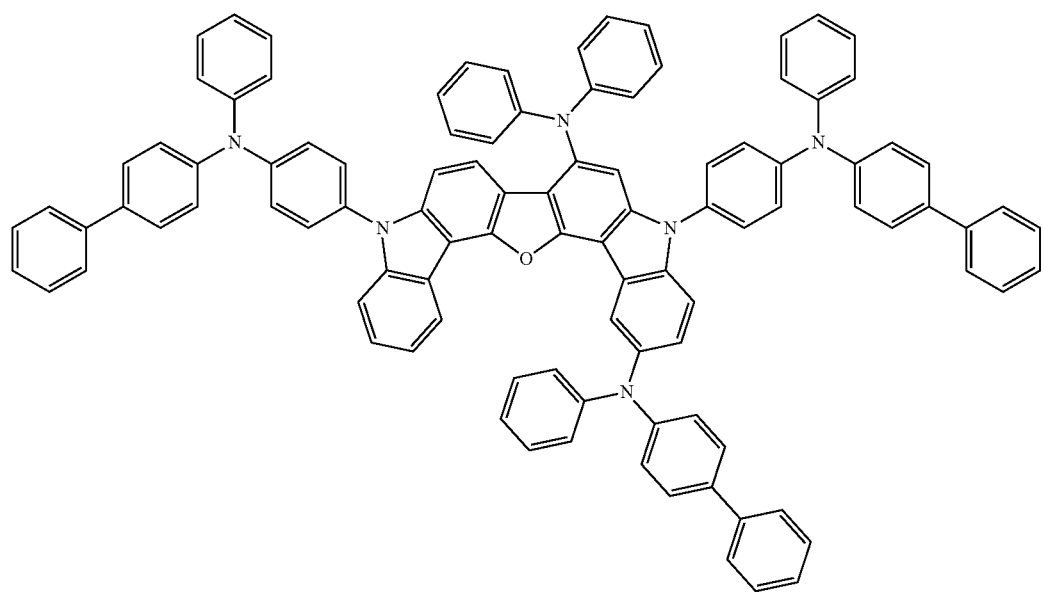
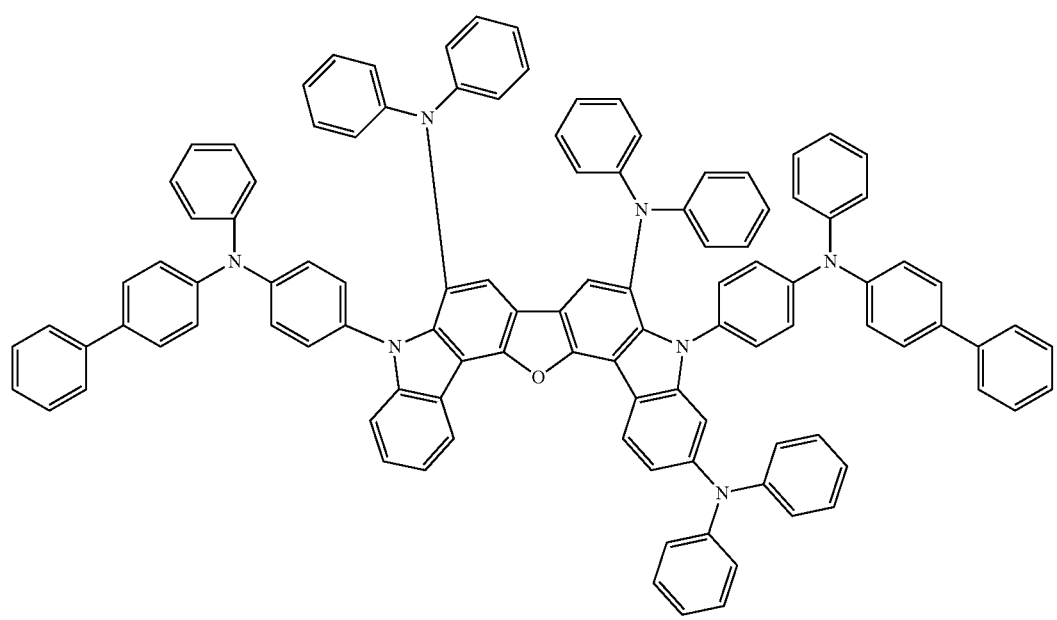

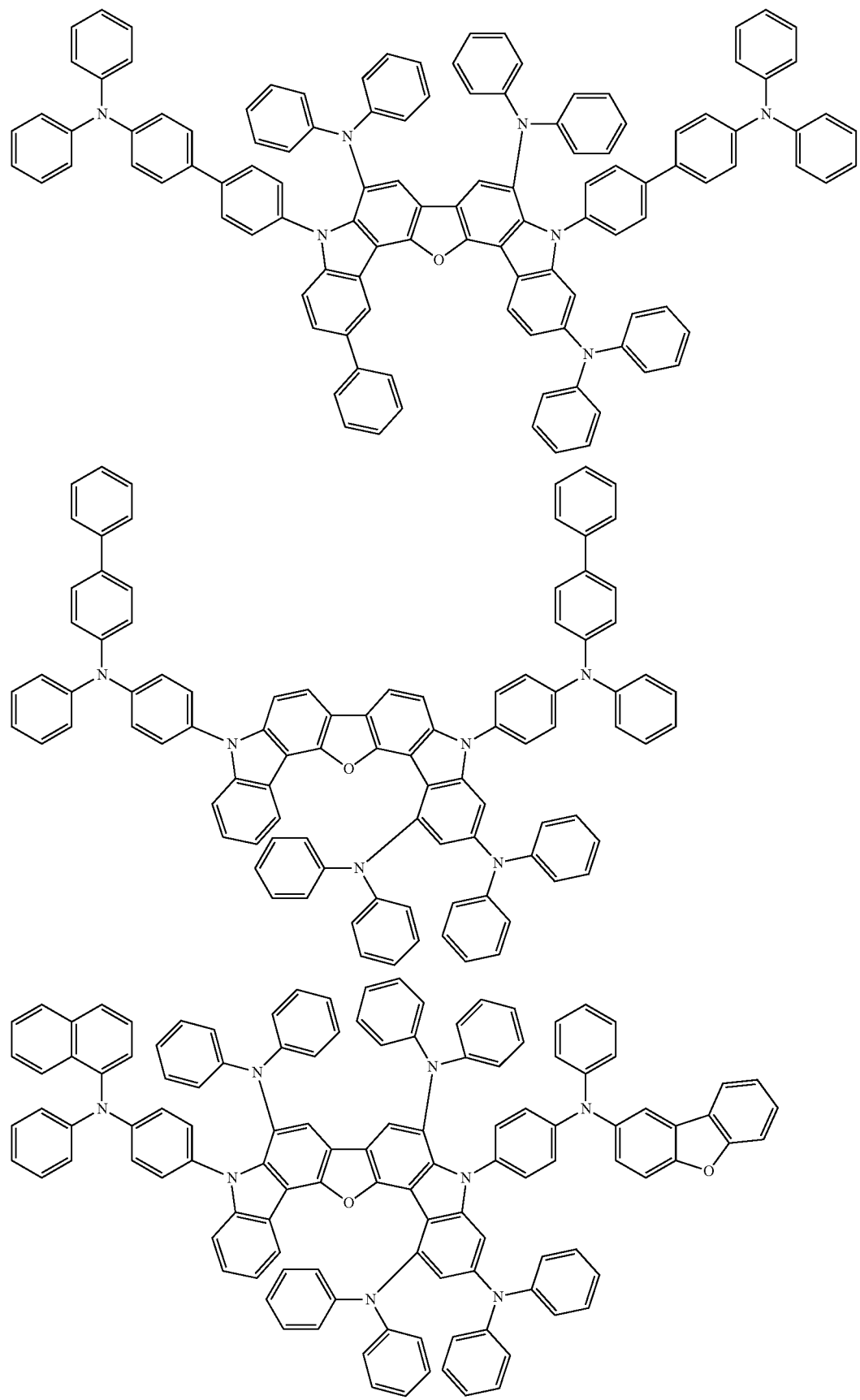

-continued
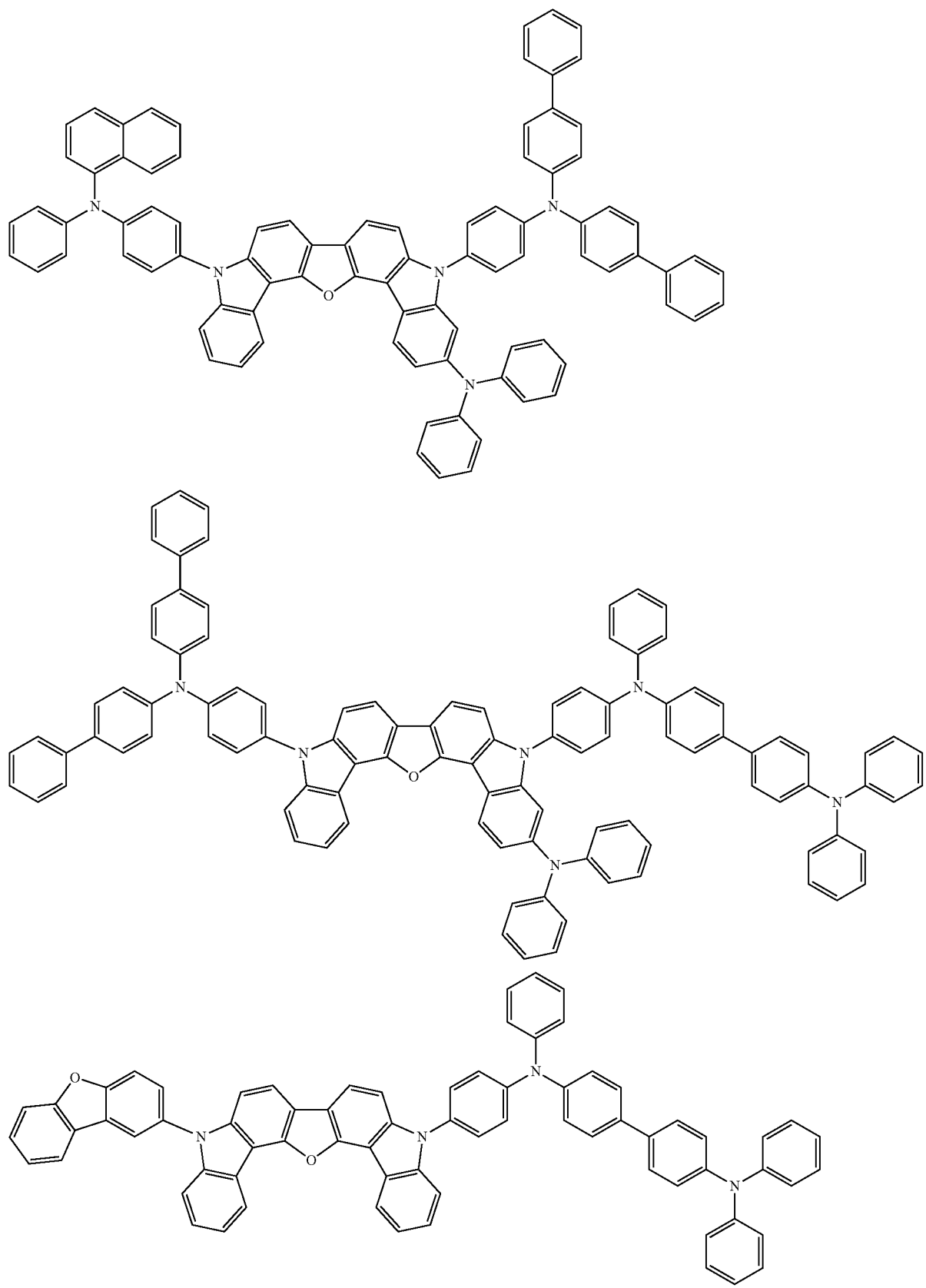

-continued
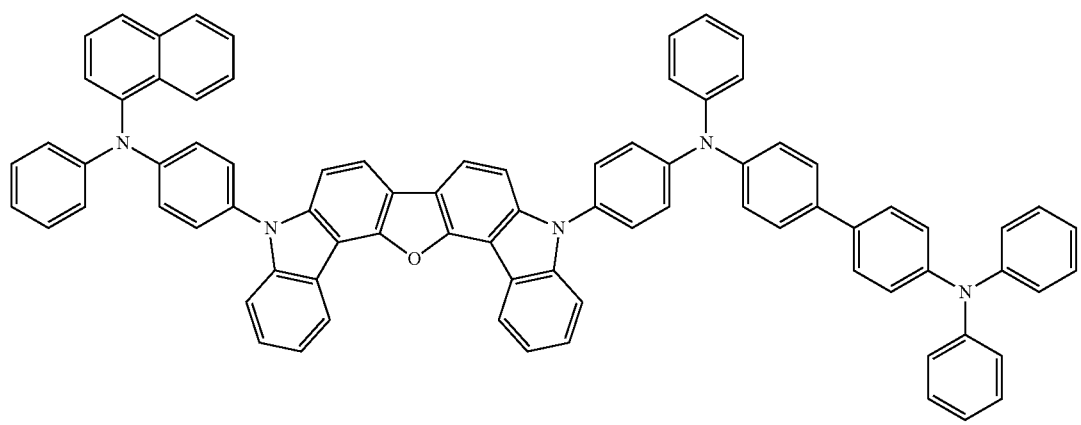
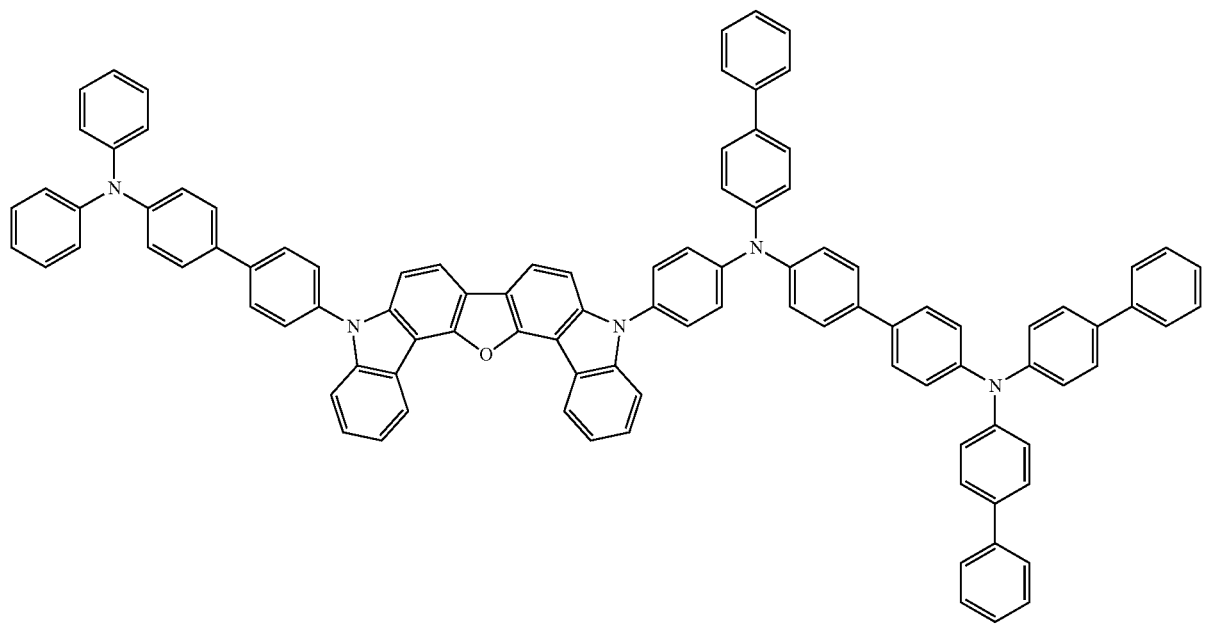
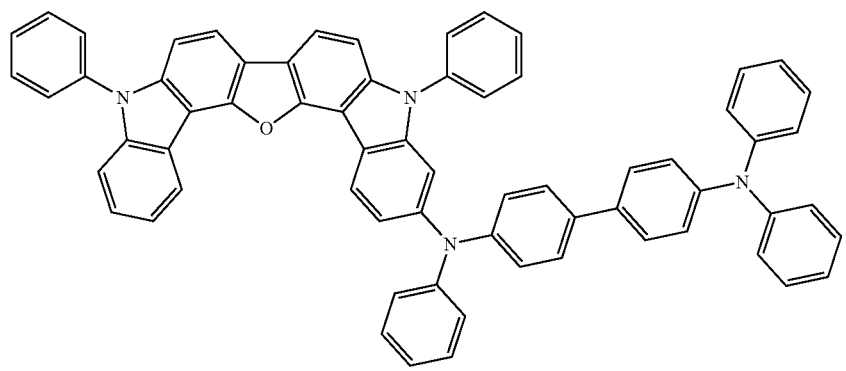

-continued
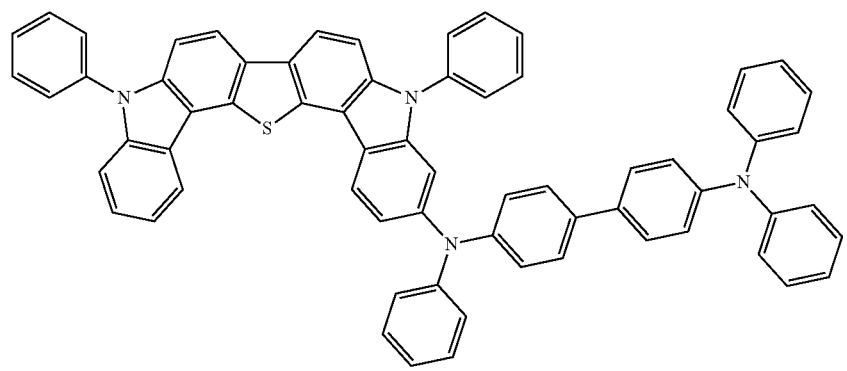
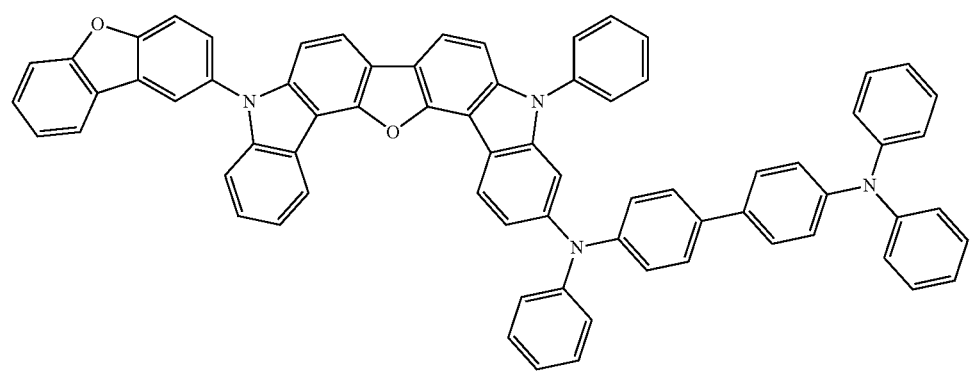
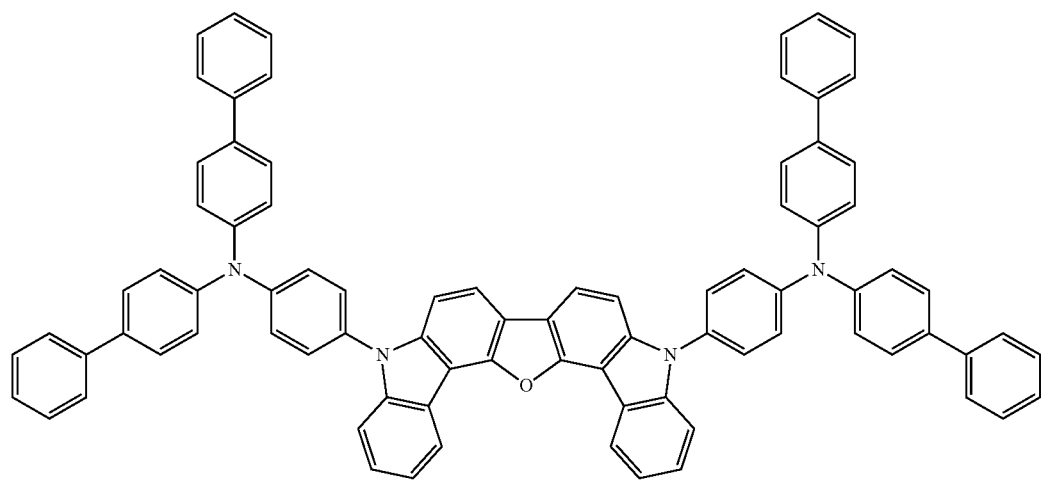
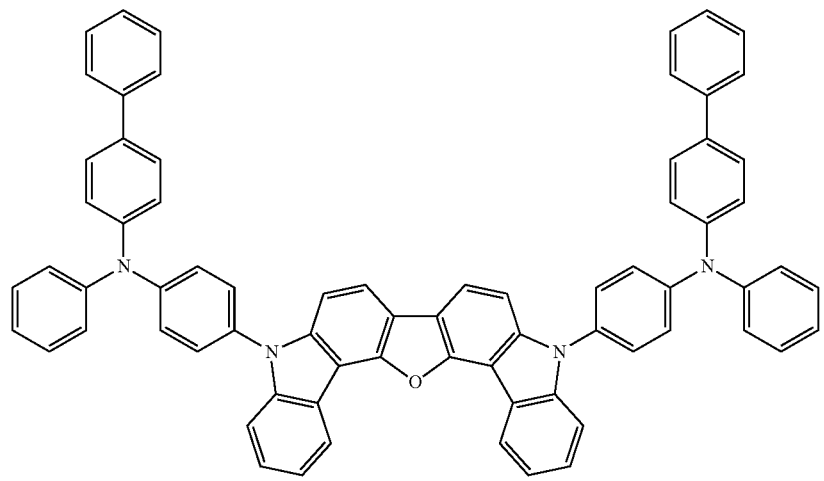

-continued
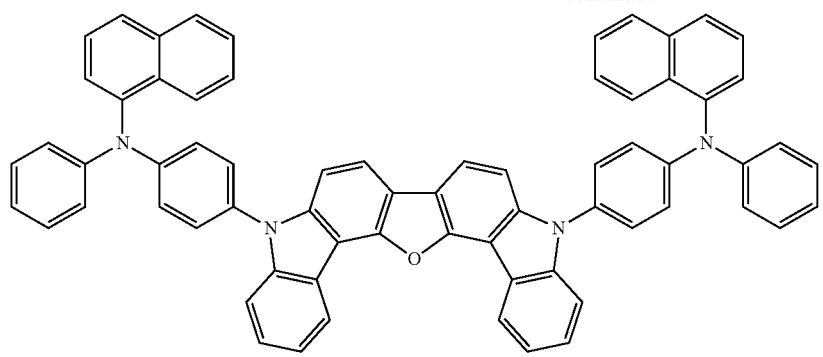
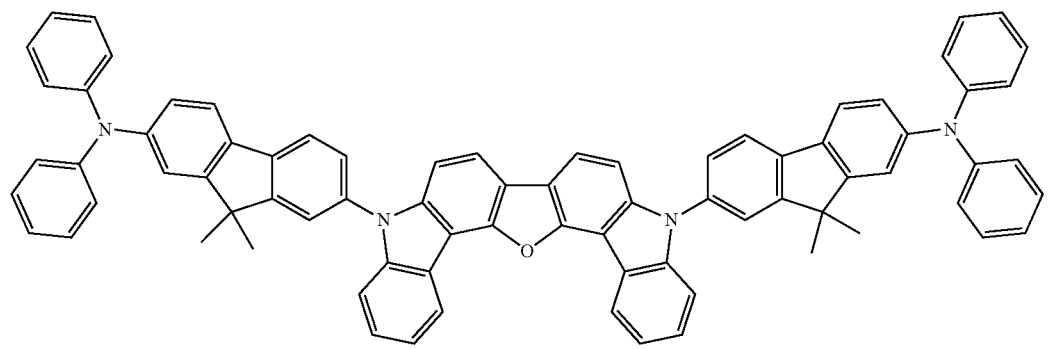
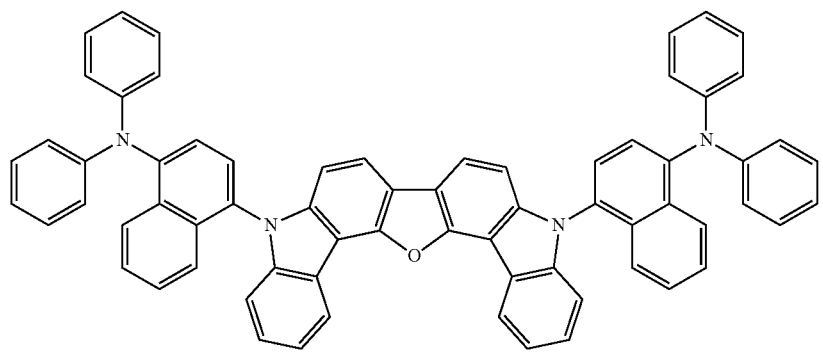
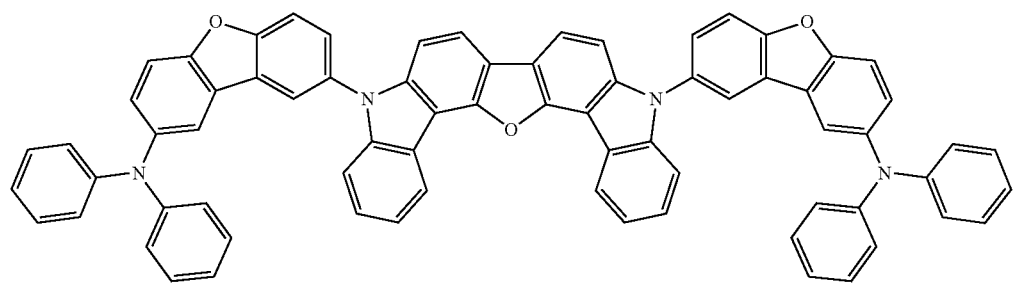
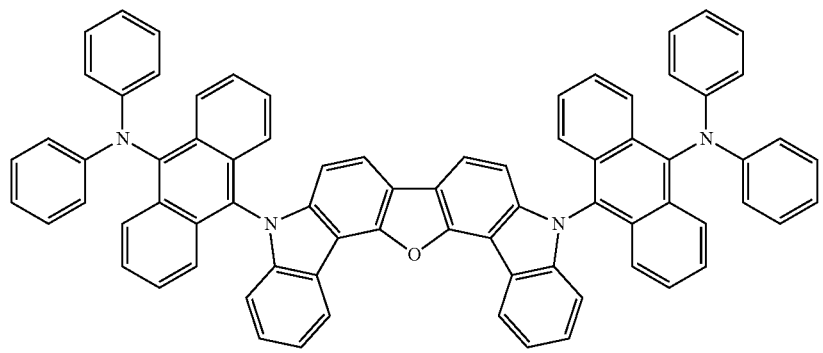

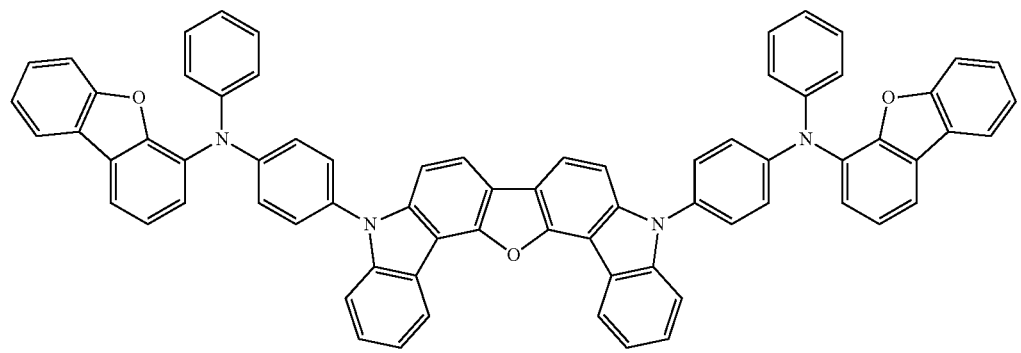
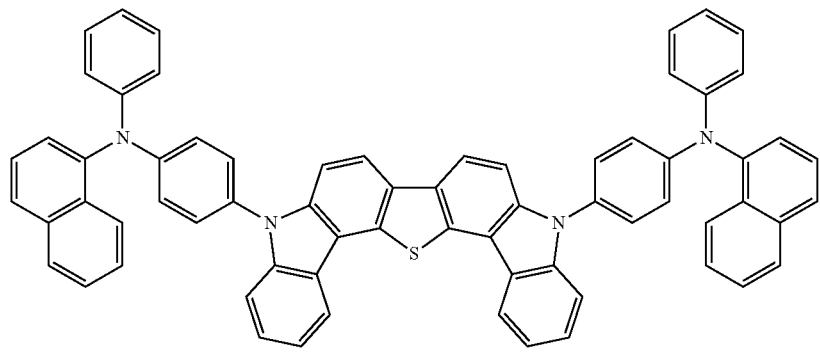
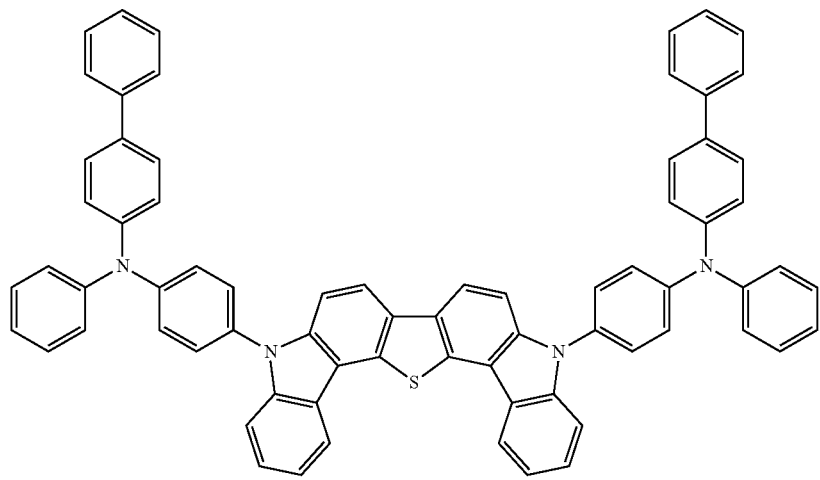
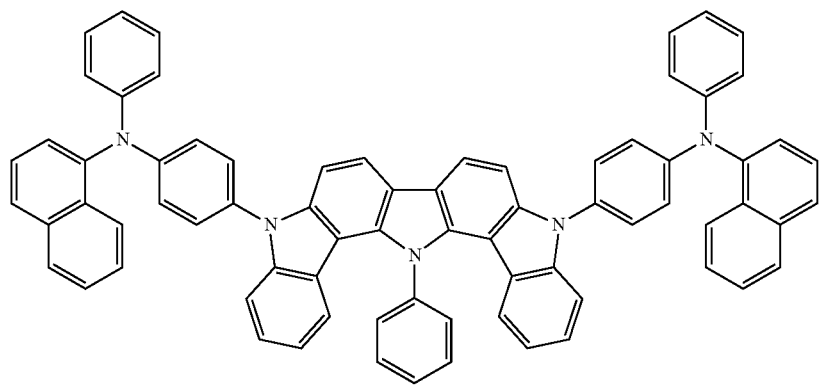

91 92
-continued
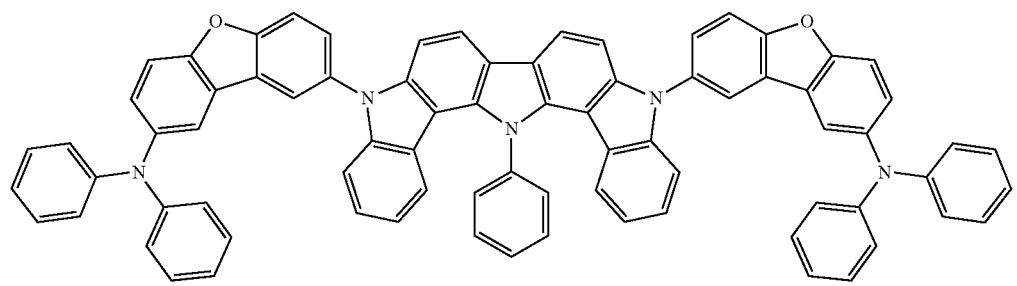
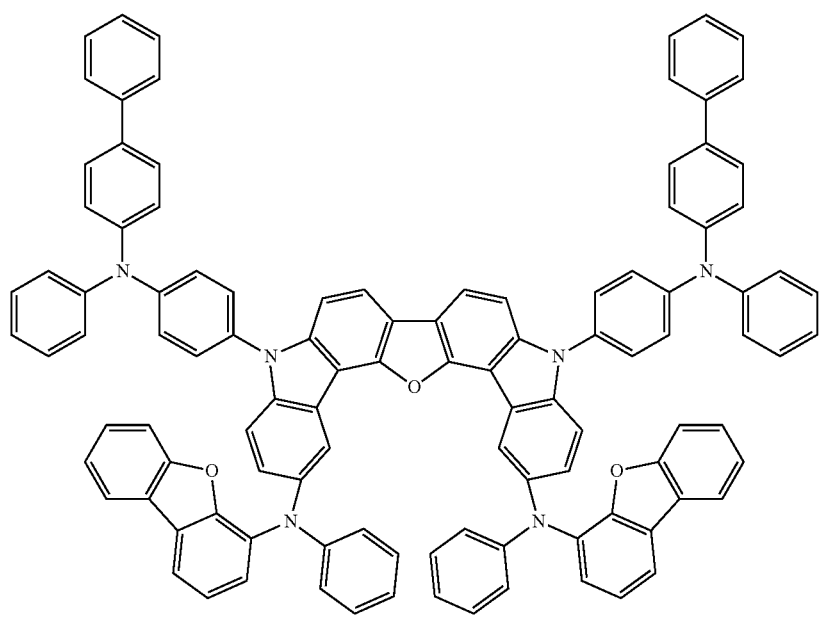
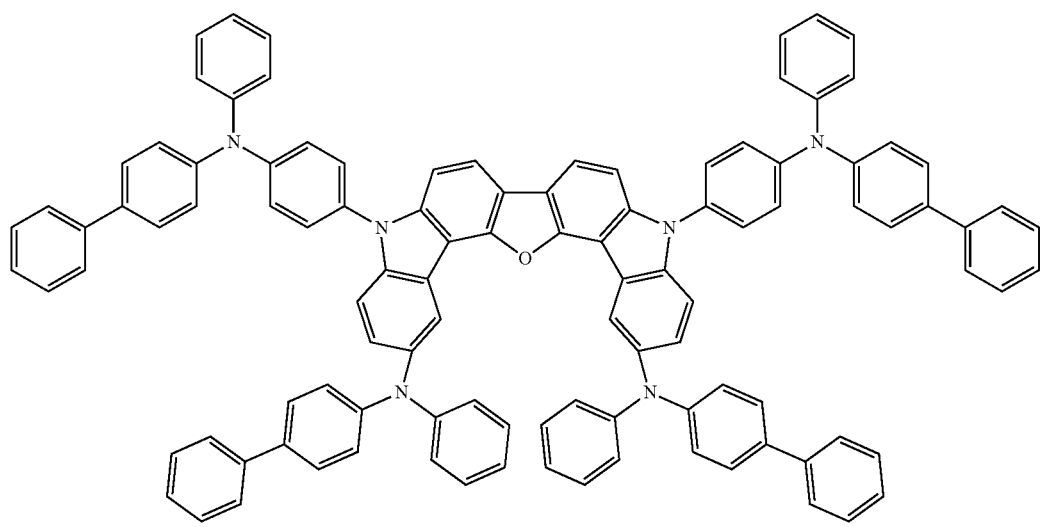

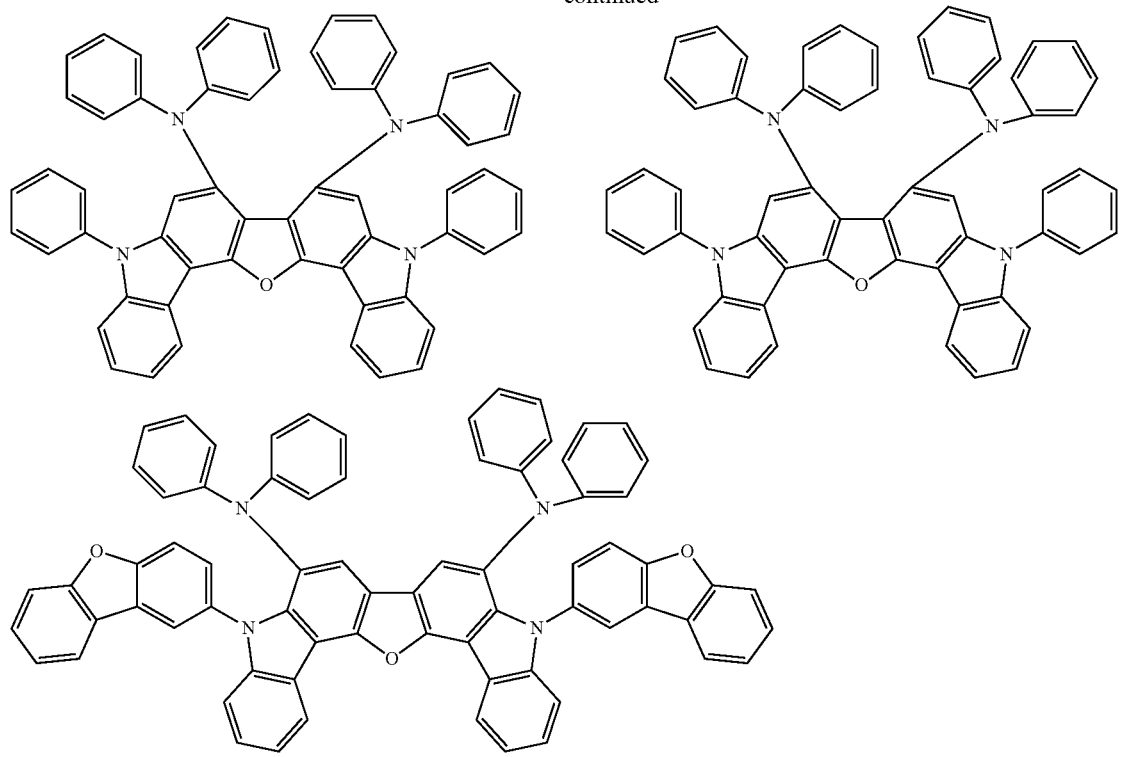

[Material for an Organic EL Device]

The compound represented by the formula (1) of the invention can be preferably used as a material for an organic EL device.

The material for an organic EL device according to one aspect of the invention comprises the compound represented by the formula (1) and is preferably used as a material for a hole-transporting layer that is adjacent to the emitting layer.

In the invention, the "material for a hole-transporting layer (hereinafter referred to as a hole-transporting material)" means a material that is used in a hole-transporting zone having one or more organic thin film layers. As the organic thin film layers of the hole-transporting zone, a hole-transporting layer, a hole-injecting layer, an electron-blocking layer or the like can be given.

The material for an organic EL device according to one aspect of the invention may contain only the compound represented by the formula (1) of the invention, and may contain other materials in addition to the compound represented by the formula (1) of the invention.

[Organic EL Device]

An explanation will be made on an organic EL device according to one aspect of the invention.

A first organic EL device of the invention comprises, between an anode and a cathode, one or more organic thin film layers including an emitting layer. At least one layer of the organic thin film layers comprises the material for an organic EL device or the hole-transporting material for an organic EL device of the invention.

A second organic EL device of the invention comprises, between an anode and a cathode, one or more organic thin film layers including an emitting layer, and a hole-transporting zone between the anode and the emitting layer, and the hole-transporting zone comprises the material for an organic EL device of the invention or the hole-transporting material for an organic EL device.

In the second organic EL device of the invention, it is preferred that the hole-transporting zone be adjacent to the emitting layer.

A third organic EL device of the invention comprises, between an anode and a cathode, one or more organic thin film layers including an emitting layer, and an electron-transporting zone between the cathode and the emitting layer, and the electron-transporting zone comprises the material for an organic EL device or the hole-transporting material for an organic EL device of the invention.

In the first to third organic EL devices of the invention, it is preferred that the emitting layer comprise the material for an organic EL device of the invention.

FIG. 1 is a schematic view showing a layer configuration of one embodiment of the organic EL device of the invention.

An organic EL device 1 has a structure in which, on a substrate 10, an anode 20, a hole-transporting zone 30, a phosphorescent emitting layer 40, an electron-transporting zone 50 and a cathode 60 are stacked in this sequence. The hole-transporting zone 30 means a hole-transporting layer, a hole-injecting layer, an electron-blocking layer or the like. Similarly, the electron-transporting zone 50 means an electron-transporting layer, an electron-injecting layer, a hole-blocking layer or the like. These layers may not be necessarily formed, but it is preferred that one or more layers be formed. In this device, the organic thin film layers mean organic layers provided in the hole-transporting zone 30, and the phosphorescent emitting layer 40 and organic layers provided in the electron-transporting zone 50. Among these organic thin film layers, at least one layer comprises the material for an organic EL device of the invention or one or more layers of the hole-transporting zone 30 comprise the hole-transporting material for an organic EL device of the invention. Due to this configuration, an organic EL device can emit light efficiently.

The content of the compound represented by the formula (1) relative to the organic thin film layer that comprises the material for an organic EL device of the invention is preferably 1 to 100 wt %. Similarly, the content of the compound represented by the formula (2) relative to any layer in the hole-transporting zone that comprises the hole-transporting material for an organic EL device of the invention is preferably 1 to 100 wt %.

In the organic EL device according to one aspect of the invention, it is preferred that the phosphorescent emitting layer 40 comprises the material for an organic EL device of the invention. It is more preferred that the material for an organic EL device of the invention be used as a host material of the emitting layer. Since the material of the invention has a sufficiently large triplet energy, even when a blue-emitting phosphorescent dopant material is used, the triplet energy of the phosphorescent dopant material can be efficiently confined in the emitting layer. Not only in the blue-emitting layer, the material for an organic EL device of the invention can be used in an emitting layer that emits light of a longer wavelength (green to red, or the like). However, it is preferable to use the material for an organic EL device in the blue-emitting layer.

The phosphorescent emitting layer comprises a phosphorescent emitting material (phosphorescent dopant). As the phosphorescent dopant, a metal complex compound can be given. Preferable is a compound that comprises a metal atom selected from Ir, Pt, Os, Au, Cu, Re and Ru and a ligand. It is preferred that the ligand have an ortho-metalated bond.

In respect of high phosphorescent quantum yield and capability of further improving the external quantum efficiency of the emitting device, it is preferred that the phosphorescent dopant be a compound that contains a metal atom selected from Ir, Os and Pt. A metal complex such as an iridium complex, an osmium complex and a platinum complex is further preferable. Among these, an iridium complex and a platinum complex are more preferable, with an ortho-metalated iridium complex being most preferable. The dopant may be used alone or in a mixture of two or more.

Although the concentration of the phosphorescent dopant in the phosphorescent emitting layer is not particularly restricted, it is preferably 0.1 to 40 weight % (wt %), and more preferably 0.1 to 30 weight % (wt %).

It is preferred that the material for an organic EL device or the invention be used in the organic thin film layers adjacent to the phosphorescent emitting 40. For example, when a layer that comprises the material of the invention (adjacent layer near to the anode) is formed between the phosphorescent emitting layer 40 and the hole-transporting zone 30, the layer functions an electron-barrier layer or an exciton-blocking layer.

The barrier layer (blocking layer) has a function of blocking movement of carriers or blocking of diffusion of excitons. An organic layer that serves to prevent leakage of electrons from the emitting layer to the hole-transporting zone may mainly be defined as an electron-barrier layer, and the organic layer that serves to prevent leakage of holes from the emitting layer to the electron-transporting zone may be defined as the hole-barrier layer. An organic layer that serves to prevent diffusion of triplet excitons generated in the emitting layer to peripheral layers of which the level of the triplet energy is lower than that of the emitting layer may be defined as an exciton-blocking layer (triplet barrier layer).

Further, the material for an organic EL device according to one aspect of the invention may be used in an organic thin film layer that is adjacent to the phosphorescent emitting layer 40 and also in another organic thin film layer that is in contact with the adjacent organic thin film layer.

In addition to the embodiments mentioned above, the organic EL device according to one aspect of the invention may take various known configurations. Further, emission from the emitting layer can be outcoupled from the anode, the cathode and both of the anode and the cathode.

In the organic EL device according to one aspect of the invention, it is preferred that at least any one of an electron-donating dopant and an organic metal complex be added to an interfacial region between the cathode and the organic thin film layer. Due to such a configuration, the luminance can be improved or the life can be prolonged in the organic EL device.

As the electron-donating dopant, at least one selected from an alkali metal, an alkali metal compound, an alkaline earth metal, an alkaline earth metal compound, a rare earth metal, a rare each metal compound or the like can be given.

As the organic metal complex, at least one selected from an organic metal complex containing an alkali metal, an organic metal complex containing an alkaline earth metal and an organic metal complex containing a rare earth metal or the like can be given.

As the alkali metal, lithium (Li) (work function: 2.93 eV), sodium (Na) (work function: 2.36 eV), potassium (K) (work function: 2.28 eV), rubidium (Rb) (work function: 2.16 eV), cesium (Cs) (work function: 1.95 eV) or the like can be given. An alkali metal having a work function of 2.9 eV or less is particularly preferable. Among these, K, Rb and Cs are preferable. Rb or Cs is further preferable, with Cs being most preferable.

As the alkaline earth metal, calcium (Ca) (work function: 2.9 eV), strontium (Sr) (work function: 2.0 eV to 2.5 eV), barium (B) (work function: 2.52 eV) or the like can be given. One having a work function of 2.9 eV or less is particularly preferable.

As the rare-earth metal, scandium (Sc), yttrium (Y), cerium (Ce), terbium (Tb), ytterbium (Yb) and the like can be given. One having a work function of 2.9 eV or less is particularly preferable.

Among the above-mentioned metals, the preferable metals have a particularly high reducing ability, and hence can provide the resulting organic EL device with improved luminance or a prolonged lifetime by adding a relatively small amount thereof to an electron-injecting region.

Examples of the alkali metal compound include an alkali oxide such as lithium oxide ($Li_2O$), cesium oxide ($Cs_2O$) or potassium oxide ($K_2O$), and an alkali halide such as lithium fluoride (LiF), sodium fluoride (NaF), cesium fluoride (CsF) or potassium fluoride (KF). Among these, lithium fluoride (LiF), lithium oxide ($Li_2O$) and sodium fluoride (NaF) are preferable.

Examples of the alkaline-earth metal compound include barium oxide (BaO), strontium oxide (SrO), calcium oxide (CaO), and mixtures thereof such as barium strontium acid ($Ba_xSr_{1-x}O$) ($0<x<1$) and barium calcium acid ($Ba_xCa_{1-x}$) ($0<x<1$). Among these, BaO, SrO and CaO are preferred.

Examples of the rare-earth metal compound include ytterbium fluoride ($YbF_3$), scandium fluoride ($ScF_3$), scandium oxide ($ScO_3$), yttrium oxide ($Y_2O_3$), cerium oxide ($Ce_2O_3$), gadolinium fluoride ($GdF_3$) and terbium fluoride ($TbF_3$). Among these, $YbF_3$, $ScF_3$ and $TbF_3$ are preferable.

The organic metal complexes are not particularly limited as long as they each contain, as a metal ion, at least one of alkali metal ions, alkaline-earth metal ions, and rare-earth metal ions, as mentioned above. Meanwhile, preferred examples of the ligand include, but are not limited to, quinolinol, benzoquinolinol, acridinol, phenanthridinol, hydroxyphenyloxazole, hydroxyphenytthiazole, hydroxydiaryloxadiazole, hydroxydiarylthiadiazole, hydroxyphenylpyridine, hydroxyphenylbenzimidazole, hydroxybenzotriazole, hydroxyfluborane, bipyridyl, phenanthroline, phthalocyanine, porphyrin, cyclopentadiene, β-diketones, azomethines, and derivatives thereof.

Regarding the addition form of the electron-donating dopant and the organic metal complex, it is preferred that the electron-donating dopant and the organic metal complex be formed in the shape of a layer or an island in the interfacial region. A preferred method for the formation is a method in which an organic substance as a light emitting material or an electron-injecting material for forming the interfacial region is deposited simultaneously with deposition of at least one of the electron-donating dopant and the organic metal complex by a resistant heating deposition method, thereby dispersing at least one of the electron-donating dopant and the organic metal complex reducing dopant in the organic substance. The dispersion concentration by molar ratio of the organic substance to the electron-donating dopant and/or the organic metal complex is normally 100:1 to 1:100, preferably 5:1 to 1:5.

In a case where at least one of the electron-donating dopant and the organic metal complex is formed into the shape of a layer, the light-emitting material or the electron-injecting material which serves as an organic layer in the interface is formed into the shape of a layer. After that, at least one of the electron-donating dopant and the organic metal complex is solely deposited by the resistant heating deposition method to form a layer preferably having a thickness of 0.1 nm to 15 nm.

In a case where at least one of the electron-donating dopant and the organic metal complex is formed into the shape of an island, the light-emitting material or the electron-injecting material which serves as an organic layer in the interface is formed into the shape of an island. After that, at least one of the electron-donating dopant and the organic metal complex is solely deposited by the resistant heating deposition method to form an island preferably having a thickness of 0.05 to 1 nm.

In addition, the ratio of the main component (emitting material or electron-injecting material) to at least one of the electron-donating dopant and the organic metal complex in the organic EL device according to one aspect of the invention (main component electron-donating dopant and/or organic metal complex) is preferably 5:1 to 1:5, more preferably 2:1 to 1:2 in terms of molar ratio.

In the organic EL device of the invention according to one aspect of the invention, configurations of other layers than those in which the above-mentioned material for an organic EL device of the invention is used are not particularly restricted, and known materials or the like can be used. Hereinbelow, a brief explanation will be made on the layer of the device of the embodiment 1. However, materials to be applied to the organic EL device of the invention are not limited to those mentioned below.

[Substrate]

As the substrate, a glass plate, a polymer plate or the like can be used.

Examples of materials of the glass plate include soda lime glass, barium-strontium-containing glass, lead glass, aluminosilicate glass, borosilicate glass, barium borosilicate glass, quartz, and the like.

Examples of materials of the polymer plate include polycarbonate, acryl, polyethylene terephthalate, polyethersulfone, polysulfone, and the like.

[Anode]

The anode is formed of a conductive material, for example. A conductive material having a work function larger than 4 eV is suitable.

As the conductive material, carbon, aluminum, vanadium, iron, cobalt, nickel, tungsten, silver, gold, platinum, palladium or the like, alloys thereof, an oxidized metal such as tin oxide and indium oxide used in an ITO substrate and a NESA substrate and further an organic conductive resin such as polythiophene and polypyrrole can be given.

If necessary, the anode may be formed of two or more layers.

[Cathode]

The cathode is formed of a conductive material, for example. A conductive material having a work function smaller than 4 eV is suitable.

As the conductive material, magnesium, calcium, tin, lead, titanium, yttrium, lithium, ruthenium, manganese, aluminum, lithium fluoride or the like, and alloys thereof can be given. The conductive material is not limited thereto.

As the alloy, a magnesium/silver alloy, a magnesium/indium alloy, a lithium/aluminum alloy or the like can be given as representative examples. The alloys are not limited thereto. The amount ratio of metals forming an alloy is controlled by the temperature of a deposition source, the atmosphere, the degree of vacuum or the like, and an appropriate ratio is selected.

If necessary, the cathode may be formed of two or more layers. The cathode can be formed by forming a thin layer from the above-mentioned conductive material by a method such as deposition, sputtering or the like.

When outcoupling light from the emitting layer through the cathode, it is preferable that the cathode have a light transmittance of more than 10%.

The sheet resistance of the cathode is preferably several hundred 0/square or less. The thickness of the cathode is normally 10 nm to 1 μm, and preferably 50 to 200 nm.

[Emitting Layer]

When a phosphorescent emitting layer is formed by using materials other than the material for an organic EL device of the invention, materials which are known as a material for a phosphorescent emitting layer can be used. Specifically, reference can be made to WO2005-079118 or the like.

Figure 2:
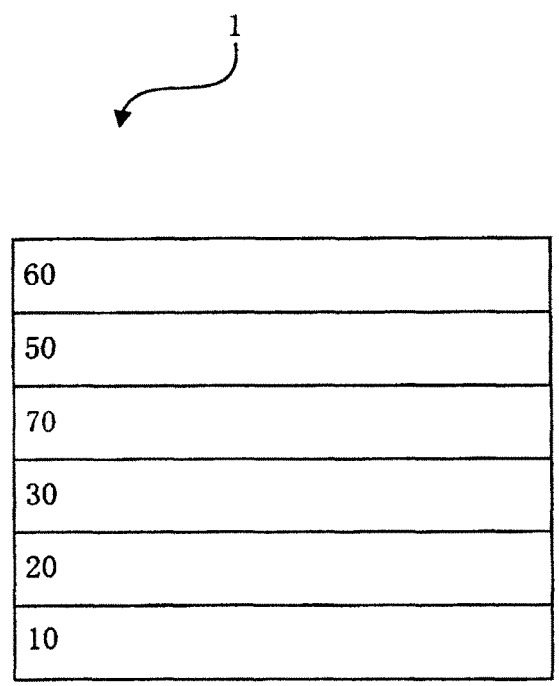
FIG. 2 is a view showing one embodiment of the organic EL device of the invention.

The organic EL device according to one aspect of the invention may comprise a fluorescent emitting layer 70 as in the case of the device shown in FIG. 2 instead of the phosphorescent emitting layer 40 of the device shown in FIG. 1. As the fluorescent emitting layer, known materials can be used.

The emitting layer can be of a double-host (often referred to as host/co-host) type. Specifically, in the emitting layer, an electron-transporting host and a hole-transporting host may be combined to control the carrier balance therein.

The emitting layer also may be of a double-dopant type. By incorporating two or more kinds of dopant materials having a high quantum yield to the emitting layer, each dopant emits light. For example, there may be a case that a yellow emitting layer is realized by co-depositing a host, and a red dopant and a green dopant.

The emitting layer may be a single layer or may have a stacked layer structure. When the emitting layers are stacked, due to accumulation of electrons and holes in the interface of the emitting layer, the recombination region may be concentrated in the emitting layer interface, whereby the quantum efficiency is improved.

[Hole-Injecting Layer and Hole-Transporting Layer]

A hole-injecting layer and transporting layer is a layer that helps holes to be injected to an emitting layer and to be transported to an emitting region. It has a large hole mobility and a small ionization energy.

As the material for a hole-injecting and transporting layer, a material that transports holes to the emitting layer at a lower electric field is preferable. Further, it is preferred that the material have a mobility of holes of at least $10^{-4}$ cm$^2$/V sec when an electric field of $10^4$ to $10^6$ V/cm is applied.

[Electron-Injecting Layer and Electron-Transporting Layer]

The electron-injecting and transporting layer helps electrons to be injected to an emitting layer and to be transported to an emitting region. It has a large electron mobility.

In the organic EL device, it is known that since emitted light is reflected by an electrode (a cathode, for example), emission outcoupled directly from an anode interferes with emission outcoupled after being reflected by the electrode. In order to utilize the interference effect efficiently, the film thickness of the electron-injecting and transporting layer is appropriately selected to be several nm to several μm. When the film thickness is large, in particular, it is preferred that the electron mobility be at least $10^{-5}$ cm$^2$/Vs or more at an applied electric field intensity of $10^4$ to $10^6$ V/cm in order to avoid an increase in voltage.

As the electron-transporting material used in the electron-injecting and transporting layer, an aromatic heterocyclic compound containing one or more hetero atoms in the molecule is preferably used, with a nitrogen-containing ring derivative being particularly preferable. Further, as the nitrogen-containing ring derivative, an aromatic ring compound having a nitrogen-containing 6-membered ring or 5-membered ring skeleton, or a fused aromatic ring compound having a nitrogen-containing 6-membered ring or 5-membered ring skeleton is preferable. Examples thereof include compounds containing a pyridine ring, a pyrimidine ring, a triazine ring, a benzimidazole ring, a phenanthroline ring, a quinazoline ring or the like in the skeleton.

In addition, an organic layer with a semiconductor property may be formed by doping a donor material (n) or doping an acceptor material (p). Representative examples of N-doping include one in which an electron-transporting material is doped with a metal such as Li or Cs. Representative examples of P-doping include one in which a hole-transporting material is doped with an acceptor material such as F4TCNQ (see Japan Patent No. 3695714, for example).

Each layer of the organic EL device according to one aspect of the invention can be formed by using known methods including the dry-type film formation such as vacuum deposition, sputtering, plasma coating, ion-plating or the like and the wet-type film formation such as spin coating, dipping, flow coating or the like.

The film thickness of each layer is not particularly limited, but should be set to be a proper thickness. If the film thickness is too large, a large voltage is required to be applied in order to obtain a certain light output, thereby leading to lowering in efficiency. If the film thickness is too small, due to generation of pinholes or the like, a sufficient luminance cannot be obtained when an electric field is applied. Normally, the film thickness is preferably 5 nm to 10 μm, and a range of 10 nm to 0.2 μm is further preferable.

An organic EL device obtained by using a material for an organic EL device that comprises the compound of the invention and/or the hole-transporting material for an organic EL device of the invention can be used in an electric equipment such as a display component including an organic EL panel module, a display apparatus such as a TV, a mobile phone or a personal computer and an emitting apparatus such as lightings, lights for vehicles or the like.

EXAMPLES

The invention will be explained in more detail in accordance with the Synthesis Examples and the Examples, which should not be construed as limiting the scope of the invention.

Synthesis Example 1 (Synthesis of Compound (1))

(1) Synthesis of Compound (1-1)

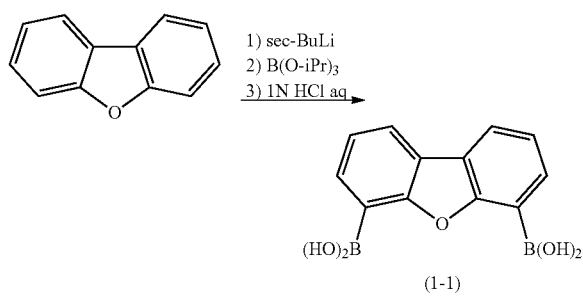

In a three-neck flask, 20.0 g (80.9 mmol) of dibenzofuran and 200 ml of dehydrated tetrahydrofuran were placed. In a nitrogen atmosphere, the reactor was cooled to −70° C. To the reactor, 53 ml (88.9 mmol) of a 1.68M s-butyllithium hexane solution was added dropwise, and the resultant was stirred at −70° C. for 1 hour. 37.3 ml (162 mmol) of triisopyl borate was added, and stirred at room temperature for 6 hours. After completion of the reaction, 100 ml of a 1N HCL aqueous solution was added, and stirred for 30 minutes. A sample solution was transferred to a dropping funnel, and extracted several times with dichloromethane. The extracted product was dried with anhydrous magnesium sulfate, filtered and concentrated. The concentrated product was washed by dispersing in hexane, whereby white solids were obtained.

The yield was 15.9 g and the percentage yield was 93%.

(2) Synthesis of Compound (1-2)

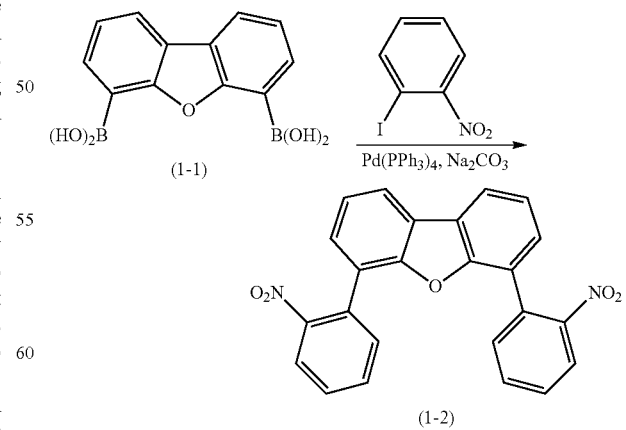

In a three-neck flask, 25.0 g (97.7 mmol) of compound (1-1), 74.7 g (300 mmol) of 2-iodonitrobenzene, 250 mL of a 2M aqueous solution of sodium carbonate, 500 mL of 1,2-dimethoxyethane and 2.30 g (1.95 mmol) of Pd(PPh₃)₄ were placed, and the mixture was refluxed in a nitrogen atmosphere for 12 hours. After completion of the reaction, the sample solution was filtered, and the obtained solids were washed with methanol and hexane.

The yield was 26.5 g and the percentage yield was 66%.

(3) Synthesis of Compound (1-3)

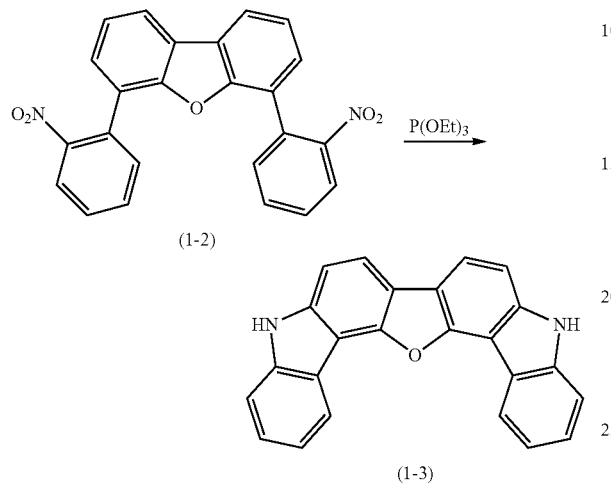

In a three-neck flask, 26.5 g (64.6 mmol) of compound (1-2) and 430 ml of triethyl phosphite were placed, and the mixture was refluxed with heating at 170° C. for 16 hours.

After completion of the reaction, distillation was conducted, thereby to remove the remaining triethyl phosphite and triethyl phosphite residues. The obtained organic phase was purified by silica gel chromatography (hexane:dichloromethane:10:1 to 5:1 to 1:1), whereby pale yellow solids were obtained.

The yield was 12.1 g and the percentage yield was 54%.

(4) Synthesis of Compound (1-4)

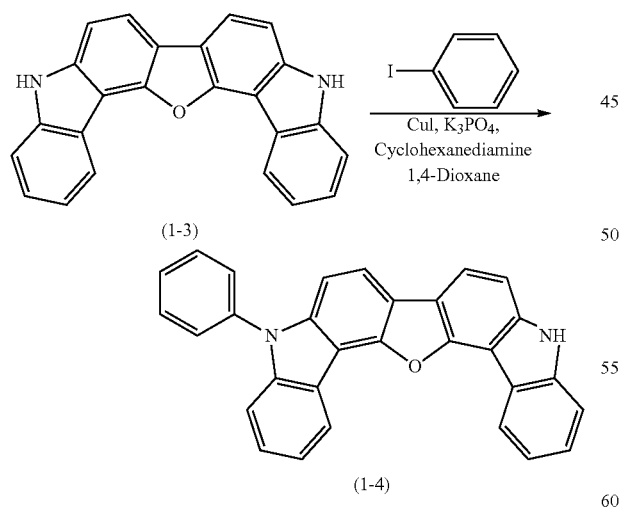

In a three-neck flask, 3.46 g (10 mmol) of compound (1-3), 2.04 g (10 mmol) of iodobenzene, 1.90 g (10 mmol) of copper iodide, 4.24 g (20 mmol) of tripotassium phosphate, 2.28 g (20 mmol) of cyclohexadiamine and 30 mL of 1,4-dioxane were placed. The mixture was refluxed for 12 hours in a nitrogen atmosphere.

After completion of the reaction, insoluble matters were removed by filtration through celite. The filtrate was transferred to a dripping funnel, and extracted several times with dichloromethane. The obtained organic phase was dried with anhydrous magnesium sulfate, filtered and concentrated. The concentrated product was purified by silica gel chromatography (hexane:dichloromethane=10:1 to 5:1), whereby white solids were obtained.

The yield was 3.38 g and the percentage yield was 40%.

(5) Synthesis of Compound (1)

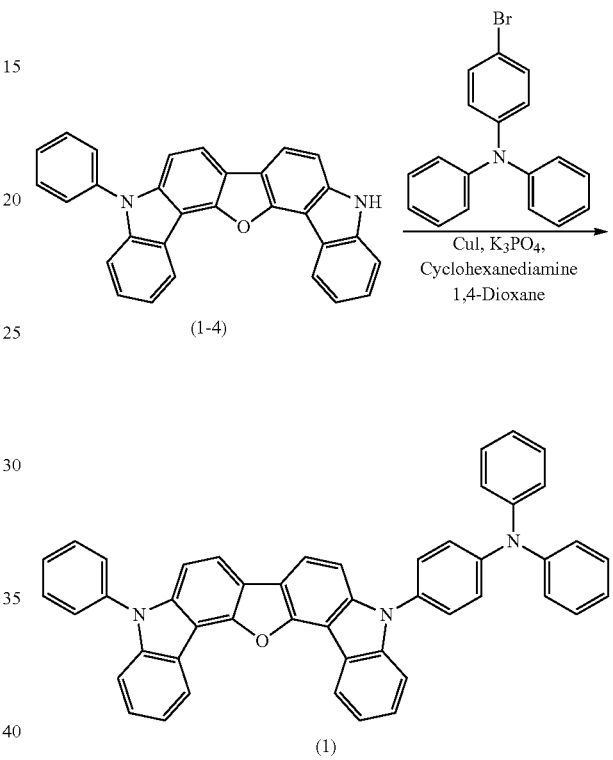

In a three-neck flask, 2.11 g (5 mmol) of compound (1-4), 1.78 g (5.5 mmol) of 4-bromotriphenylamine, 0.95 g (5 mmol) of copper iodide, 2.12 g (10 mmol) of potassium triphosphate, 1.14 g (10 mmol) of cyclohexanediamine and 20 mL of 1,4-dioxane were placed. The mixture was refluxed in a nitrogen atmosphere for 12 hours.

After completion of the reaction, insoluble matters were removed by filtration through celite. The filtrate was transferred to a dripping funnel, and extracted several times with toluene. The obtained organic phase was dried with anhydrous magnesium sulfate, filtered and concentrated. The concentrated product was purified by silica gel chromatography (hexane:toluene=7:3), whereby white solids were obtained.

The yield was 2.16 g and the percentage yield was 65%.

As a result of a FD-MS analysis, m/e was 665 relative to the molecular weight of 665. The measurement results of ¹H-NMR are shown below.

¹H-NMR (400 MHz, CDCl₃) δ7.07-7.12 (2H, m), 7.22-7.40 (10H, m), 7.43-7.53 (11H, m), 7.63-7.70 (4H, m), 7.94-7.99 (2H, m), 8.75-8.79 (2H, m)

Synthesis Example 2 (Synthesis of Compound (2))

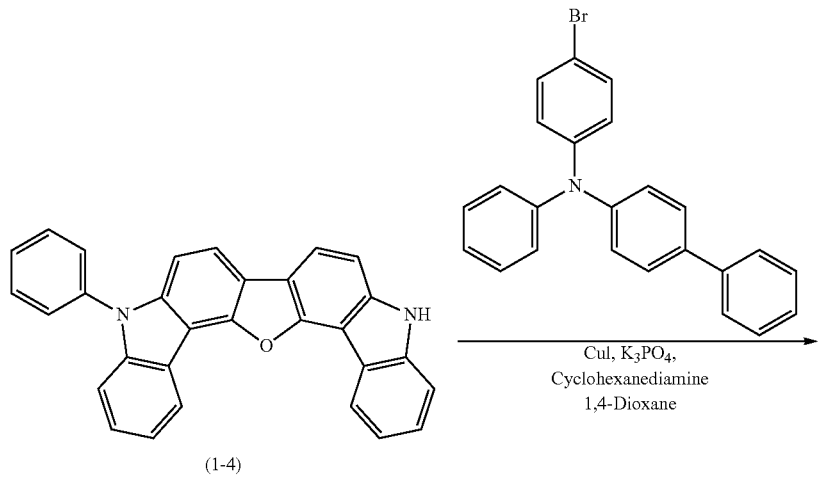

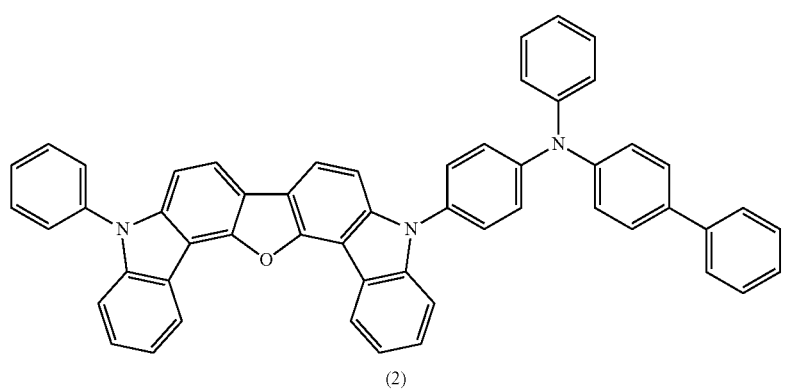

In a three-neck flask, 2.11 g (5 mmol) of compound (1-4), 2.20 g (5.5 mmol) of N-(4-bromophenyl)-N-(4-biphenyl)aniline, 0.95 g (5 mmol) of copper iodide, 2.12 g (10 mmol) of potassium triphosphate, 1.14 g (10 mmol) of cyclohexanediamine and 20 mL of 1,4-dioxane were placed. The mixture was refluxed in a nitrogen atmosphere for 18 hours.

After completion of the reaction, insoluble matters were removed by filtration through celite. The filtrate was transferred to a dripping funnel and extracted several times with toluene. The obtained organic phase was dried with anhydrous magnesium sulfate, filtered and concentrated. The resultant was purified by silica gel chromatography (hexane:toluene=3:1), whereby white solids were obtained.

The yield was 2.60 g and the percentage yield was 70%.

As a result of a FD-MS analysis, m/e was 741 relative to the molecular weight of 741.

The measurement results of $^1$H-NMR are shown below.

$^1$H-NMR (400 MHz, CDCl$_3$) δ7.11-7.18 (2H, m), 7.21-7.39 (9H, m), 7.41-7.69 (20H, m), 7.98-8.03 (2H, m), 8.76-8.79 (2H, m)

Synthesis Example 3 (Synthesis of Compound (3))

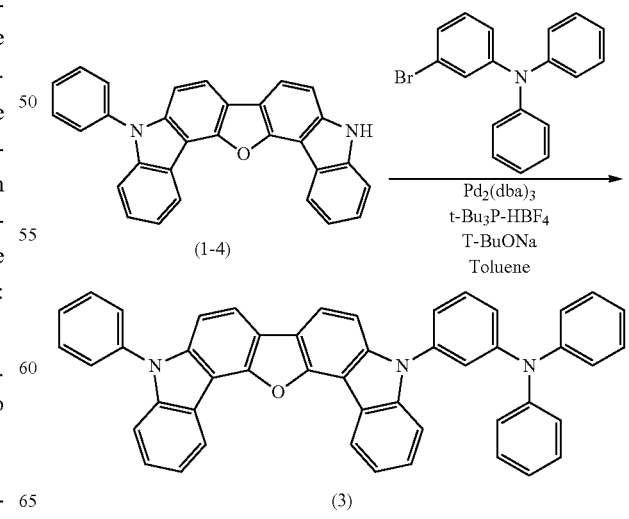

In a three-neck flask, 2.11 g (5 mmol) of compound (1-4), 1.78 g (5.5 mmol) of 3-bromotriphenylamine, 90 mg (0.1 mmol) of Pd₂(dba)₃, 0.12 g (0.4 mmol) of tri-t-butylphosphonium tetrafluoroborate, 0.67 g (7 mmol) of sodium t-butoxide and 30 mL of dehydrated toluene were placed. The resultant was refluxed in an argon atmosphere for 12 hours.

After completion of the reaction, insoluble matters were separated by filtration through celite. The filtrate was transferred to a dripping funnel and extracted several times with toluene. The obtained organic phase was dried with anhydrous magnesium sulfate, filtered and concentrated. The resultant was purified by silica gel chromatography (hexane: toluene=5:2), whereby white solids were obtained.

The yield was 2.40 g and the percentage yield was 72%.

As a result of a FD-MS analysis, m/e was 665 relative to the molecular weight of 665.

Synthesis Example 4 (Synthesis of Compound (4))

In a three-neck flask, 2.11 g (5 mmol) of compound (14), 2.06 g (5.5 mmol) of N-(4-bromophenyl)-N-(1-naphthyl)aniline, 90 mg (0.1 mmol) of Pd₂(dba)₃, 0.12 g (0.4 mmol) of tri-t-butylphosphonium tetrafluoroborate, 0.67 g (7 mmol) of sodium t-butoxide and 30 mL of dehydrated toluene were placed. The resultant was refluxed for 24 hours in an argon atmosphere.

After completion of the reaction, insoluble matters were separated by filtration through celite. The filtrate was transferred to a dripping funnel and extracted several times with toluene. The obtained organic phase was dried with anhydrous magnesium sulfate, filtered and concentrated. The resultant was purified by silica gel chromatography (hexane: toluene=4:1), whereby white solids were obtained.

The yield was 3.15 g and the percentage yield was 88%.

As a result of a FD-MS analysis, m/e was 715 relative to the molecular weight of 715.

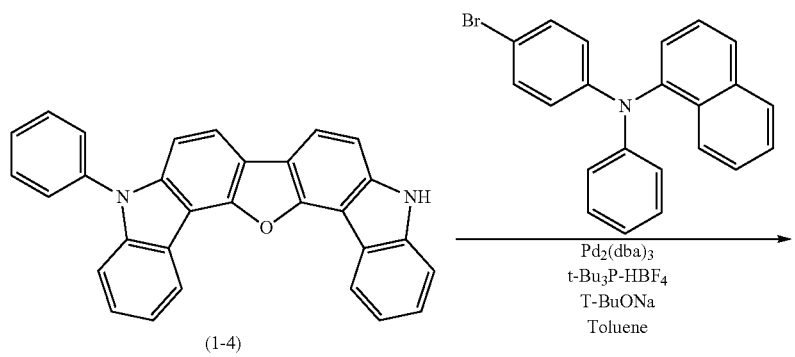

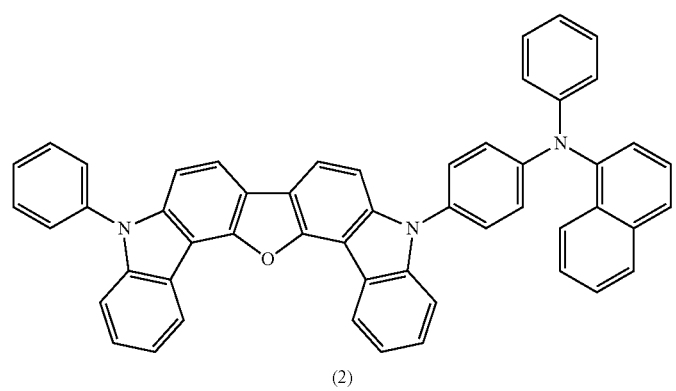

Synthesis Example 5 (Synthesis of Compound (5))

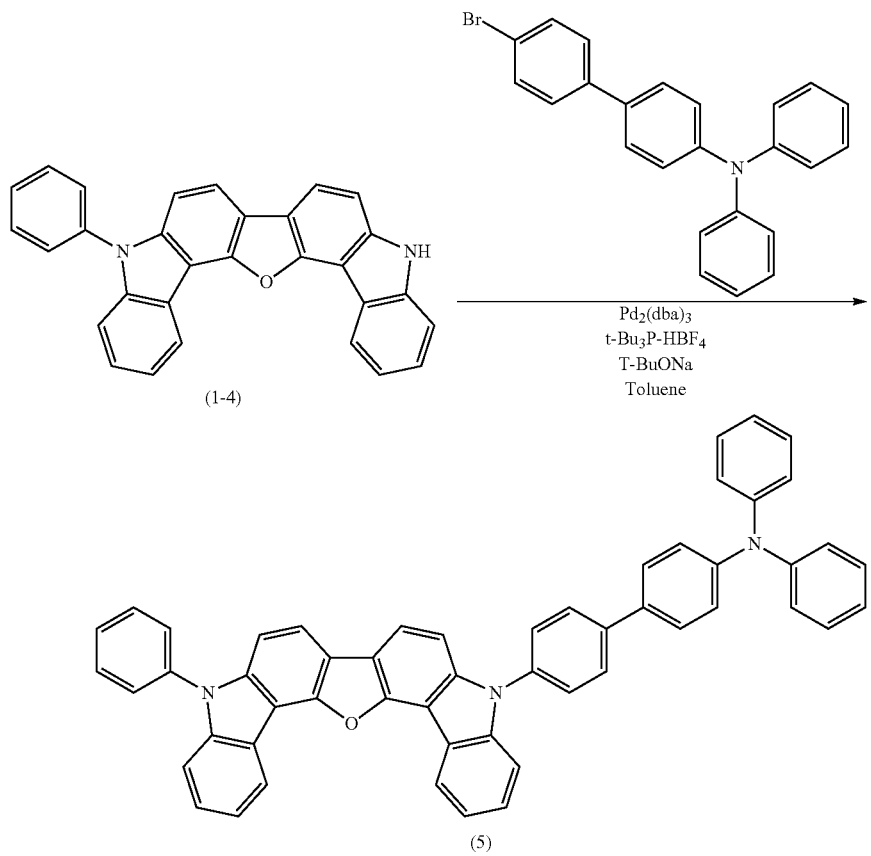

In a three-neck flask, 2.11 g (5 mmol) of compound (1-4), 2.20 g (5.5 mmol) of 4-bromo-4'-(diphenylamino)biphenyl, 90 mg (0.1 mmol) of $Pd_2(dba)_3$, 0.12 g (0.4 mmol) of tri-t-butylphosphonium tetrafluoroborate, 0.67 g (7 mmol) of sodium t-butoxide and 30 mL of dehydrated toluene were plated. The resultant was refluxed for 36 hours in an argon atmosphere.

After completion of the reaction, insoluble matters were separated by filtration through celite. The filtrate was transferred to a dripping funnel and extracted several times with toluene. The obtained organic phase was dried with anhydrous magnesium sulfate, filtered and concentrated. The concentrated product was purified by silica gel chromatography (hexane:toluene=2:1), whereby white solids were obtained.

The yield was 3.15 g and the percentage yield was 85%.

As a result of a FD-MS analysis, m/e was 741 relative to the molecular weight of 741.

Synthesis Example 6 (Synthesis of Compound (6))

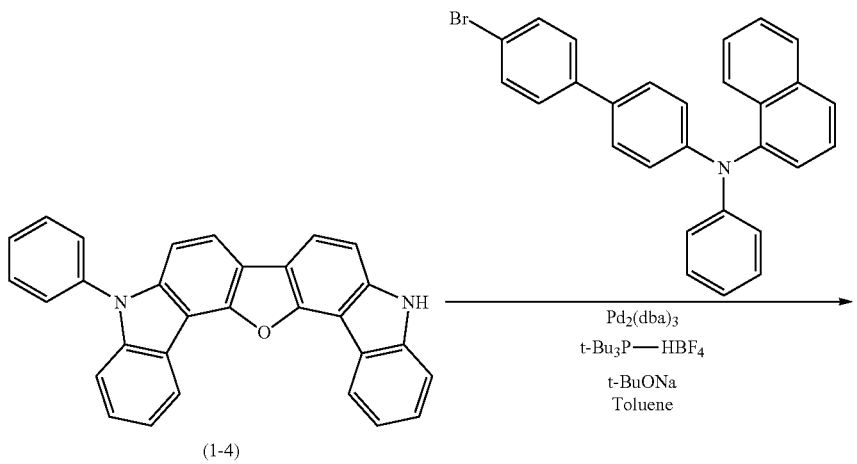

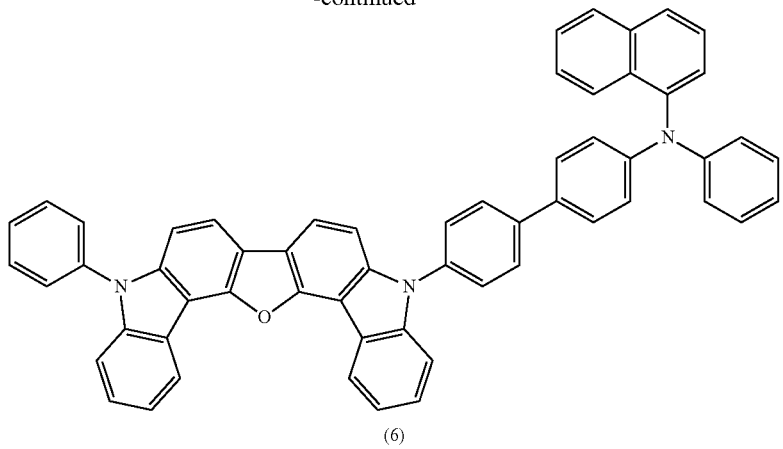

(6)

In a three-neck flask, 2.11 g (5 mmol) of compound (1-4), 2.20 g (5.5 mmol) of 4-bromo-4'-[N-phenyl-N-(1-naphthyl)amino]biphenyl, 90 mg (0.1 mmol) of $Pd_2(dba)_3$, 0.12 g (0.4 mmol) of tri-t-butylphosphonium tetrafluoroborate, 0.67 g (7 mmol) of sodium t-butoxide and 30 mL of dehydrated toluene were placed. The resultant was refluxed for 36 hours in an argon atmosphere.

After completion of the reaction, insoluble matters were separated by filtration. The filtrate was transferred to a dripping funnel and extracted several times with toluene. The obtained organic phase was dried with anhydrous magnesium sulfate, filtered and concentrated. The resultant was purified by silica gel chromatography (hexane:toluene=2:1), whereby white solids were obtained.

The yield was 2.45 g and the percentage yield was 62%.

As a result of a FD-MS analysis, m/e was 791 relative to the molecular weight of 791.

Synthesis Example 7 (Synthesis of Compound (7))

(1) Synthesis of Compound (7-1)

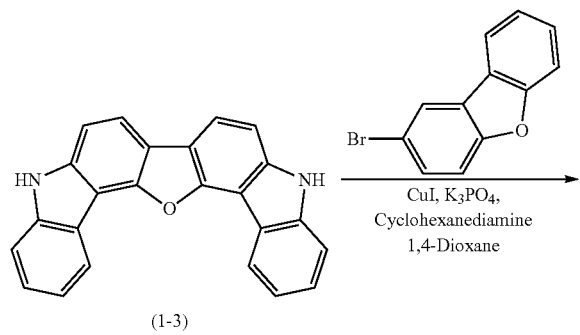

(1-3)

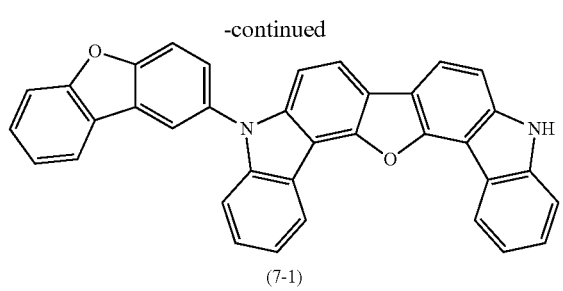

(7-1)

In a three-neck flask, 34.6 g (100 mmol) of compound (1-3), 24.7 g (100 mmol) of 2-bromodibenzofuran, 19.0 g (100 mmol) of copper iodide, 21.2 g (100 mmol) of potassium triphosphate, 5.9 g (50 mmol) of cyclohexanediamine and 500 mL of dehydrated 1,4-dioxane were placed. The resultant was refluxed for 48 hours in an argon atmosphere.

After completion of the reaction, insoluble matters were separated by filtration through celite. The filtrate was transferred to a dripping funnel and extracted several times with toluene. An organic phase obtained was dried with anhydrous magnesium sulfate, filtered and concentrated. The resultant was purified by silica gel chromatography (hexane:toluene=10:1 to 5:1 to 2:1), whereby compound (7-1) as white solids was obtained.

The yield was 11.8 g and the percentage yield was 23%.

(2) Synthesis of Compound (7)

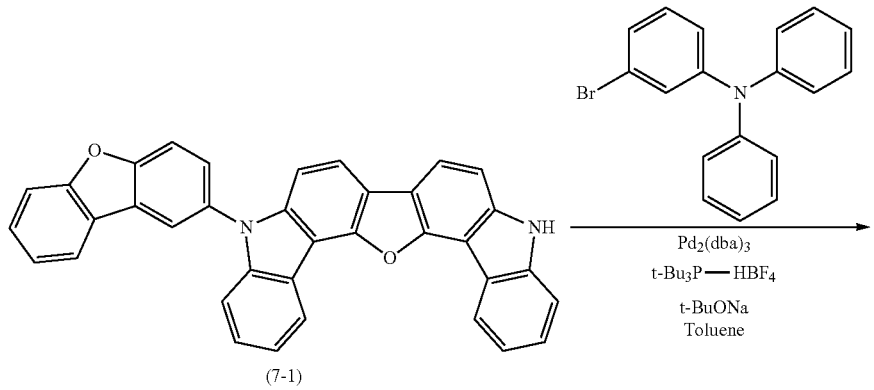

(7-1)

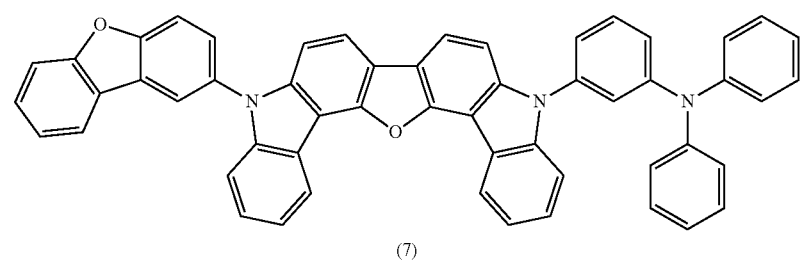

(7)

In a three-neck flask, 2.56 g (5 mmol) of compound (7-1), 1.78 g (5.5 mmol) of 3-bromotriphenylamine, 90 mg (0.1 mmol) of $Pd_2(dba)_3$, 0.12 g (0.4 mmol) of tri-t-butylphosphonium tetrafluoroborate, 0.67 g (7 mmol) of sodium t-butoxide and 30 mL of dehydrated toluene were placed. The resultant was refluxed in an argon atmosphere for 20 hours.

After completion of the reaction, insoluble matters were separated by filtration through celite. The filtrate was transferred to a dripping funnel and extracted several times with toluene. An organic phase obtained was dried with anhydrous magnesium sulfate, filtered and concentrated. The resultant was purified by silica gel chromatography (hexane:toluene=3:1), whereby white solids were obtained.

The yield was 2.83 g and the percentage yield was 75%.

As a result of a FD-MS analysis, m/e was 755 relative to the molecular weight of 755.

Synthesis Example 8 (Synthesis of Compound (8))

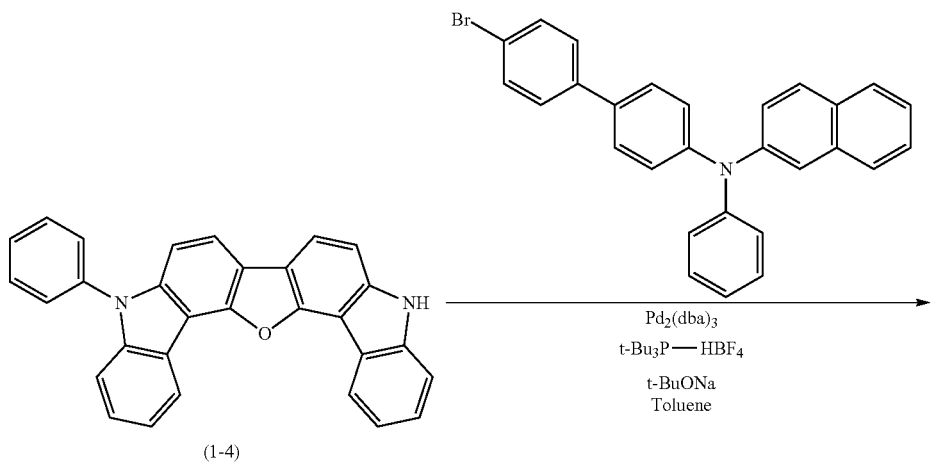

(1-4)

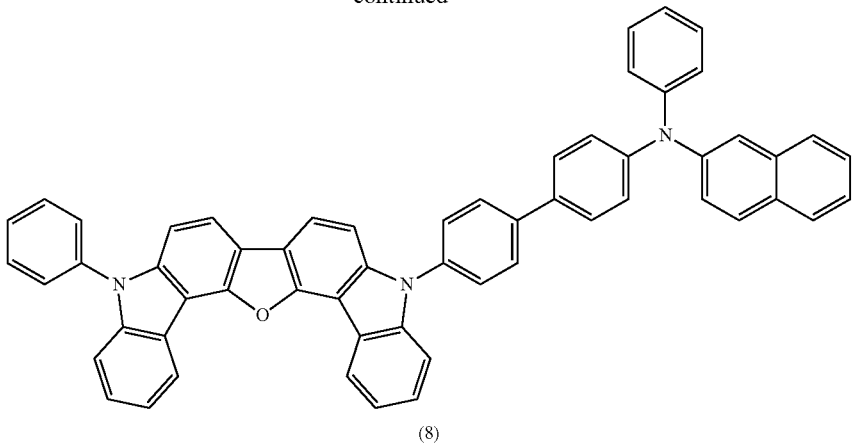

(8)

In a three-neck flask, 2.11 g (5 mmol) of compound (1-4), 2.20 g (5.5 mmol) of 4-bromo-4'-[N-phenyl-N-(2-naphthyl)amino]biphenyl, 90 mg (0.1 mmol) of Pd$_2$(dba)$_3$, 0.12 g (0.4 mmol) of tri-t-butylphosphonium tetrafluoroborate, 0.67 g (7 mmol) of sodium t-butoxide and 30 mL of dehydrated toluene were placed. The resultant was refluxed in an argon atmosphere for 36 hours.

After completion of the reaction, insoluble matters were separated by filtration through celite. The filtrate was transferred to a dripping funnel and extracted several times with toluene. An organic phase obtained was dried with anhydrous magnesium sulfate, filtered and concentrated. The resultant was purified by silica gel chromatography (hexane:toluene=2:1), whereby white solids were obtained.

The yield was 3.64 g and the percentage yield was 92%.

As a result of a FD-MS analysis, m/e was 791 relative to the molecular weight of 791.

Synthesis Example 9 (Synthesis of Compound (9))

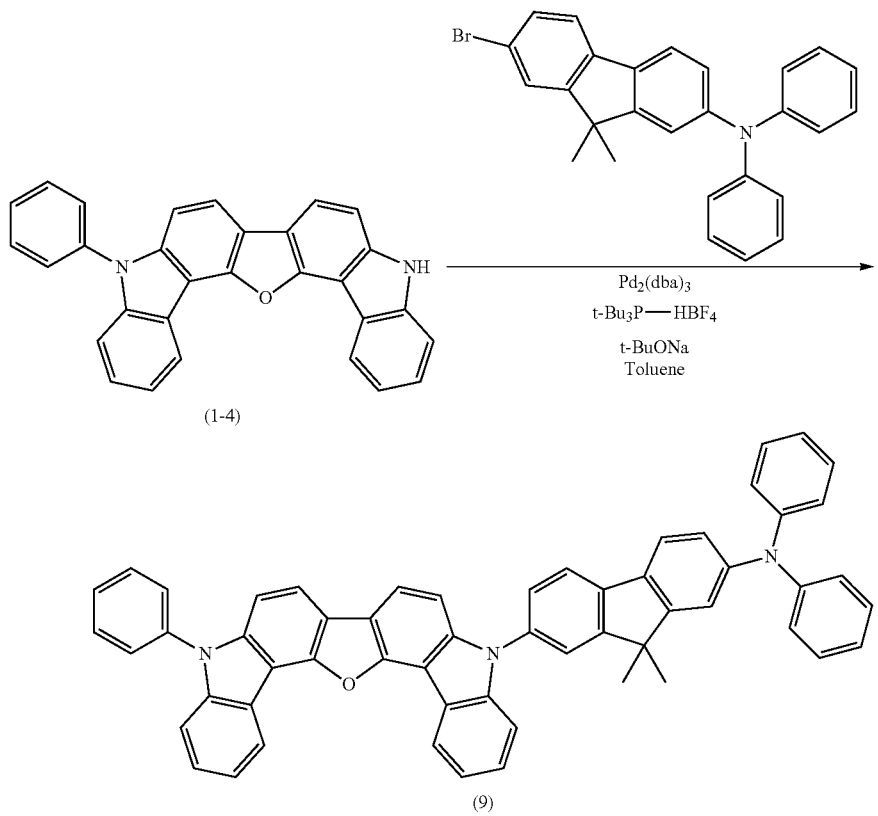

In a three-neck flask, 2.11 g (5 mmol) of compound (1-4), 2.42 g (5.5 mmol) of 2-bromo-7-(diphenylamino)-9,9'-dimethylfluorene, 90 mg (0.1 mmol) of Pd$_2$(dba)$_3$, 0.12 g (0.4 mmol) of tri-t-butylphosphonium tetrafluoroborate, 0.67 g (7 mmol) of sodium t-butoxide and 30 mL of dehydrated toluene were placed. The resultant was refluxed in an argon atmosphere for 12 hours.

After completion of the reaction, insoluble matters were separated by filtration through celite. The filtrate was transferred to a dripping funnel and extracted several times with toluene. The organic phase obtained was dried with anhydrous magnesium sulfate, filtered and concentrated. The concentrated product was purified by silica gel chromatography (hexane:toluene=3:2), whereby white solids were obtained.

The yield was 1.95 g and the percentage yield was 50%.

As a result of a FD-MS analysis, m/e was 781 relative to the molecular weight of 781.

Synthesis Example 10 (Synthesis of Compound (10))

(1) Synthesis of Compound (10-1)

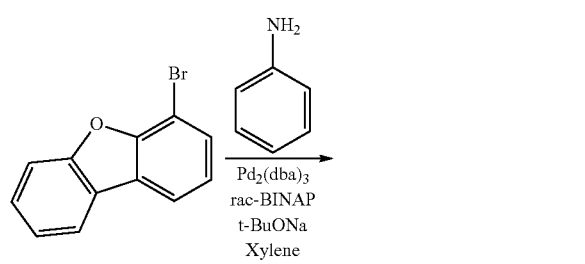

(10-1)

In a three-neck flask, 15.0 g (60.7 mmol) of 4-bromobenzofuran, 11.3 g (121 mmol) of aniline, 0.83 g (0.91 mmol) of Pd$_2$(dba)$_3$, 1.13 g (1.81 mmol) of rac-BINAP, 11.6 g (120.7 mmol) of sodium t-butoxide and 300 mL of dehydrated xylene were placed. The resultant was refluxed in an argon atmosphere for 8 hours.

After completion of the reaction, insoluble matters were separated by filtration through celite. The filtrate was transferred to a dripping funnel and extracted several times with toluene. The obtained organic phase was dried with anhydrous magnesium sulfate, filtered and concentrated. The concentrated product was purified by silica gel chromatography (hexane:toluene=4:1), whereby white solids were obtained.

The yield was 12.1 g and the percentage yield was 77%.

(2) Synthesis of Compound (10-2)

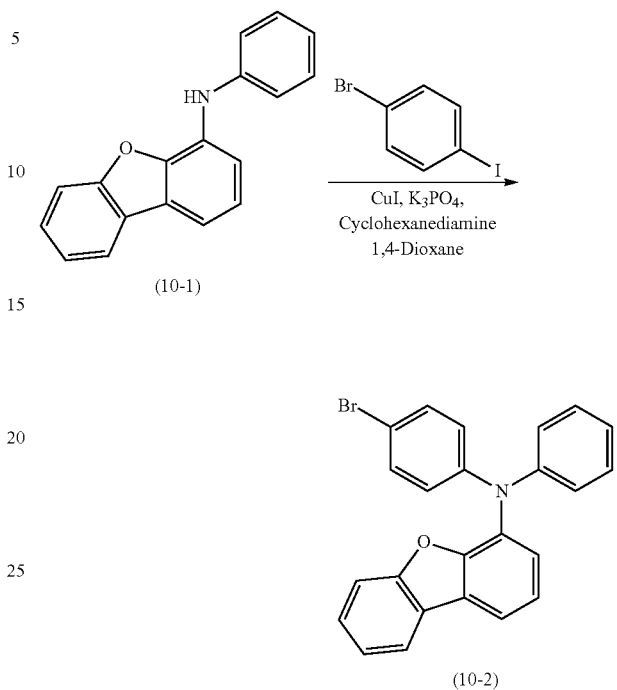

(10-1)

(10-2)

In a three-neck flask, 5.19 g (20 mmol) of compound (10-1), 5.66 g (20 mmol) of 4-bromoiodobenzene, 3.80 g (20 mmol) of copper iodide, 8.48 g (40 mmol) of potassium triphosphate, 4.56 g (40 mmol) of cyclohexanediamine and 60 mL of 1,4-dioxane were placed. The resultant was refluxed in an argon atmosphere for 30 hours.

After completion of the reaction, insoluble matters were separated by filtration through celite. The filtrate was transferred to a dripping funnel and extracted several times with toluene. An organic phase obtained was dried with anhydrous magnesium sulfate, filtered and concentrated. The resultant was purified by silica gel chromatography (hexane:toluene=4:1), whereby white solids were obtained.

The yield was 2.32 g and the percentage yield was 28%.

(3) Synthesis of Compound (10)

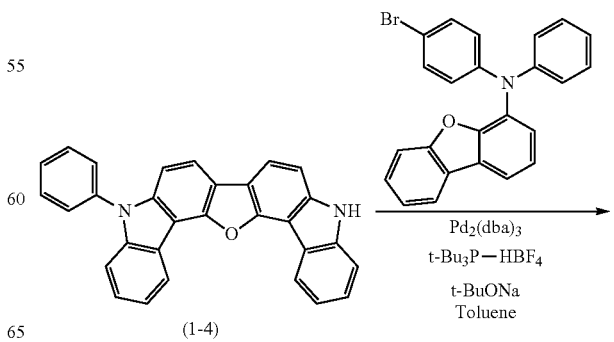

(1-4)

-continued

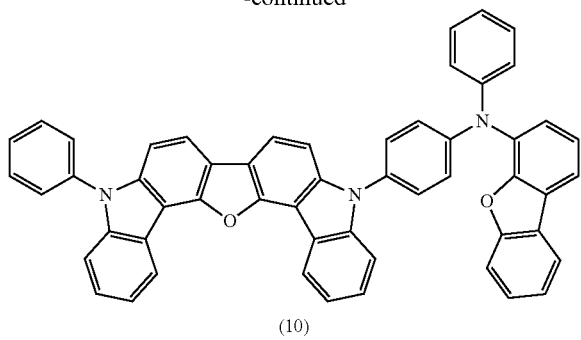

(10)

In a three-neck flask, 2.11 g (5 mmol) of compound (1-4), 2.28 g (5.5 mmol) of compound (10-2), 90 mg (0.1 mmol) of $Pd_2(dba)_3$, 0.12 g (0.4 mmol) of tri-t-butylphosphonium tetrafluoroborate, 0.67 g (7 mmol) of sodium t-butoxide and 30 mL of dehydrated toluene were placed. The resultant was refluxed in an argon atmosphere for 48 hours.

After completion of the reaction, insoluble matters were separated by filtration through celite. The filtrate was transferred to a dripping funnel and extracted several times with toluene. The obtained organic phase was dried with anhydrous magnesium sulfate, filtered and concentrated. The concentrated product was purified by silica gel chromatography (hexane:toluene=3:2), whereby white solids were obtained.

The yield was 1.32 g and the percentage yield was 35%.
As a result of a FD-MS analysis, m/e was 755 relative to the molecular weight of 755.

Synthesis Example 11 (Synthesis of Compound (11))

(1) Synthesis of Compound (11-1)

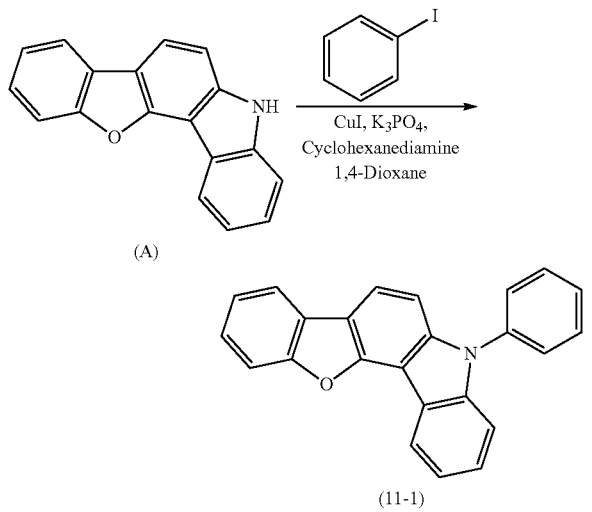

(11-1)

In a three-neck flask, 25.7 g (100 mmol) of intermediate (A) (synthesized according to the method described in WO2009/148015), 21.4 g (105 mmol) of iodobenzene, 19.0 g (100 mmol) of copper iodide, 42.5 g (200 mmol) of potassium triphosphate, 22.8 g (200 mmol) of cyclohexanediamine and 200 mL of dehydrated 1,4-dioxane were placed. The mixture was refluxed in an argon atmosphere for 12 hours.

After completion of the reaction, insoluble matters were separated by filtration through celite. The filtrate was transferred to a dripping funnel and extracted several times with toluene. An organic phase obtained was dried with anhydrous magnesium sulfate, filtered and concentrated. The resultant was purified by silica gel chromatography (hexane:toluene=7:3), whereby white solids were obtained.

The yield was 21.7 g and the percentage yield was 65%.

(2) Synthesis of Compound (11-2)

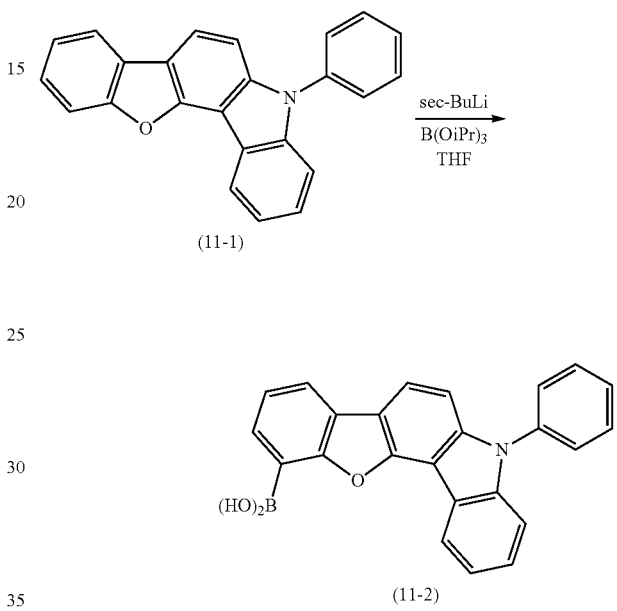

In a three-neck flask, 21.7 g (65 mmol) of compound (11-1) and 400 mL of dehydrated tetrahydrofuran were placed, and cooled to −70° C. in an argon atmosphere. Subsequently, 47 mL of 1.4M sec-butyllithium (hexane-cyclohexane solution) was added dropwise to the reaction solution. After stirring for 2 hours, 36.7 g (195 mmol) of triisopropyl borate was added. After returning to room temperature and stirring was conducted for 3 hours, the reaction solution was concentrated. To residues obtained, dichloromethane and 2N hydrochloric acid were added, followed by stirring for 2 hours, and an organic phase was separated. Solids obtained by concentrating the organic phase were washed with toluene, whereby white solids were obtained.

The yield was 17.2 g and the percentage yield was 70%.

(3) Synthesis of Compound (11-3)

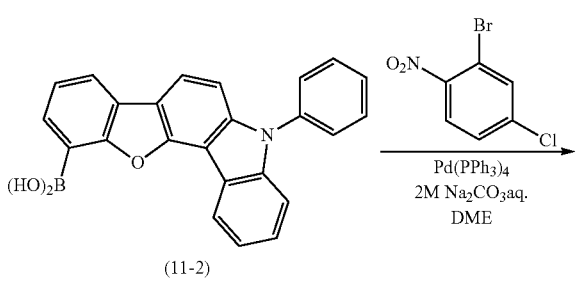

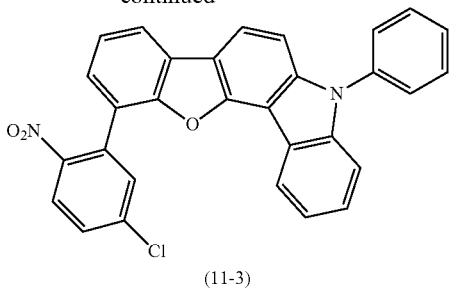

(11-3)

In a three-neck flask, 17.0 g (45 mmol) of compound (11-2), 10.7 g (45 mmol) of 2-bromo-4-chloronitrobenzene, 1.56 g (1.35 mmol) of Pd(PPh$_3$)$_4$, 60 mL of an aqueous 2M sodium carbonate solution and 200 mL of 1,2-dimethoxyethane (DME) were placed. The resultant was refluxed in an argon atmosphere for 24 hours.

After completion of the reaction, insoluble matters were separated by filtration through celite. The filtrate was transferred to a dripping funnel and extracted several times with dichloromethane. An organic phase obtained was dried with anhydrous magnesium sulfate, filtered and concentrated. The concentrated product was purified by silica gel chromatography (hexane:dichloromethane=7:3), whereby white solids were obtained.

The yield was 15.4 g and the percentage yield was 70%.

(4) Synthesis of Compound (11-4)

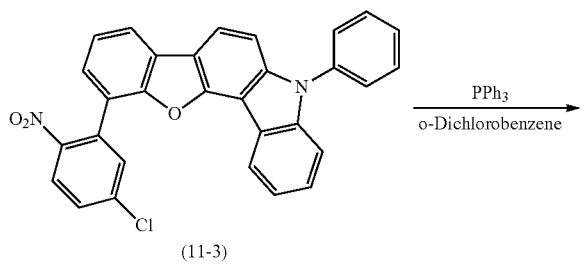

In a three-neck flask, 14.7 g (30 mmol) of compound (11-3), 23.6 g (90 mmol) of triphenylphosphine and 200 mL of o-dichlorobenzene were placed. The resultant was refluxed at 180° C. in an argon atmosphere for 24 hours.

After completion of the reaction, residues obtained by concentrating the reaction solution was purified by silica gel chromatography (hexane:dichloromethane=7:3→1:1), whereby white solids were obtained.

The yield was 8.9 g and the percentage yield was 65%.

(5) Synthesis of Compound (11-5)

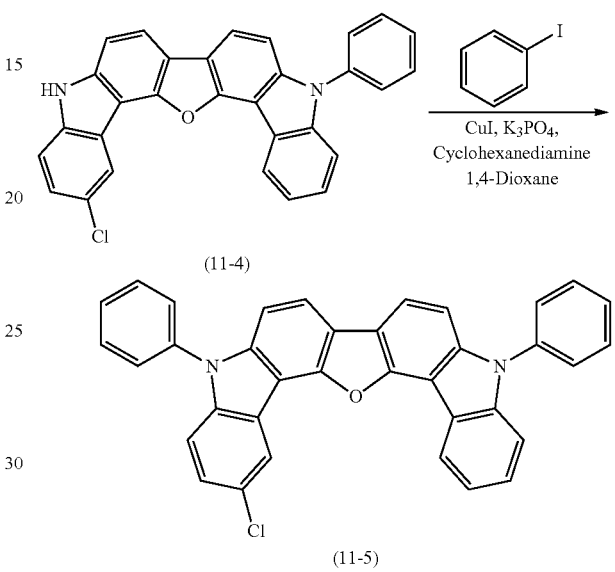

In a three-neck flask, 6.9 g (15 mmol) of compound (11-4), 3.1 g (15 mmol) of iodobenzene, 2.9 g (15 mmol) of copper iodide, 6.4 g (30 mmol) of potassium triphosphate, 3.4 g (30 mmol) of cyclohexanediamine and 60 mL of dehydrated 1,4-dioxane were placed. The resultant was refluxed in an argon atmosphere for 24 hours.

After completion of the reaction, insoluble matters were separated by filtration through celite. The filtrate was transferred to a dripping funnel and extracted several times with toluene. An organic phase obtained was dried with anhydrous magnesium sulfate, filtered and concentrated. The resultant was purified by silica gel chromatography (hexane:toluene=2:1), whereby white solids were obtained.

The yield was 6.8 g and the percentage yield was 85%.

(6) Synthesis of Compound (11)

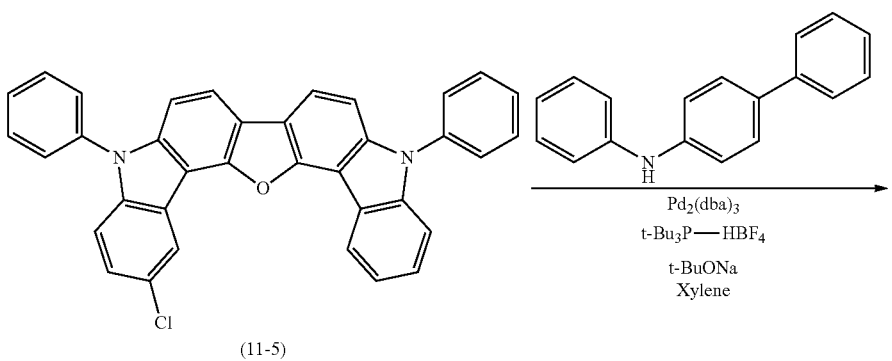

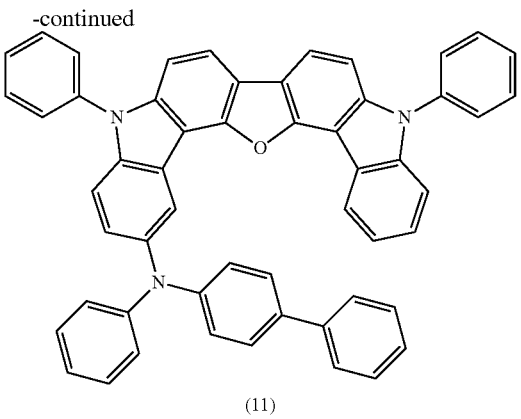

(11)

In a three-neck flask, 2.67 g (5 mmol) of compound (11-5), 1.35 g (5.5 mmol) of (N-phenyl)biphenylamine, 90 mg (0.1 mmol) of Pd$_2$(dba)$_3$, 0.12 g (0.4 mmol) of tri-t-butylphosphonium tetrafluoroborate, 0.67 g (7 mmol) of sodium t-butoxide and 30 mL of dehydrated xylene were placed. The resultant was refluxed for 48 hours in an argon atmosphere.

After completion of the reaction, insoluble matters were separated by filtration through celite. The filtrate was transferred to a dripping funnel and extracted several times with toluene. An organic phase obtained was dried with anhydrous magnesium sulfate, filtered and concentrated. The resultant was purified by silica gel chromatography (hexane:toluene=3:2), whereby white solids were obtained.

The yield was 1.89 g and the percentage yield was 51%.

As a result of a FD-MS analysis, m/e was 741 relative to the molecular weight of 741.

Synthesis Example 12 (Synthesis of Compound (12))

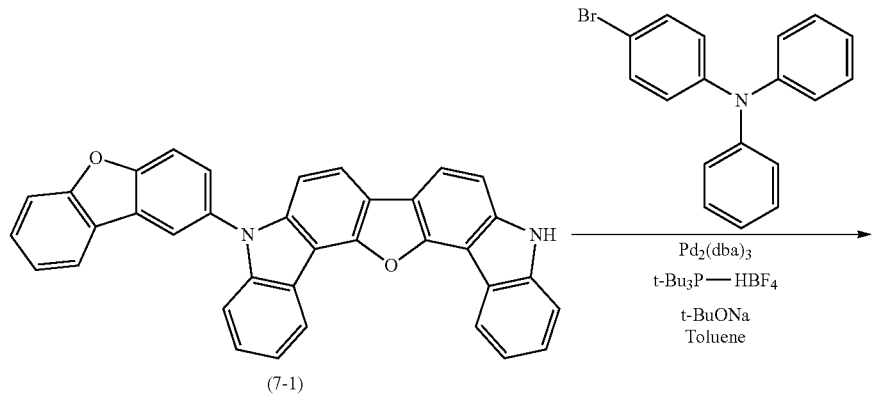

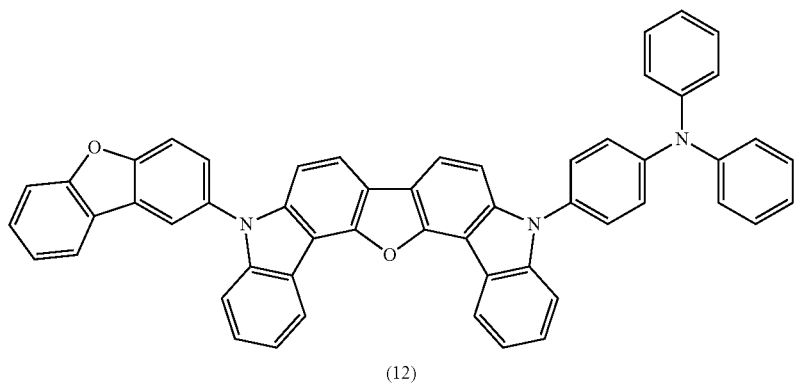

(12)

In a three-neck flask, 2.56 g (5 mmol) of compound (7-1), 1.78 g (5.5 mmol) of 4-bromotriphenylamine, 90 mg (0.1 mmol) of Pd$_2$(dba)$_3$, 0.12 g (0.4 mmol) of tri-t-butylphosphonium tetrafluoroborate, 0.67 g (7 mmol) of tri-t-sodium t-butoxide and 30 mL of dehydrated toluene were placed. The resultant was refluxed in an argon atmosphere for 28 hours.

After completion of the reaction, insoluble matters were separated by filtration through celite. The filtrate was transferred to a dripping funnel and extracted several times with toluene. An organic phase obtained was dried with anhydrous magnesium sulfate, and filtered and concentrated. The resultant was purified by silica gel chromatography (hexane:toluene=3:2), whereby white solids were obtained.

The yield was 2.44 g and the percentage yield was 64%.

As a result of a FD-MS analysis, m/e was 755 relative to the molecular weight of 755.

[Production and Evaluation of Organic EL Device]

Example 1

A glass substrate with 130 nm-thick ITO electrode lines (manufactured by GEOMATEC Co., Ltd.) was subjected to ultrasonic cleaning in isopropyl alcohol for 5 minutes and then UV ozone cleaning for 30 minutes.

The cleaned glass substrate with ITO electrode lines was mounted on a substrate holder in a vacuum deposition apparatus. First, on the surface on which the ITO electrode lines had been formed, compound (HI1) was deposited by resistance heating so as to cover the ITO electrode lines to form a 20 nm-thick film, and subsequently compound (HT1) was deposited by resistance heating to form a 50 nm-thick film. The film-forming rate was 1 Å/s. These thin films function as a hole-injecting layer and a hole-transporting layer, respectively.

Next, on the hole-transporting layer, compound (2) was deposited by resistance heating to form a thin film (electron-barrier layer) with a film thickness of 10 nm.

Subsequently, on the electron-barrier layer, compound (H1) and compound (BD1) were simultaneously deposited by resistance heating to form a 40 nm-thick thin film. At this time, compound (BD1) was deposited such that the mass ratio of compound (BD1) became 20% relative to the total mass of compound (H1) and compound (BD1). The film forming rate was 1.2 Å/s for H1, and 0.3 Å/s for BD1. This thin film functions as a phosphorescent emitting layer.

Subsequently, on the phosphorescent emitting layer, compound (HB1) was deposited by resistance heating to form a 5 nm-thick thin film. The film forming rate was 1.2 Å/s. This thin film functions as a hole barrier layer.

Next, on the hole barrier layer, compound (ET1) was deposited by resistance heating to form a 25 nm-thick thin film. The film forming rate was 1 Å/s. This film functions as an electron-transporting layer.

Subsequently, on this electron-transporting layer, a LiF film having a thickness of 1.0 nm was deposited at a film-forming rate of 0.1 Å/s.

Next, on the LiF film, metal aluminum was deposited at a film forming rate of 8.0 Å/s to form a metal electrode having a film thickness of 80 nm, whereby an organic EL device was produced.

The materials used for the production of the organic EL device are shown below.

HI1
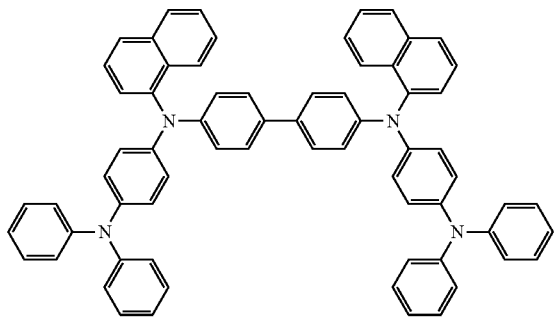

HT1
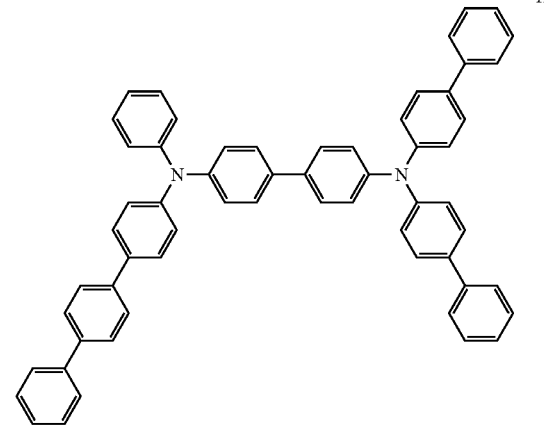

H1
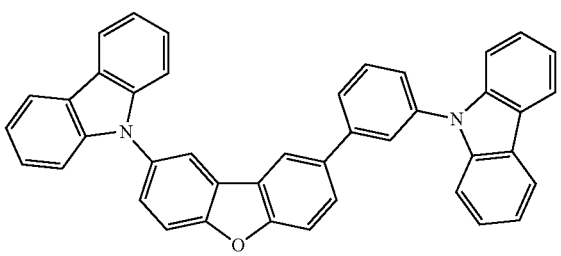

BD1
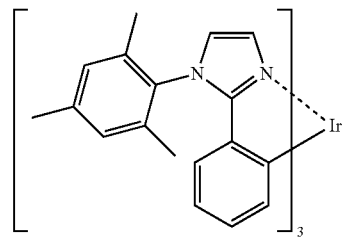

HB1
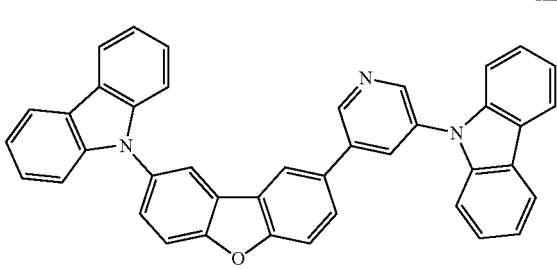

ET1

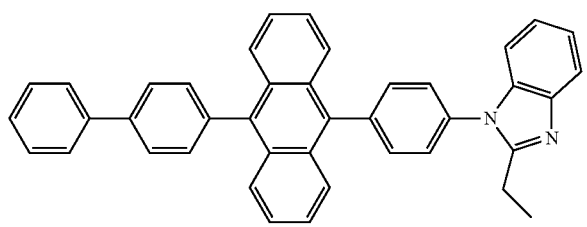

The fabricated organic EL device was caused to emit light by direct current driving to measure a luminance and a current density, whereby a voltage and a luminous efficiency (external quantum efficiency) at a current density of 1 mA/cm² were obtained. Further, a LT70% luminance life (time that elapsed until the initial luminance was reduced to 70%) was measured at an initial luminance of 3000 cd/m². The results of evaluation of these luminous performance are shown in Table 1.

Examples 2 to 8

Organic EL devices were produced and evaluated in the same manner as in Example 1, except that compounds (3) to (9) were used instead of compound (2). The results are shown in Table 1.

Comparative Example 1

An organic EL device was produced and evaluated in the same manner as in Example 1, except that compound (13) was used instead of compound (2). The results are shown in Table 1.

TABLE 1

| | Electron-barrier layer material | Voltage (V) | External quantum efficiency (%) | LT70% luminous time (hour) |
|---|---|---|---|---|
| Example 1 | Compound (2) | 4.4 | 23.4 | 205 |
| Example 2 | Compound (3) | 4.5 | 23.8 | 130 |
| Example 3 | Compound (4) | 4.5 | 21.7 | 163 |
| Example 4 | Compound (5) | 4.4 | 22.6 | 190 |
| Example 5 | Compound (6) | 4.5 | 21.7 | 231 |
| Example 6 | Compound (7) | 4.4 | 23.7 | 127 |
| Example 7 | Compound (8) | 4.4 | 21.4 | 180 |
| Example 8 | Compound (9) | 4.5 | 22.0 | 248 |
| Comp. Ex. 1 | Compound (13) | 4.4 | 22.9 | 78 |
| Comp. Ex. 2 | Compound (1) | 4.6 | 23.9 | 80 |
| Comp. Ex. 3 | Compound (12) | 4.4 | 21.9 | 79 |

As shown in Table 1, the compound of the invention can be used as a material for an electron-barrier layer (hole-transporting layer). In particular, organic EL devices shown in Examples 1 to 8 in which the compound of the invention was used as a material for the electron-barrier layer that is adjacent to the emitting layer had a significantly longer life as compared with the organic EL devices of Comparative Examples 1 to 3 without deteriorating the voltage and the efficiency.

Example 9

A glass substrate with 130 nm-thick ITO electrode lines (manufactured by GEOMATEC Co., Ltd.) was subjected to ultrasonic cleaning in isopropyl alcohol for 5 minutes and then UV ozone cleaning for 30 minutes.

The cleaned glass substrate with ITO electrode lines was mounted on a substrate holder in a vacuum deposition apparatus. First, on the surface of the side on which the ITO (13)

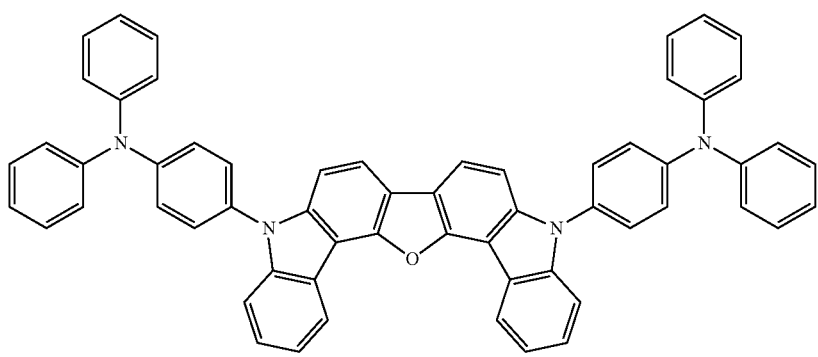

Comparative Example 2

An organic EL device was produced and evaluated in the same manner as in Example 1, except that compound (1) was used instead of compound (2). The results are shown in Table 1.

Comparative Example 3

An organic EL device was produced and evaluated in the same manner as in Example 1, except that compound (12) was used instead of compound (2). The results are shown in Table 1.

electrode lines had been formed, compound (HI1) was deposited by resistance heating so as to cover the ITO electrode lines to form a 20 nm-thick film, and subsequently compound (HT1) was deposited by resistance heating to form a 60 nm-thick film sequentially. The film-forming rate was 1 Å/s. These thin films function as a hole-injecting layer and a hole-transporting layer, respectively.

Subsequently, on the hole-transporting layer, compound (7) and compound (BD1) were simultaneously deposited by resistance heating to form a 40 nm-thick thin film. At this time, compound (BD1) was deposited such that the mass ratio of compound (BD1) became 20% relative to the total mass of compound (7) and compound (BD1). The film forming rate was 1.2 Å/s for compound (7), and 0.3 Å/s for (BD1). This thin film functions as a phosphorescent emitting layer.

Subsequently, on the phosphorescent emitting layer, compound (HB1) was deposited by resistance heating to form a 5 nm-thick thin film. The film forming rate was 1.2 Å/s. This thin film functions as a hole-barrier layer.

Next, on the hole-barrier layer, compound (ET1) was deposited by resistance heating to form a 25 nm-thick thin film. The film forming rate was 1 Å/s. This film functions as an electron-transporting layer.

Subsequently, on this electron-injecting layer, a LiF film having a thickness of 1.0 nm was deposited at a film-forming rate of 0.1 Å/s.

Next, on the LiF film, metal aluminum was deposited at a film forming rate of 8.0 Å/s to form a metal cathode having a film thickness of 80 nm, whereby an organic EL device was produced.

The thus fabricated organic EL device was driven by direct current driving to measure a luminance and a current density, whereby a voltage and a luminous efficiency (external quantum efficiency) at a current density of 1 mA/cm$^2$ were obtained. The results of evaluation of these luminous performance are shown in Table 2.

Example 10

An organic EL device was produced and evaluated in the same manner as in Example 9, except that compound (10) was used instead of compound (7). The results are shown in Table 2.

Comparative Example 4

An organic EL device was produced and evaluated in the same manner as in Example 9, except that compound (13) was used instead of compound (7). The results are shown in Table 2.

TABLE 2

| | Emitting layer host material | Voltage (V) | External quantum efficiency (%) |
|---|---|---|---|
| Example 9 | Compound (7) | 4.0 | 18.6 |
| Example 10 | Compound (10) | 4.2 | 18.3 |
| Comp. Ex. 4 | Compound (13) | 4.4 | 17.6 |

As shown in Table 2, the compound of the invention can be used as a host material of the emitting layer. When compound (7) or compound (10) were used, improvement in efficiency could be confirmed as compared with the case of compound (13).

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The documents described in this specification are incorporated herein by reference in its entirety.

The invention claimed is:

1. A compound represented by the following formula (1):

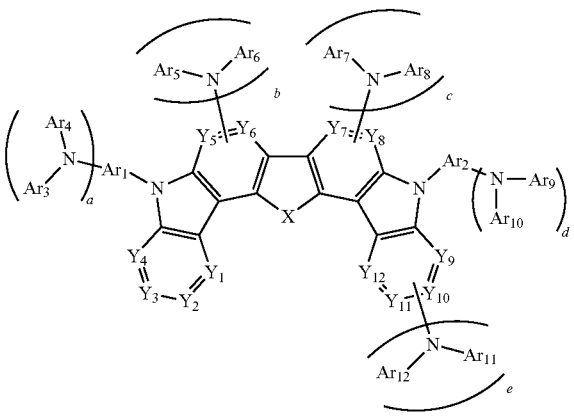

(1)

wherein in the formula (1),
X is O, S or a group represented by N-Ra;
$Y_1$ to $Y_4$ are independently N or a group represented by C-Ra;
$Y_5$ and $Y_6$ are independently N, a group represented by C-Ra or a carbon atom that is bonded to —N(Ar$_5$)(Ar$_6$);
$Y_7$ and $Y_8$ are independently N, a group represented by C-Ra or a carbon atom that is bonded to —N(Ar$_7$)(Ar$_8$);
$Y_9$ to $Y_{12}$ are independently N, a group represented by C-Ra or a carbon atom that is bonded to —N(Ar$_{11}$)(Ar$_{12}$);
Ar$_1$ to Ar$_{12}$ are independently a substituted or unsubstituted aromatic hydrocarbon group including 6 to 30 ring carbon atoms or a substituted or unsubstituted aromatic heterocyclic group including 3 to 30 ring atoms;
Ra is a hydrogen atom, a substituted or unsubstituted aromatic hydrocarbon group including 6 to 30 ring carbon atoms, a substituted or unsubstituted aromatic heterocyclic group including 3 to 30 ring atoms, a substituted or unsubstituted alkyl group including 1 to 30 carbon atoms, a substituted or unsubstituted fluoroalkyl group including 1 to 30 carbon atoms, a substituted or unsubstituted cycloalkyl group including 3 to 30 ring carbon atoms, a substituted or unsubstituted aralkyl group including 7 to 30 carbon atoms, a substituted phosphoryl group, a substituted silyl group, a cyano group, a nitro group or a carboxy group,
when plural Ras are present in the formula (1), the plural Ras may be the same or different from each other, and the plural Ras may form a ring;
when Ar$_1$ is a p-phenylene group, Ar$_3$ and Ar$_4$ are not both an unsubstituted phenyl group;
when Ar$_2$ is a p-phenylene group, Ar$_9$ and Ar$_{10}$ are not both an unsubstituted phenyl group;
a is an integer of 0, 1 or 2;
b is an integer of 0, 1 or 2;
c is an integer of 0, 1 or 2;
d is an integer of 0, 1 or 2;
e is an integer of 0, 1, 2, 3 or 4; and
a+b+c+d+e is 1 to 6.

2. The compound according to claim 1, wherein, in the formula (1), at least one of a and d is 1.

3. The compound according to claim 1, wherein, in the formula (1), a is 0, and b+c+d+e is 1 to 4.

4. The compound according to claim 1, wherein, in the formula (1), e is 0 and a+b+c+d is 1 to 4.

5. The compound according to claim 1, wherein, in the formula (1), a and d are 0 and b+c+e is 1 to 4.

6. The compound according to claim 1, wherein, in the formula (1), a and e are 0 and b+c+d is 1 to 4.

7. The compound according to claim 1, wherein, in the formula (1), a, d and e are 0 and b+c is 1 or 2.

8. The compound according to claim 1, wherein, in the formula (1), a, b and c are 0 and d is 1.

9. The compound according to claim 1, wherein, in the formula (1), a, b, c and e are 0 and d is 1.

10. The compound according to claim 1, wherein $Ar_1$ and $Ar_e$ in the formula (1) are independently a substituted or unsubstituted phenylene group, a substituted or unsubstituted naphthalenediyl group, a substituted or unsubstituted anthracenediyl group, a substituted or unsubstituted triphenylenediyl group, a substituted or unsubstituted fluorenediyl group, a substituted or unsubstituted benzofluorenediyl group, a substituted or unsubstituted biphenyldiyl group, a substituted or unsubstituted terphenyldiyl group, a substituted or unsubstituted phenanthrenediyl group, a substituted or unsubstituted fluoranthenediyl group, a substituted or unsubstituted pyridinediyl group, a substituted or unsubstituted pyrimidinediyl group, a substituted or unsubstituted triazinediyl group, a substituted or unsubstituted dibenzofuranediyl group, a substituted or unsubstituted dibenzothiophenediyl group, a substituted or unsubstituted azadibenzofuranediyl group, a substituted or unsubstituted azadibenzothiophenediyl group, a substituted or unsubstituted diazadibenzofuranediyl group, a substituted or unsubstituted diazadibenzothiophenediyl group, a substituted or unsubstituted carbazolediyl group, a substituted or unsubstituted azacarbazolediyl group or a substituted or unsubstituted diazacarbazolediyl group.

11. The compound according to claim 1, wherein $Ar_1$ and $Ar_2$ in the formula (1) are independently a substituted or unsubstituted m-phenylene group, a substituted or unsubstituted o-phenylene group, a substituted or unsubstituted naphthalenediyl group, a substituted or unsubstituted triphenylenediyl group, a substituted or unsubstituted fluorenediyl group, a substituted or unsubstituted biphenyldiyl group, a substituted or unsubstituted terphenyldiyl group, a substituted or unsubstituted phenanthrenediyl group, a substituted or unsubstituted dibenzofuranediyl group or a substituted or unsubstituted dibenzothiophenediyl group.

12. The compound according to claim 1, wherein $Ar_1$ and $Ar_2$ in the formula (1) are independently a substituted or unsubstituted fluorenediyl group or a substituted or unsubstituted biphenyldiyl group.

13. The compound according to claim 1, wherein $Ar_3$ to $Ar_{12}$ in the formula (1) are independently a substituted or unsubstituted phenyl group, a substituted or unsubstituted naphthyl group, a substituted or unsubstituted anthryl group, a substituted or unsubstituted triphenylenyl group, a substituted or unsubstituted fluorenyl group, a substituted or unsubstituted benzofluorenyl group, a substituted or unsubstituted biphenyl group, a substituted or unsubstituted terphenyl group, a substituted or unsubstituted phenanthryl group, a substituted or unsubstituted fluoranthenyl group, a substituted or unsubstituted pyridinyl group, a substituted or unsubstituted pyrimidinyl group, a substituted or unsubstituted triazinyl group, a substituted or unsubstituted dibenzofuranyl group, a substituted or unsubstituted dibenzothiophenyl group, a substituted or unsubstituted azadibenzofuranyl group, a substituted or unsubstituted azadibenzothiophenyl group, a substituted or unsubstituted diazadibenzofuranyl group, a substituted or unsubstituted diazadibenzothiophenyl group, a substituted or unsubstituted carbazolyl group, a substituted or unsubstituted azacarbazolyl group or a substituted or unsubstituted diazacarbazolyl group.

14. The compound according to claim 1, wherein $Y_1$ to $Y_4$ in the formula (1) are independently a group represented by C-Ra;
$Y_5$ and $Y_6$ are independently a group represented by C-Ra or a carbon atom that is bonded to $N(Ar_5)(Ar_6)$;
$Y_7$ and $Y_8$ are independently a group represented by C-Ra or a carbon atom that is bonded to $N(Ar_7)(Ar_8)$; and
$Y_9$ to $Y_{12}$ are independently a group represented by C-Ra or a carbon atom that is bonded to $N(Ar_{11})(Ar_{12})$.

15. A material for an organic electroluminescence device that comprises the compound according to claim 1.

16. An organic electroluminescence device comprising an anode and a cathode; one or more organic thin film layers including an emitting layer between the anode and the cathode, wherein at least one of the organic thin film layers comprises the material for an organic electroluminescence device according to claim 15.

17. The organic electroluminescence device according to claim 16 that further comprises a hole-transporting zone between the anode and the emitting layer and the hole-transporting zone comprises the material for an organic electroluminescence device.

18. The organic electroluminescence device according to claim 17, wherein the hole-transporting zone is adjacent to the emitting layer.

19. The organic electroluminescence device according to claim 16 that further comprises an electron-transporting zone between the cathode and the emitting layer and the electron-transporting zone comprises the material for an organic electroluminescence device.

20. The organic electroluminescence device according to claim 16, wherein the emitting layer comprises the material for an organic electroluminescence device.

21. The organic electroluminescence device according to claim 16, wherein the emitting layer comprises a phosphorescent emitting material.

22. The organic electroluminescence device according to claim 16, wherein the emitting layer comprises a fluorescent emitting material.

23. An electric equipment in which the organic electroluminescence device according to claim 16 is mounted.

* * * * *